US011723914B2

(12) United States Patent
Schoenfisch et al.

(10) Patent No.: US 11,723,914 B2
(45) Date of Patent: Aug. 15, 2023

(54) NITRIC OXIDE-RELEASING POLYAMINOGLYCOSIDES AS BIODEGRADABLE ANTIBACTERIAL SCAFFOLDS AND METHODS PERTAINING THERETO

(71) Applicant: THE UNIVERSITY OF NORTH CAROLINA AT CHAPEL HILL, Chapel Hill, NC (US)

(72) Inventors: Mark H. Schoenfisch, Chapel Hill, NC (US); Lei Yang, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/497,696

(22) PCT Filed: Mar. 28, 2018

(86) PCT No.: PCT/IB2018/052144
§ 371 (c)(1),
(2) Date: Sep. 25, 2019

(87) PCT Pub. No.: WO2018/178902
PCT Pub. Date: Oct. 4, 2018

(65) Prior Publication Data
US 2020/0030362 A1 Jan. 30, 2020

Related U.S. Application Data
(60) Provisional application No. 62/477,564, filed on Mar. 28, 2017.

(51) Int. Cl.
A61K 31/726 (2006.01)
A01N 43/16 (2006.01)
A01N 59/00 (2006.01)
C08B 37/00 (2006.01)
C12N 15/76 (2006.01)
A61K 47/59 (2017.01)
A61K 31/7036 (2006.01)
C07H 15/234 (2006.01)

(52) U.S. Cl.
CPC ............ *A61K 31/726* (2013.01); *A01N 43/16* (2013.01); *A01N 59/00* (2013.01); *A61K 31/7036* (2013.01); *A61K 47/595* (2017.08); *C08B 37/0063* (2013.01); *C12N 15/76* (2013.01); *C07H 15/234* (2013.01)

(58) Field of Classification Search
CPC .............. A61K 31/7036; A61K 47/595; C07H 15/234; C07H 15/232
See application file for complete search history.

(56) References Cited

U.S. PATENT DOCUMENTS

| | | |
|---|---|---|
| 4,169,079 A | 9/1979 | Tabushi et al. |
| 5,234,933 A | 8/1993 | Marnett et al. |
| 5,326,902 A | 7/1994 | Seipp et al. |
| 5,525,357 A | 6/1996 | Keefer et al. |
| 5,574,027 A | 11/1996 | Bernstein |
| 5,632,981 A | 5/1997 | Saavedra et al. |
| 5,650,442 A | 7/1997 | Mitchell et al. |
| 5,650,447 A | 7/1997 | Keefer et al. |
| 5,714,511 A | 2/1998 | Saavedra et al. |
| 5,814,666 A | 9/1998 | Green et al. |
| 5,840,759 A | 11/1998 | Mitchell et al. |
| 5,910,316 A | 6/1999 | Keefer et al. |
| 6,110,453 A | 8/2000 | Keefer et al. |
| 6,121,441 A | 9/2000 | Simensen et al. |
| 6,180,082 B1 | 1/2001 | Woltering et al. |
| 6,200,558 B1 | 3/2001 | Saavedra et al. |
| 6,261,594 B1 | 7/2001 | Smith et al. |
| 6,451,337 B1 | 9/2002 | Smith et al. |
| 6,911,433 B2 | 6/2005 | Saavedra et al. |
| 7,553,656 B2 | 6/2009 | Gimmestad et al. |
| 7,928,079 B2 | 4/2011 | Hrabie et al. |
| 8,158,580 B2 | 4/2012 | Judice et al. |
| 8,603,454 B2 | 12/2013 | Cheng et al. |
| 8,815,831 B2 | 8/2014 | Onsoyen et al. |
| 8,841,279 B2 | 9/2014 | Taylor et al. |
| 8,987,215 B2 | 3/2015 | Taylor et al. |
| 9,238,038 B2 | 1/2016 | Schoenfisch et al. |
| 9,539,233 B2 | 1/2017 | Ohtake et al. |

(Continued)

FOREIGN PATENT DOCUMENTS

| | | |
|---|---|---|
| CA | 2205564 C | 7/2006 |
| CN | 101049513 A | 10/2007 |

(Continued)

OTHER PUBLICATIONS

Ahonen et al., "Nitric oxide-releasing alginates as mucolytic agents," ACS Biomater. Sci. Eng., 5:3409-3418, (2019).

Ahonen et al., "Nitric oxide-releasing alginate as a biodegradable antibacterial scaffold," 253rd National Metting of the American Chemical Society (ACS) on Advanced Materials, Technologies, Systems, and Processes; San Francisco, CA, Apr. 2-6, 2017— Abstracts of Papers, p. 600, (2017).

Alnaief et al., "Preparation of biodegradable nanoporous microspherical aerogel based on alginate," Carbohydrate Polymers, 84(3):1011-1018, (2011).

Arulsamy, N. et al. "Multiplicity Control in the Polygeminal Diazeniumdiolation of Active Hydrogen Bearing Carbons: Chemistry of a New Type of Trianionic Molecular Propeller," S. J. Am. Chem. Soc.,123:10860-10869, (2001).

(Continued)

Primary Examiner — Leigh C Maier
(74) Attorney, Agent, or Firm — Alston & Bird LLP

(57) ABSTRACT

Provided herein are hyperbranched polyaminoglycosides, where in some embodiments, the hyperbranched polyaminoglycosides are covalently modified to store and release nitric oxide. Some embodiments pertain to methods of making and use of hyperbranched polyaminoglycosides. In some embodiments, the covalently modified hyperbranched polyaminoglycosides may be tailored to release nitric oxide in a controlled manner and are useful for eradication of both gram positive and gram negative bacteria as well as other microbes.

15 Claims, 9 Drawing Sheets

(56) References Cited

U.S. PATENT DOCUMENTS

| | | |
|---|---|---|
| 9,850,322 B2 | 12/2017 | Schoenfisch et al. |
| 10,759,877 B2 | 9/2020 | Schoenfisch et al. |
| 11,026,965 B2 | 6/2021 | Schoenfisch et al. |
| 11,072,668 B2 | 7/2021 | Schoenfisch et al. |
| 2001/0000039 A1 | 3/2001 | Toone et al. |
| 2002/0122857 A1 | 9/2002 | Asai et al. |
| 2003/0078365 A1 | 4/2003 | Stamler et al. |
| 2003/0093143 A1 | 5/2003 | Zhao et al. |
| 2004/0038947 A1 | 2/2004 | Wink et al. |
| 2005/0009789 A1 | 1/2005 | Wink et al. |
| 2005/0085413 A1 | 4/2005 | Jin et al. |
| 2005/0228184 A1 | 10/2005 | Haj-Yehia |
| 2005/0265956 A1 | 12/2005 | Liu et al. |
| 2006/0199785 A1 | 9/2006 | Fahmi et al. |
| 2007/0243131 A1 | 10/2007 | Chen et al. |
| 2008/0305004 A1 | 12/2008 | Anderson et al. |
| 2009/0214618 A1 | 8/2009 | Schoenfisch et al. |
| 2009/0222088 A1 | 9/2009 | Chen et al. |
| 2009/0232863 A1 | 9/2009 | Cheng et al. |
| 2010/0197631 A1 | 8/2010 | Reiner et al. |
| 2010/0305062 A1 | 12/2010 | Onsoyen et al. |
| 2010/0305489 A1 | 12/2010 | Liu et al. |
| 2011/0002999 A1 | 1/2011 | Chen et al. |
| 2011/0150999 A1 | 6/2011 | Chu et al. |
| 2011/0218139 A1 | 9/2011 | Robinson et al. |
| 2012/0034169 A1 | 2/2012 | Schoenfisch et al. |
| 2012/0107229 A1 | 5/2012 | Huang et al. |
| 2013/0096078 A1 | 4/2013 | Yoon et al. |
| 2013/0196951 A1 | 8/2013 | Schoenfisch et al. |
| 2013/0337033 A1 | 12/2013 | Balkus, Jr. et al. |
| 2014/0256658 A1 | 9/2014 | Sinha et al. |
| 2015/0108070 A1* | 4/2015 | Kim ................ C02F 1/683 210/688 |
| 2015/0126467 A1 | 5/2015 | Onsøyen et al. |
| 2015/0225488 A1 | 8/2015 | Schoenfisch et al. |
| 2016/0185891 A1 | 6/2016 | Chambers et al. |
| 2016/0331777 A1 | 11/2016 | Dessen et al. |
| 2016/0346313 A1 | 12/2016 | Nordgard et al. |
| 2016/0361342 A1 | 12/2016 | Hansson et al. |
| 2017/0333456 A1 | 11/2017 | Miranda et al. |
| 2018/0055873 A1 | 3/2018 | Dessen et al. |
| 2019/0197631 A1 | 6/2019 | Schneider |
| 2019/0225747 A1 | 7/2019 | Schoenfisch et al. |
| 2019/0322770 A1 | 10/2019 | Schoenfisch et al. |
| 2019/0343869 A1 | 11/2019 | Schoenfisch et al. |
| 2020/0021657 A1 | 1/2020 | Brinkmann et al. |
| 2020/0216571 A1 | 7/2020 | Schoenfisch et al. |
| 2020/0332061 A1 | 10/2020 | Schoenfisch et al. |
| 2021/0346424 A1 | 11/2021 | Schoenfisch et al. |
| 2021/0347918 A1 | 11/2021 | Schoenfisch et al. |

FOREIGN PATENT DOCUMENTS

| | | |
|---|---|---|
| CN | 102083862 A | 6/2011 |
| CN | 106046382 A | 10/2016 |
| EP | 0726768 B1 | 5/2000 |
| EP | 2547660 B1 | 1/2015 |
| EP | 3185853 A1 | 7/2017 |
| IN | 2010DN04583 A | 11/2010 |
| JP | 2001-524991 A | 12/2001 |
| JP | 2002-518557 A | 6/2002 |
| JP | 2005047979 A | 2/2005 |
| JP | 4285775 B2 | 6/2009 |
| NO | 20050480 L | 4/2005 |
| WO | WO 93/25521 A1 | 12/1993 |
| WO | WO 1996/015797 A1 | 5/1996 |
| WO | WO 1996/032136 | 10/1996 |
| WO | WO 1998/005689 A1 | 2/1998 |
| WO | WO 1998/013358 A1 | 4/1998 |
| WO | WO 00/30658 A1 | 6/2000 |
| WO | WO 2007/085254 A1 | 8/2007 |
| WO | WO 2009/049208 A1 | 4/2009 |
| WO | WO 2010/037179 A1 | 4/2010 |
| WO | WO 2010/096320 A2 | 8/2010 |
| WO | WO 2010/139957 A1 | 12/2010 |
| WO | WO 2010/139958 A1 | 12/2010 |
| WO | WO 2010/139959 A2 | 12/2010 |
| WO | WO 2011/003172 A1 | 1/2011 |
| WO | WO 2012/046994 A2 | 4/2012 |
| WO | WO 2012/116177 A2 | 8/2012 |
| WO | WO 2013/029009 A1 | 2/2013 |
| WO | WO 2014/028847 A1 | 2/2014 |
| WO | WO 2017/060388 A1 | 4/2017 |
| WO | WO 2018/067838 A1 | 4/2018 |
| WO | WO 2018/127819 A1 | 7/2018 |
| WO | WO 2018/178902 A1 | 10/2018 |
| WO | WO 2019/099525 A1 | 5/2019 |
| WO | WO 2019/173539 A1 | 9/2019 |
| WO | WO 2020/139857 A1 | 7/2020 |

OTHER PUBLICATIONS

Barraud et al., "Nitric Oxide: A Key Mediator of Biofilm Dispersal with Applications in Infectious Diseases," Curr. Pharm. Des., 21(1):31-42, (2015).

Barraud et al., "Involvement of Nitric Oxide in Biofilm Dispersal of Pseudomonas aeruginosa," Journal of Bacteriology, 188(21):7344-7353, (2006).

Belley, A. et al., "Assessment by time-kill methodology of the synergistic effects of oritavancin in combination with other antimicrobial agents against Staphylococcus aureus," Antimicrob. Agents Chemother., 52:3820-3822, (2008).

Benkovics et al., "A multifunctional β-cyclodextrin-conjugate photodelivering nitric oxide with fluorescence reporting," International Journal of Pharmaceutics, 531: 614-620 (2017).

Bernkop-Schnurch et al., "Improvement in the mucoadhesive properties of alginate by the covalent attachment of cysteine," Journal of Controlled Release, 71(3):277-285, (2001).

Beveridge, Terry J., "Structures of Gram-Negative Cell Walls and Their Derived Membrane Vesicles," Journal of Bacteriology, 181(16):4725-4733, (1999).

Bhardwaj, Atul, et al., "Adiazen-1-ium-1, 2-diolate analog of 7-azabenzobicyclo [2.2. 1] heptane: Synthesis, nitric oxide and nitroxyl release, in vitro hemodynamic, and antihypertensive studies," Bioorganic & Medicinal Chemistry Letters, 23(9):2769-2774, (2013).

Bjarnsholt et al., "Why chronic wounds will not heal: a novel hypothesis," Wound Rep Reg, 16:2-10, (2008).

Boas and Heegaard, "Dendrimers in drug research," Chem. Soc. Rev., 33(1):43-63, (2004).

Bogdan, Christian, "Nitric oxide and the immune response," Nat. Immunol., 2(10):907-916, (2001).

Bollenbach, T., "Antimicrobial interactions: mechanisms and implications for drug discovery and resistance evolution," Curr. Opin. Microbiol., 27:1-9, (2015).

Calabretta et al., "Antibacterial activities of poly (amidoamine) dendrimers terminated with amino and poly (ethylene glycol) groups," Biomacromolecules, 8(6): 1807-1811, (2007).

Caleffi-Ferracioli et al., "Fast detection of drug interaction in Mycobacterium tuberculosis by a checkerboard resazurin method," Tuberculosis, 93:660-663, (2013).

Caminade et al., "Dendrimers and hyperbranched polymers," Chem. Soc. Rev, 44(12):3870-3873, (2015).

Cao et al., "Synthesis and striking fluorescence properties of hyperbranched poly (amido amine)," J. Macromol. Sci. Pure Appl. Chem., 44(4):417-424, (2007).

Caraher, E. M. et al., "The effect of recombinant human lactoferrin on growth and the antibiotic susceptibility of the cystic fibrosis pathogen Burkholderia cepacia complex when cultured planktonically or as biofilms," J. Antimicrob. Chemother., 60:546-554, (2007).

Carlmark et al., "New methodologies in the construction of dendritic materials," Chem. Soc. Rev., 38(2):352-362, (2009).

Carlmark, A. et al., D"endritic Architechtures Based on bis-MPA: Functional Polymeric Scaffolds for Application-Driven Research," Chem Soc Rev., 42:5858-79, (2013).

Carpenter et al., "Dual action antimicrobials: nitric oxide release from quaternary ammonium-functionalized silica nanoparticles," Biomacromolecules, 13(10):3334-3342, (2012).

(56) References Cited

OTHER PUBLICATIONS

Centers for Disease Control, Antibiotic Resistance Threats in the United States, (2013).

Chakrapani, Harinath, et al., "Nitric oxide prodrugs: diazeniumdiolate anions of hindered secondary amines," Organic Letters, 9(22): 4551-4554, (2007).

Charbonneau et al., "Reduced chlorhexidine tooth stain coverage by sequential administration of monoperoxyphthalic acid in the beagle dog," J. Dent. Res., 76(9):1596-1601, (1997).

Chen et al., "Cytotoxicity, hemolysis, and acute in vivo toxicity of dendrimers based on melamine, candidate vehicles for drug delivery," J. Am. Chem. Soc., 126(32):10044-10048, (2004).

Chen et al., "Selective deprotection of the Cbz amine protecting group for the facile syntehsis of kanmycin A dimers linked at N-3" position," Tetrahedron, 65(31)5922-5927, (2009).

Cheng et al., "Michael Addition Polymerization of Trifunctional Amine and Acrylic Monomer: A Versatile Platform for Development of Biomaterials ," Biomacromolecules, 17(10):3115-3126, (2016).

Ciacci, N., et al., "In vitro Synergism of Colistin and N-acetylcysteine against Stenotrophomonas maltophilia," Antibiotics, 8:101, (2019).

Ciofu, O. & Tolker-Nielsen, T., "Tolerance and Resistance of Pseudomonas aeruginosa Biofilms to Antimicrobial Agents—How P. aeruginosa Can Escape Antibiotics," Front. Microbiol., 10:913, (2019).

Cleland, W.W., "Diothiothreitol, A New Protective Reagent for SH Groups," Biochemical., 3(4):480-482, (1964).

Compound Summary, "PubChem Compound Summary for CID 65430: Gallium citrate ga-67," National Library of Medicine: National Center for Biotechnology Information, (Last accessed Aug. 7, 2020), https://pubchem.ncbi.nlm.nih.gov/compound/Gallium-citrate-ga-67.

Compound Summary, "Gallium citrate Ga-67," Drugbank, (Last accessed Aug. 6, 2020), https://www.drugbank.ca/drugs/DB06784.

Compound Summary, "PubChem Compound Summary for CID 61635, Gallium nitrate," National Library of Medicine: National Center for Biotechnology Information, (Last accessed Aug. 7, 2020) https://pubchem.ncbi.nlm.nih.gov/compound/61635.

Coneski and Schoenfisch, "Nitric oxide release: part III. Measurement and reporting," Chem. Soc. Rev, 41(10):3753-3758, (2012).

Coneski, "Design and Synthesis of Nitric Oxide Releasing Polymers for Biomedical Applications", pp. 122-127, (2010). [Retrieved from the Internet: URL:https://cdr.lib.unc.edu/indexablecontent/uuid:d84bce49-d4dd-4026-96a5-3ea9e82dee9c [retrieved on Oct. 9, 2015]].

Coneski, P.N. and Schoenfisch, M.H., "Synthesis of Nitric Oxide-Releasing Polyurethanes with S-Nitrosothiol-Containing Hard and Soft Segments," Polym Chem., 2(4):906-913, (2011).

Coneski, P.N. et al., "Degradable Nitric Oxide-Releasing Biomaterials via Post-Polymerization Functionalization of Cross-Linked Polyesters," Biomacromolecules, 11(11):3208-3215, (2010).

Cooke et al., "Nitric Oxide and Angiogenesis," Circulation, 105:2133-2135, (2002).

Cooke, John P., "NO and Angiogenesis," Atherosclerosis Suppl., 4(4):53-60, (2003).

Cullen, L. & McClean, S., "Bacterial adaptation during chronic respiratory infections," Pathogens, 4:66-89, (2015).

Cutrone et al., "Mannoside and 1,2-mannobioside β-cyclodextrin-scaffolded NO-photodonors for targeting antibiotic resistant bacteria", Carbohydr. Polym, 199: 649-660, (2018).

Da Silva et al., "Antimicrobial peptide control of pathogenic microorganisms of the oral cavity: A review of the literature," Peptides, 36(2):315-321, (2012).

Damodaran, V.B. and Reynolds, M.M., "Biodegradable S-Nitrosothiol Tethered Multiblock Polymer for Nitric Oxide Delivery," J Mater Chem., 21:5870-5872, (2011).

Davies et al., "Evolutionary diversification of Pseudomonas aeruginosa in an artificial sputum model," BMC Microbiol. 17:3, (2017).

Deng et al., "pH and cation-responsive supramolecular gels formed by cyclodextrin amines in DMSO," Soft Matter, 6:1884-1887, (2010).

Deupree, S. M. & Schoenfisch, M. H., "Morphological analysis of the antimicrobial action of nitric oxide on Gram-negative pathogens using atomic force microscopy," Acta Biomater., 5:1405-1415, (2009).

Draget et al., "Chemical, physical and biological properties of alginates and their biomedical implications," Food Hydrocolloids, 25(2):251-256, (2011).

Drug Development Pipeline Status, "Inhaled Gallium: Phase One", Cystic Fibrosis Foundation, (Last accessed Aug. 13, 2020), https://www.cff.org/Trials/Pipeline/details/10146/Inhaled-Gallium.

Duncan and Izzo, "Dendrimer biocompatibility and toxicity," Adv. Drug Deliv. Rev., 57(14):2215-2237, (2005).

Duong et al., "Functional gold nanoparticles for the storage and controlled release of nitric oxide: applications in biofilm dispersal and intracellular delivery," J. Mater. Chem. B-2, 2(31):5003-5011, (2014).

Elion et al., "Antagonists of Nucleic Acid Derivatives: VIII. Synergism in combinations of biochemically related antimetabolites," J. Biol. Chem., 208:477-488, (1954).

Fang, Ferric C., "Antimicrobial reactive oxygen and nitrogen species: concepts and controversies," Nat. Rev. Micro., 2(10):820-832, (2004).

Feliu, N. et al., "Stability and Biocompatibility of a Library of Polyester Dendrimers in Comparison to Polyamidoamine Dendrimers," Biomaterials., 33(7):1970-1981, (2012).

Fernández-Barat, L. et al., "Phenotypic shift in Pseudomonas aeruginosa populations from cystic fibrosis lungs after 2-week antipseudomonal treatment," J. Cyst. Fibros., 16:222-229, (2017).

Friedman et al., "The negative impact of antibiotic resistance," Clin. Microbiol. Infect., 22:416-422, (2016).

Frost, M.C. and Meyerhoff, M.E., "Synthesis, Characterization, and Controlled Nitric Oxide Release from S-Nitrosothiol-Derivatized Fumed Silica Polyme Filler Particles," J Biomed Mater Res Part A., 72A(4):409-419, (2005).

Fu, et al., "Preparation and reversible photo-crosslinking/photocleavage behavior o 4-methylcoumarin functionalized hyperbranched polyester," Polymer, 49(23): 4981-4988, (2008).

Gabor, G. and Vincze, A., "Determination of Thiols in Non-Aqueous Solutions," Anal Chim Acta., 92(2):429-431, (1977).

Gao and Koo, "Do catalytic nanoparticles offer an improved therapeutic strategy to combat dental biofilms?," Nanomed. Nanotech. Biol. Med., 12(4):275-279, (2017).

Gao, Q, et al., "Synthesis and Characterization of Chitosan-Based Diazeniumdiolates [Abstract]," Polymer Materials Science and Engineering, 24(12):415-421, (2008).

Ghosh, S. & Lapara, T. M., "The effects of subtherapeutic antibiotic use in farm animals on the proliferation and persistence of antibiotic resistance among soil bacteria," ISME J., 1:191-203, (2007).

Gibney et al., "Poly(ethylene imine)s as antimicrobial agents with selective activity," Macromol. Biosci., 12(9):1279-1289, (2012).

Gombotz et al., "Protein release from alginate matrices," Advanced Drug Delivery Reviews, 31(3):267-285, (1998).

Grabowski et al., "Toxicity of surface-modified PLGA nanoparticles toward lung alveolar epithelial cells," International Journal of Pharmaceutics, 454:686-694, (2013).

Haggie, P., and Lueck, J.(Eds), "Agenda for Cystic Fibrosis Foundation Research Conference," Cystic Fibrosis Foundation, (2019), https://www.cff.org/Research/Researcher-Resources/Cystic-Fibrosis-Foundation-Research-Conference/.

Hall, J. R. et al., "Mode of nitric oxide delivery affects antibacterial action," ACS Biomater. Sci. Eng., acsbiomaterials.9b01384 (2019).

Hall-Stoodley et al., "Bacterial Biofilms: from the Natural Environment to Infectious Diseases," Nat. Rev. Micro., 2:95-108, (2004).

Harrison et al., "Development of an ex vivo porcine lung model for studying growth Virulence, And signaling of pseudomonas aeruginosa," Infect. Immun., 82:3312-3323, (2014).

Helander, I. M. & Mattila-Sandholm, T., "Fluorometric assessment of Gram-negative bacterial permeabilization," J. Appl. Microbiol., 88:213-219, (2000).

(56) References Cited

OTHER PUBLICATIONS

Hetrick and Schoenfisch, "Analytical chemistry of nitric oxide," Annu. Rev. Anal. Chem., 2:409-433, (2009).
Hetrick et al., "Anti-biofilm efficacy of nitric oxide-releasing silica nanoparticles," Biomaterials, 30:2782-2789, (2009).
Hopkins, Sean, "Development of high capacity hyperbranched nitric oxide donors for controlling ubcutaneous inflammation," Open Access Dissertation, Michigan Technological University, 154 pages, (2015).
Hossain et al., "Discovery of Two Bacterial Nitric Oxide-Responsive Proteins and Their Roles in Bacterial Biofilm Regulation," Acc. Chem. Res., 50(7):1633-1639, (2017).
Howlin, R. P., et al., "Low-Dose Nitric Oxide as Targeted Antibiofilm Adjunctive Therapy to Treat Chronic Pseudomonas aeruginosa Infection in Cystic Fibrosis," Mol. Ther., 25:2104-2116, (2017).
Hrabie, Joseph A., et al., "New nitric oxide-releasing zwitterions derived from polyamines," The Journal of Organic Chemistry, 58(6):1472-1476, (1993).
Huang et al., "Nitric oxide-loaded echogenic liposomes for nitric oxide delivery and inhibition of intimal hyperplasia," J. Am. Coll. Cardiol., 54(7):652-659, (2009).
Hussain et al., "Glucocorticoids can affect Pseudomonas aeruginosa (ATCC 27853) internalization and intracellular calcium concentration in cystic fibrosis bronchial epithelial cells," Experimental Lung Research, 41(7):383-392, (2015).
Imfeld, T. "Chewing gum—facts and fiction: a review of gum-chewing and oral health," Crit. Rev. Oral. Biol. Med., 10(3):405-419, (1999).
Jin et al., "Nitric Oxide-Releasing Cyclodextrins," Journal of the American Chemical Society, 140: 14178-14184 (2018).
Jin et al., "Biocompatible or biodegradable hyperbranched polymers: from self-assembly to cytomimetic applications," Chem. Soc. Rev., 41 (18):5986-5997, (2012).
Jones et al., "Antimicrobial properties of nitric oxide and its application in antimicrobial formulations and medical devices," Appl. Microbiol. Biotechnol., 88(2):401-407, (2010).
Jones, C.G., "Chlorhexidine: is it still the gold standard?" Periodontology 2000, 15:55-62, (1997).
Kailasan et al., "Synthesis and characterization of thermoresponsive polyamidoamine-polyethylene glycol-poly (d, l-lactide) core-shell nanoparticles." Acta Biomater. 6(3):1131-1139, (2010).
Kaneko et al., "The transition metal gallium disrupts Pseudomonas aeruginosa iron metabolism and has antimicrobial and antibiofilm activity," The Journal of Clinical Investigations, 117(4):877-888, (2007).
Karatasos, K., "Self-Association and Complexation of the Anti-Cancer Drug Doxorubicin with PEGylated Hyperbranched Polyesters in an Aqueous Environment," J Phys Chem B., 117(8):2564-2575, (2013).
Keefer et al., "'NONOates' (1-Substituted Diazen-1-ium-1,2-diolates) as Nitric Oxide Donors: Convenient Nitric Oxide Dosage Forms," Methods in Enzymology, 268:281-293, (1996).
Keefer, Larry K., "Fifty Years of Diazeniumdiolate Research. From Laboratory Curiosity to Broad-Spectrum Biomedical Advances," ACS Chemical Biology, 6(11):1147-1155, (2011).
Keefer, Larry K., "Nitric Oxide (NO)- and Nitroxyl (HNO)-Generating Diazeniumdiolates (NONOates): Emerging Commercial Opportunities," Current Topics in Medicinal Chemistry, 5(7):625-636, (2005).
Khalil et al., "Synergy between Polyethylenimine and Different Families of Antibiotics against a Resistant Clinical Isolate of Pseudomonas aeruginosa," Antimicrob. Agents Chemother., 52:1635-1641, (2008).
Khan et al., "Overcoming Drug Resistance with Alginate Oligosaccharides Able To Potentiate the Action of Selected Antibiotics," Antimicrobial Agents and Chemotherapy, 56(10):5134-5141, (2012).
Kim et al., "NONOates—polyethylenimine hydrogel for controlled nitric oxide release and cell proliferation modulation," Bioconjugate Chem., 22(6):1031-1038, (2011).
Knop et al., "Poly(ethylene glycol) in drug delivery: pros and cons as well as potential alternatives," Angew. Chem. Int. Ed., 49(36):6288-6308, (2010).
Konter, Joerg, et al., "Synthesis of Diazen-1-ium-1, 2-diolates Monitored by the "NOtizer" Apparatus: Relationship between Formation Rates, Molecular Structure and the Release of Nitric Oxide," European Journal of Organic Chemistry, 2007(4): 616-624, (2007).
Kovach, K. et al., "Evolutionary adaptations of biofilms infecting cystic fibrosis lungs promote mechanical toughness by adjusting polysaccharide production," npj Biofilms Microbiomes, 3, (2017).
Kurniasih et al., "Dendritic nanocarriers based on hyperbranched polymers," Chem. Soc. Rev., 44(12):4145-4164, (2015).
Labena et al., "One-pot synthesize of dendritic hyperbranched PAMAM and assessment as a broad spectrum antimicrobial agent and anti-biofilm," Mater. Sci. Eng. C Mater. Biol. Appl., 58:1150-1159, (2016).
Lee et al., "Alginate: properties and biomedical applications," Prog Polym Sci., 37(1):106-126, (2012).
Lenoir et al., "Polyolefin matrixes with permanent antibacterial activity: preparation, antibacterial activity, and action mode of the active species," Biomacromolecules, 7(8):2291-2296, (2006).
Liakos et al., "All-natural composite wound dressing films of essential oils encapsulated in sodium alginate with antimicrobial properties," International Journal of Pharmaceutics, 463(2):137-145, (2014).
Liu et al., "Hollow double-layered polymer microspheres with pH and thermo-responsive properties as nitric oxide-releasing reservoirs," Polym. Chem., 6(17):3305-3314, (2015).
Liu et al., "Synergistic supramolecular encapsulation of amphiphilic hyperbranched polymer to dyes," Macromolecules, 39(23):8102-8111, (2006).
Liu, T. et al., "Hollow Polymer Nanoparticles with S-Nitrosothiols as Scaffolds for Nitric Oxide Release," J Colloid Interface Sci., 459:115-122, (2015).
Lowe et al., "Storage and delivery of nitric oxide via diazeniumdiolated metal organic framework," Micropor. Mesopor. Mat., 181:17-22, (2013).
Lu, Y. et al., "Shape- and Nitric Oxide Flux-Dependent Bactericidal Activity of Nitric Oxide-Releasing Silica Nanorods," Small., 9(12):2189-2198, (2013).
Lu, Y. et al., "S-Nitrosothiol-Modified Nitric Oxide-Releasing Chitosan Oligosacccarides as Antibacterial Agents," Acta Biomater.,12:62-69, (2015).
Luo et al., "Nitric oxide: a newly discovered function on wound healing," Acta Pharmacol. Sin., 26(3):259-264, (2005).
Luo et al., "Poly (ethylene glycol)-conjugated PAMAM dendrimer for biocompatible, high-efficiency DNA delivery," Macromolecules, 35(9):356-3462, (2002).
Lutzke, A. et al., "Nitric Oxide-Releasing S-Nitrosated Derivatives of chitin and Chitosan for Biomedical Applications," J Mater Chem B., 2:7449-7458, (2014).
Lutzke, et al., "Nitric oxide release from a biodegradable cysteine-based polyphosphazene," Journal of Materials Chemistry B, 4(11): 1987-1988, (2016).
Machelart et al., "Intrinsic Antibacterial Activity of Nanoparticles Made of β-Cyclodextrins Potentiates Their Effect as Drug Nanocarriers against Tuberculosis", ACS Nano, 13: 3992-4007, (2019).
Macmicking et al., "Nitric oxide and macrophage function," Annu. Rev. Immunol, 15:323-350, (1997).
Madison, C.J., et al., "Gallium and Nitrite Have Synergistic Antimicrobial Activity," Cystic Fibrosis Conference: Scientific Session VIII: Novel Approaches forTreating Difficult Infections, Abstract, Jun. 26, 2019.
Malmström, E. et al., "Hyperbranched Aliphatic Polyesters," Macromolecules, 28(5):1698-1703, (1995).
Maragos, Chris M., et al., "Complexes of. NO with nucleophiles as agents for the controlled biological release of nitric oxide. Vasorelaxant effects," Journal of Medicinal Chemistry, 34(11):3242-3247, (1991).
Martinez, J. L. & Baquero, F., "Mutation Frequencies and Antibiotic Resistance," Antimicrob. Agents Chemother., 44:1771-1777, (2000).

(56) References Cited

OTHER PUBLICATIONS

Matai et al., "Chemically Cross-Linked Hybrid Nanogels of Alginate and PAMAM Dendrimers as Efficient Anticancer Drug Delivery Vehicles," ACS Biomater. Sci. Eng., 2(2):213-223, (2016).
Mather et al., "Michael addition reactions in macromolecular design for emerging technologies," Prog. Polym. Sci., 31(5):487-531, (2006).
Mendelman, P. M. et al., "Aminoglycoside penetration, inactivation, and efficacy in cystic fibrosis sputum," Am. Rev. Respir. Dis., 132:761-765, (1985).
Miller et al., "Gaseous nitric oxide bactericidal activity retained during intermittent high-dose short duration exposure," Nitric Oxide, 20:16-23, (2009).
Miller et al., "Role of Oxidants in Microbial Pathophysiology," Clinical Microbiology Reviews, 10(1):1-18, (1997).
Miller, MR, and Megson, IL, "Recent developments in nitric oxide donor drugs," Br J Pharmacol.,151 (3):305-321, (2007).
Minandri, F., "Promises and failures of gallium as an antibacterial agent," Future Microbiology, 9(3):379-397, (2014).
Moreno-Sastre et al., "Pulmonary delivery of tobramycin-loaded nanostructured lipid carriers for Pseudomonas aeruginosa infections associated with cystic fibrosis," International Journal of Pharmaceutics, 498:263-273, (2016).
Mourtzis et al., "Synthesis, characterization, and remarkable biological properties of cyclodextrins bearing guanidinoalkylamino and aminoalkylamino groups on their primary side," Chem. Eur. J., 14: 4188-4200 (2008).
Mulani et al., "Emerging Strategies to Combat ESKAPE Pathogens in the Era of Antimicrobial Resistance: A Review," Front. Microbiol., 10, (2019).
Müller, L. et al., "Human airway mucus alters susceptibility of Pseudomonas aeruginosa biofilms to tobramycin, but not colistin," J. Antimicrob. Chemother., 73:2762-2769, (2018).
Nair et al., "Biodegradable polymers as biomaterials," Prog. Polym. Sci., 32(8-9):762-798, (2007).
Nakamoto, H. and Bardwell, J.C.A., "Catalysis of Disulfide Bond Formation and Isomerization in the *Escherichia coli* Periplasm," Biochim Biophys Acta., 1694(1-3):111-119, (2004).
Nichols et al., "Local delivery of nitric oxide: Targeted delivery of therapeutics to bone and connective tissues," Adv. Drug Delivery Rev, 64(12):1177-1188, (2012).
Nordgard et al., "Alterations in Mucus Barrier Function and Matrix Structure Induced by Guluronate Oligomers," Biomacromolecules, 15:2294-2300, (2014).
Nordgard et al., "Oligosaccharides As Modulators of Rheology in Complex Mucous Systems," Biomacromolecules, 12(8):3084-3090, (2011).
O'Halloran, T.V. and Culotta, V.C., "Metallochaperones, an Intercellular Shuttle Service for Metal Ions," J Biol Chem., 275(33):25057-25060, (2000).
Ohwada, Tomohiko, et al., "7-Azabicyclo [2.2. 1] heptane as a structural motif to block mutagenicity of nitrosamines," Bioorganic & Medicinal Chemistry, 19(8): 2726-2741, (2011).
Park et al., "Polydopamine Hollow Nanoparticle Functionalized with N-diazeniumdiolates as a Nitric Oxide Delivery Carrier for Antibacterial Therapy," Adv. Healthcare Mater., 5(16):2019-2024, (2016).
Parzuchowski et al., "Synthesis and characterization of polymethacrylate-based nitric oxide donors," J. Am. Chem. Soc., 124(41):12182-12191, (2002).
Paul et al., "Chitosan and Alginate Wound Dressings: A Short Review," Trends Biomater. Artif. Organs, 18(1):18-23, (2004).
Petersen et al., "The global burden of oral diseases and risks to oral health," Bull. World Health Organ., 83(9):661-669, (2005).
Piras et al., "S-Nitroso-Beta-Cyclodextrins as New Bimodal Carriers: Preparation, Detailed Characterization, Nitric-Oxide Release, and Molecular Encapsulation," Chemistry—An Asian Journal, 8:2768-2778 (2013).

Prabaharan, M. et al., "Amphiphilic Multi-Arm-Block Copolymer Conjugated with Doxorubicin via pH-Sensitive Hydrazone Bond for Tumor-Targeted Drug Delivery," Biomaterials., 30(29):5757-5766, (2009).
Pritchard et al., "A New Class of Safe Oligosaccharide Polymer Therapy To Modify the Mucus Barrier of Chronic Respiratory Disease," Molecular Pharmaceutics, 13(3):863-872, (2016).
Privett, B. J., et al., "Synergy of nitric oxide and silver sulfadiazine against gram-negative, gram-positive, and antibiotic-resistant pathogens," Mol. Pharm., 7:2289-2296, (2010).
Product Overiew, "AR-501 (Gallium Citrate): Novel anti-infective for the growing problem of antibiotic resistance," Aridis Pharmaceuticals, (Last accessed Aug. 13, 2020), https://www.aridispharma.com/ar-501/.
Product Overview, "Ardis Pipeline: Blood Stream Infections : Product Candidates," Aridis Pharmaceuticals, (Last accessed Aug. 13, 2020), https://www.aridispharma.com/product-overview/.
Radvar et al., "Comparison of 3 periodontal local antibiotic therapies in persistent periodontal pockets," J. Periodontol., 67(9):860-865, (1996).
Ragheb, M. N. et al. "Inhibiting the Evolution of Antibiotic Resistance," Mol. Cell, 73:157-165.e5, (2019).
Rees et al., "Role of endothelium-derived nitric oxide in the regulation of blood pressure," Proc. Natl. Acad. Sci., 86(9):3375-3378, (1989).
Reighard et al., "Disruption and eradication of P. aeruginosa biofilms using nitric oxide-releasing chitosan oligosaccharides," Biofouling, 31:775-787, (2015).
Reighard, K. P. & Schoenfisch, M. H., "Antibacterial action of nitric oxide-releasing chitosan oligosaccharides against Pseudomonas aeruginosa under aerobic and anaerobic conditions," Antimicrob. Agents Chemother., 59:6506-6513, (2015).
Riccio and Schoenfisch, "Nitric oxide release: part 1. Macromolecular scaffolds," Chem. Soc. Rev., 41(10):3731-3741, (2012).
Riccio, D.A. et al., "Photoinitiated Nitric Oxide-Releasing Tertiary S-Nitrosothiol-Modified Xerogels," ACS Appl Mater Interfaces., 4(2):796-804, (2012).
Riccio, D.A. et al., "Stöber Synthesis of Nitric Oxide-Releasing S-Nitrosothiol-Modified Silica Particles," Chem Mater., 23(7):1727-1735, (2011).
Robson, Martin C., "Wound Infection: A Failure of Wound Healing Caused by an Imbalance of Bacteria," Surgical Clinics of North America, 77(3):637-650, (1997).
Rouillard, K. R., et al., "Exogenous Nitric Oxide Improves Antibiotic Susceptibility in Resistant Bacteria," Research Presentation: Univ. of North of Carolina Chapel Hill, (2019).
Roy, B. et al., New Thionitrates: Synthesis, Stability, and Nitric Oxide Generation, J Org Chem., 59(23):7019-7026, (1994).
Safdar et al., "Targeted diazeniumdiolates: Localized nitric oxide release from glioma-specific peptides and proteins," Int. J. Pharm., 422(1-2):264-270, (2012).
Santajit, S. & Indrawattana, N., "Mechanisms of Antimicrobial Resistance in ESKAPE Pathogens," Biomed Res. Int., 2016:1-8, (2016).
Schaffer et al., "Nitric oxide regulates wound healing," J. Surg. Res., 63(1):237-240, (1996).
Schairer et al., "The potential of nitric oxide releasing therapies as antimicrobial agents," Virulence, 3:271-279, (2012).
Schomburg et al., "Preparation, Purification, and Analysis of Alkylated Cyclodextrins," J. High Res. Chromatog., 15:579-584, (1992).
Seabra, A.B. et al., "Antibacterial Nitric Oxide-Releasing Polyester for the Coating of Blood-Contacting Artificial Materials," Artif Organs, 34(7):E204-14, (2010).
Shah et al., "Synthesis of S-nitrosoglutathione-alginate for prolonged delivery of nitric oxide in intestines," Drug Deliv., 23(8):2927-2935, (2016).
Shishido, S.M. and Oliveira, M.G., "Polyethylene Glycol Matrix Reduces the Rates of Photochemical and Thermal Release of Nitric Oxide from S-Nitroso-N-Acetylcysteine," Photochem Photobiol., 71(3):273-80, (2000).
Singh et al., "Biotechnological applications of cyclodextrins," Biotechnol. Adv., 20:341-359, (2002).

(56) References Cited

OTHER PUBLICATIONS

Singh, Simrat Pal, et al., "Rice Nicotianamine Synthase 2 expression improves dietary iron and zinc levels in wheat," Theoretical and Applied Genetics, 130(2): 283-292, (2017).
Slomberg, D.L. et al., "Role of Size and Shape on Biofilm Eradication for Nitric Oxide-releasing Silica," ACS Appl. Mater. Interfaces, 5(19):9322-9329, (2013).
Slots et al., "Antibiotics in periodontal therapy: advantages and disadvantages," J. Clin. Periodontol., 17(7 (Pt2)):479-493, (1990).
Solleti et al., "Antimicrobial properties of liposomal azithromycin for Pseudomonas infections in cystic fibrosis patients," J Antibacrob Chemother, 70:784-796, (2015).
Soto et al., "Design Considerations for Silica-Partice-Doped Nitric-Oxide-Releasing Polyurethane Glucose Biosensor Membranes," ACS Sensors, 2(1):140-150, (2017).
Spellberg, B., et al., "The Epidemic of Antibiotic-Resistant Infections: A Call to Action for the Medical Community from the Infectious Diseases Society of America," Clin. Infect. Dis., 46:155-164, (2008).
Stasko et al., "Cytotoxicity of polypropylenimine dendrimer conjugates on cultured endothelial cells," Biomacromolecules, 8(12):3853-3859, (2007).
Stasko, N.A. et al., "S-Nitrosothiol-Modified Dendrimers as Nitric Oxide Delivery Vehicles," Biomacromolecules, 9(3):834-841, (2008).
Suchyta and Schoenfisch, "Controlled release of nitric oxide from liposomes," ACS Biomater. Sci. Eng., 3(9):2136-2143, (2017).
Tomalia et al., "A New Class of Polymers: Starburst-Dendritic," Polym. J, 17:117-132, (1985).
Valko, M. et al., "Metals, Toxicity and Oxidative Stress," Curr Med Chem., 12(10):1161-1208, (2005).
Van Strydonck et al., "Plaque inhibition of two commercially available chlorhexidine mouthrinses," J. Clin. Periodontol., 32(3):305-309, (2005).
Vizitiu et al., "Binding of phosphates to aminocyclodextrin biomimetics," J. Org. Chem., 64(17):6235-6238, (1999).
Voit and Lederer, "Hyperbranched and highly branched polymer architectures—synthetic strategies and major characterization aspects," Chem. Rev., 109(11):5924-5973, (2009).
Wan, A., et al., "Characterization of folate-graft-chitosan as a scaffold for nitric oxide release," International Journal of Biological Macromolecules, Elsevier B.V. 43:415-421, (2008).
Wan, A., et al., "Effects of Molecular Weight and Degree of Acetylation on the Release of Nitric Oxide from Chitosan—Nitric Oxide Adducts," Journal of Applied Polymer Science, Wiley Periodicals, Inc., 117:2183-2188, (2010).
Wang et al., "Synthesis and applications of stimuli-responsive hyperbranched polymers," Prog. Polym. Sci., 64:114-153, (2017).
Wang et al., "Synthesis and evaluation of phenylalanine-modified hyperbranched poly (amido amine) s as promising gene carriers," Biomacromolecules, 11(1):241-251, (2009).
Wang, J. and Xu, Tongwen, "Facile Construction of Multivalent Targeted Drug Delivery System from Boltorn® Series Hyperbranched Aliphatic Polyester an Folic Acid," Poly Adv Technol., 22:763-767, (2009).
Williams, D.L.H., "S-Nitrosation and the Reactions of S-Nitroso Compounds," Chem Soc Rev., 14(2):171-196, (1985).
Williams, D.L.H., "The Chemistry of S-Nitrosothiols," Acc Chem Res., 32(10):869-876, (1999).
Wink et al., "DNA deaminating ability and genotoxicity of nitric oxide and its progenitors," Science, 254(5034):1001-1003, (1991).
Wo et al., "Recent advances in thromboresistant and antimicrobial polymers for biomedical applications: just say yes to nitric oxide (NO)," Biomater. Sci., 4(8):1161-1183, (2016).
Wold et al., "Fabrication of Biodegradable Polymeric Nanofibers with Covalently Attached NO Donors," ACS Appl. Mater. Interfaces, 4(6):3022-3030, (2012).
Wu et al., "'Living' controlled in situ gelling systems: thiol-disulfide exchange method toward tailor-made biodegradable hydrogels," J. Am. Chem. Soc., 132(43):15140-15143, (2010).
Xiao, Y.L. et al., "Multifunctional Unimoiecular Micelles for cancer-Targeted Drug Delivery and Positron Emission Tomography Imaging," Biomaterials, 33(11):3071-3082, (2012).
Xu et al., "Well-defined poly (2-hydroxyl-3-(2-hydroxyethylamino) propyl methacrylate) vectors with low toxicity and high gene transfection efficiency," Biomacromolecules, 11(6):1437-1442, (2010).
Yapor, J.P. et al., "Biodegradable Citrate-Based Polyesters with S-Nitrosothiol Functional Groups for Nitric Oxide Release," J Mater Chem B., 3(48):9233-9241, (2015).
Žagar, E. and Žigon, M., "Aliphatic Hyperbranched Polyesters Based on 2,2-bis(methylol)propionicAcid—Determination of Structure, Solution and Bulk Properties," Prog Polymer Sci., 36(1):53-88, (2011).
Zamboulis et al: "Polyglycerol Hyperbranched Polyesters: Synthesis, Properties and Pharmaceutical and Biomedical Applications," International Journal of Molecular Sciences, 20(24):6210, (2019).
Zeng, X.H. et al., "Endocytic Uptake and Intracellular Trafficking of Bis-MPA-Based Hyperbranched Copolymer Micelles in Breast Cancer Cells," Biomacromolecules, 13(11):3814-3822, (2012).
Zhai, X. et al., "Amphiphilic Dendritic Molecules: Hyperbranched Polyesters with Alkyl-Terminated Branches," Macromolecules, 36(9):3101-3110, (2003).
Zhang et al., "Nitric oxide-releasing fumed silica particles: synthesis, characterization, and biomedical application," J. Am. Chem. Soc., 125(17):5015-5024, (2003).
Zhang et al., "A physical gel made from hyperbranched polymer gelator," Chem. Commun., 25:2587-2589, (2007).
Zhang et al., "Antibacterial cotton fabric grafted with silver nanoparticles and its excellent laundering durability," Carbohydr. Polym., 92(2):2088-2094, (2013).
Zhang et al., "Synthesis of an amino-terminated hyperbranched polymer and its application in reactive dyeing on cotton as a salt-free dyeing auxiliary," Color. Technol., 123(6):351-357, (2007).
Zhang et al., "The antimicrobial activity of the cotton fabric grafted with an amino-terminated hyperbranched polymer," Cellulose, 16:281-288, (2009).
Zhang, H. et al., "Hyperbranched Polyester Hydrogels with Controlled Drug Release and Cell Adhesion Properties," Biomacromolecules, 14(5):1299-1310, (2013).
Zhang, X.F. et al., "Nitric Oxide Delivery by Core/Shell Superparamagnetic Nanoparticle Vehicles with Enhanced Biocompatibility," Langmuir., 28(35):12879-12885, (2012).
Zhong, Yong-Li, et al., "Scalable Synthesis of Diazeniumdiolates: Application to the Preparation of MK-8150," Organic letters, 21(11):4210-4214, (2019).
European Application No. 18775628.3, Extended European Search Report dated Sep. 28, 2020.
European Application No. 18812540.5, Communication pursuant to Rules 161(1) and 162 EPC, dated Jul. 8, 2020.
European Search Report and Search Opinon dated Aug. 3, 2020 by the European Search Authority for EP Application No. 18736471.6 (8 pages).
European Search Report dated May 4, 2020 by the European Search Authority for EP Application No. 17859196.2 (32 pages).
Supplementary European Search Report dated Feb. 5, 2016 in EP Application No. 13829755.1.
U.S. Appl. No. 16/459,015, Requirement for Restriction/Election dated Oct. 9, 2019.
WIPO Application No. PCT/IB2018/050051, PCT International Search Report and Written Opinion of the International Searching Authority dated Jun. 8, 2018.
WIPO Application No. PCT/US2013/055360, PCT International Search Report and Written Opinion of the International Searching Authority dated Dec. 23, 2013.
WIPO Application No. PCT/US2017/055371, PCT International Preliminary Report on Patentability dated Apr. 9, 2019.
WIPO Application No. PCT/US2017/055371, PCT International Search Report and Written Opinion of the International Searching Authority dated Dec. 28, 2017.
WIPO Application No. PCT/US2018/061061, PCT International Search Report and Written Opinion of the International Searching Authority dated Apr. 5, 2019.

(56) References Cited

OTHER PUBLICATIONS

WIPO Application No. PCT/US2019/021051, PCT International Search Report and Written Opinion of the International Searching Authority dated Jun. 21, 2019.
WIPO Application No. PCT/US2019/068412, PCT International Search Report and Written Opinion of the International Searching Authority dated May 21, 2020.
Pubchem CID 6032, "Kanamycin A," PubChem, NCBI, pp. 1-9, (2005).
WIPO Application No. PCT/IB2018/052144, PCT International Search Report and Written Opinion of the International Searching Authority dated Aug. 8, 2018.
Backlund et al., "Anti-biofilm action of nitric oxide-releasing alkyl-modified poly(amidoamine) dendrimers against Streptococcus mutans," Acta Biomaterialia, 29:198-205, (2016).
Backlund et al., "Antibacterial Efficacy of Exogenous Nitric Oxide on Periodontal Pathogens," J Dent Res, 93(11):1089-1094, (2014).
Backlund et al., "Kinetic-dependent Killing of Oral Pathogens with Nitric Oxide," J Dent Res, 94(8):1092-1098, (2015).
Carpenter et al., "Nitric oxide release: Part II. Therapeutic applications," Chem. Soc. Rev., 41:3742-3752, (2012).
Hetrick et al., "Bactericidal Efficacy of Nitric Oxide-Releasing Silica Nanoparticles," ACS Nano, 2(2):235-246, (2008).
Lu et al., "Nitric oxide-releasing chitosan oligosaccharides as antibacterial agents," Biomaterials, 35:1716-1724, (2014).
Lu et al., "Structurally Diverse Nitric Oxide-Releasing Poly(propylene imine) Dendrimers," Chem. Mater., 23:4227-4233, (2011).
Polizzi et al., "Water-Soluble Nitric Oxide-Releasing Gold Nanoparticles," Langmuir, 23:4938-4943, (2007).
Privett et al., "Examination of bacterial resistance to exogenous nitric oxide," Nitric Oxide, 26:169-173, (2012).
Shin et al., "Inorganic/Organic Hybrid Silica Nanoparticles as a Nitric Oxide Delivery Scaffold," Chem. Mater., 20:239-249, (2008).
Soto et al., "Functionalized Mesoporous Silica via an Aminosilane Surfactant Ion Exchange Reaction: Controlled Scaffold Design and Nitric Oxide Release," ACS Appl. Mater. Interfaces, 8:2220-2231, (2016).
Stasko et al., "Dendrimers as a Scaffold for Nitric Oxide Release," J. Am. Chem. Soc., 128:8265-8271, (2006).
Sun et al., "Nitric Oxide-Releasing Dendrimers as Antibacterial Agents," Biomacromolecules, 13:3343-3354, (2012).
Worley et al., "Nitric Oxide-Releasing Quaternary Ammonium-Modified Poly(amidoamine) Dendrimers as Dual Action Antibacterial Agents," Bioconjugate Chem., 25:918-927, (2014).
Worley et al., "Anti-Biofilm Efficacy of Dual-Action Nitric Oxide-Releasing Alkyl Chain Modified Poly(amidoamine) Dendrimers," Mol. Pharmaceutics, 12:1573-1583, (2015).
Yang et al., "S-Nitrosothiol-modified hyperbranched polyesters," Polym. Chem., 7:7161-7169, (2016).
Kassebaum et al., "Global Burden of Untreated Caries: A Systematic Review and Metaregression," Journal of Dental Research, 94(5):650-658, (2015).
Beck et al., "Systemic Effects of Periodontitis: Epidemiology of Periodontal Disease and Cardiovascular Disease," J. Periodontol., 76(11)(Suppl.):2089-2100, (2005).
Sen et al., "Periodontal Disease and Recurrent Vascular Events in Stroke/TIA Patients," J. Stroke Cerebrovasc Dis., 22(8):1420-1427, (2013).
Southerland et al., "Periodontitis and diabetes associations with measures of atherosclerosis and CHD," Atherosclerosis, 222(1):196-201, (2012).
Paster et al., "The breadth of bacterial diversity in the human periodontal pocket and other oral sites," Periodontology, 42:80-87, (2000).
Chen et al., "Cariogenic Actinomyces Identified with a β-Glucosidase-Dependent Green Color Reaction to Gardenia jasminoides Extract," Journal of Clinical Microbology, 39(8):3009-3012, (2001).
Loesche et al., "Role of Streptococcus mutans in Human Dental Decay," Microbiological Reviews, 50(4):353-380, (1986).
Zambon, Joseph J., "Actinobacillus actinomycetemcomitans in human periodontal disease," Journal of Clinical Periodontology, 12(1):1-20, (1985).
Allaker, R.P., "The use of Nanoparticles to Control Oral Biofilm formation," J Dent Res, 89(11):1175-1186, (2010).
Besinis et al., "Review of Nanomaterials in Dentistry: Interactions with the Oral Microenvironment, Clinical Applications, Hazards, and Benefits," ACS Nano, 9(3):2255-2289, (2015).
Paula et al., "Nanosized Building Blocks for Customizing Novel Antibiofilm Approaches," Journal of Dental Research, 96(2):128-136, (2017).
Duong et al., "Nanoparticle (Star Polymer) Delivery of Nitric Oxide Effectively Negates Pseudomonas aeruginosa Biofilm Formation," Biomacromolecules, 15:2583-2589, (2014).
Park et al., "Nitric oxide integrated polyethylenimine-based tri-block copolymer for efficient antibacterial activity," Biomaterials, 34:8766-8775, (2013).
Gao et al., "Hyperbranched polymers: from synthesis to applications," Prog. Polym. Sci., 29(3):183-275, (2004).
Wang et al., "Bioapplications of hyperbranched polymers," Chemical Society Reviews, 44:4023-4071, (2015).
Zheng et al., "Hyperbranched polymers: Advances from synthesis to applications," Chemical Society Reviews, 44:4091-4130, (2015).
Chen et al., "Hyperbranched glycoconjugated polymer from natural small molecule kanamycin as a safe and efficient gene vector," Polym. Chem., 2:2674-2682, (2011).
Chen et al., "Multifunctional Hyperbranched Glycoconjugated Polymers Based on Natural Aminoglycosides," Bioconjugate Chemistry, 23(6):1189-1199, (2012).
Huang et al., "Reduction-responsive multifunctional hyperbranched polyaminoglycosides with excellent antibacterial activity, biocompatibility and gene transfection capability," Biomaterials, 106:134-143, (2016).
Nguyen et al., "Co-delivery of nitric oxide and antibiotic using polymeric nanoparticles," Chem. Sci., 7(2):1016-1027, (2016).
Breed et al., "The Number of Colonies Allowable on Satisfactory Agar Plates," Journal of Bacteriology, 1(3):321-331, (1916).
Zhou et al., "Water-Soluble Poly(ethylenimine)-Based Nitric Oxide Donors: Preparation, Characterization and Potential Application in Hemodialysis," Biomacromolecules, 7(9): 2565-2574, (2006).
Chen et al., "Hyperbranched polymers from A2 +B 3 strategy: recent advances in description and control of fine topology," Polym. Chem., 7(22):3643-3663, (2016).
Davies et al., "Chemistry of the Diazeniumdiolates. 2. Kinetics and Mechanism of Dissociation to Nitric Oxide in Aqueous Solution," J. Am. Chem. Soc., 123(23):5473-5481, (2001).
Keefer et al., "Chemistry of the Diazeniumdiolates. 1. Structural and Spectral Characteristics of the [N(O)NO]-Functional Group," Nitric Oxide, 5(4):377-394, (2001).
Zhu et al., "Influence of Branching Architecture on Polymer Properties," Journal of Polymer Science Part B: Polymer Physics, 49(18):1277-1286, (2011).
Wang et al., "Synthesis and Gene Delivery of Poly(amido amine)s with Different Branched Architecture," Biomacromolecules, 11(2):489-495, (2010).
Wang et al., "The effect of a branched architecture on the antimicrobial activity of poly(sulfone amines) and poly(sulfone amine)/silver nanocomposites" J. Mater. Chem., 22:15227-15234, (2012).
Lu et al., "Nitric Oxide-Releasing Amphiphilic Poly(amidoamine) (PAMAM) Dendrimers as Antibacterial Agents," Biomacromolecules, 14(10):3589-3598 (2013).
Hu et al., "A smart aminoglycoside hydrogel with tunable gel degradation, on-demand drug release, and high antibacterial activity," Journal of Controlled Release, 247:145-152, (2017).
Hopkins, Sean, "Development of High Capacity Hyperbranched Nitric Oxide Donors for Controlling Subcutaneous Inflammation," Access Dissertation, Michigan Technological University, (2015).
Yang, Lei et al., "Antibacterial Activity of Nitric Oxide-Releasing Hyperbranched Polyamidoamines," Bioconjugate Chem., 29:35-43, (2018).
Chinese Application No. 201880080277.6, First Office Action, dated Sep. 3, 2021.

(56) References Cited

OTHER PUBLICATIONS

WIPO Application No. PCT/US2019/068412, PCT International Preliminary Report on Patentability dated Jul. 8, 2021.

Falcone et al., "Rheological and cohesive properties of hyaluronic acid," j. Biomed. Mater. Res., Part A, 76A(4):721-728, (2005).

Zhou et al., "Polymethacrylate-Based Nitric Oxide Donors with Pendant N-Diazeniumdiolated Alkyldiamine Moieties: Synthesis, Characterization, and Preparation of Nitric Oxide Releasing Polymeric Coatings," Biomacromolecules, 6:780-789, (2005).

U.S. Appl. No. 16/725,566, Non-Final Office Action dated Jun. 10, 2021.

Newton, David E., Chemistry of New Materials, Shanghai Science and Technology Literature Press, p. 184, (Jul. 31, 2008).

Smith et al., "Nitric Oxide-Releasing Polymers Containing the AN(O)NoU-Group," Journal of Medicinal Chemistry, 39:1148-1157, (Jan. 1996).

Australian Application 2018205823, Examination Report No. 1 for standard patent application dated Sep. 15, 2021.

EP Application No. 18812540.5, Communication Pursuant to Article 94(3) dated Oct. 14, 2021.

EP Application No. 19763961.0, Extended European Search Report dated Nov. 19, 2021.

JP Application No. 2019-553558, Notice of Reasons for Refusal dated May 9, 2022.

JP Application No. 2019-556425, Notice of Reasons for Refusal dated Oct. 26, 2021.

\* cited by examiner

FIB. 4C

Dendritic units
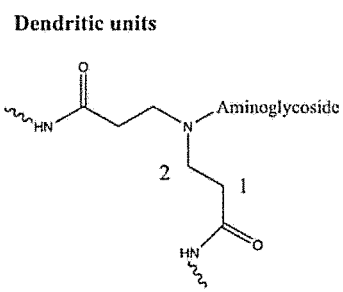
Linear units
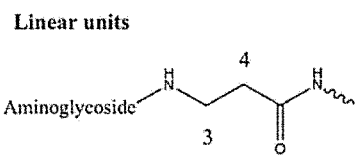
Terminal units
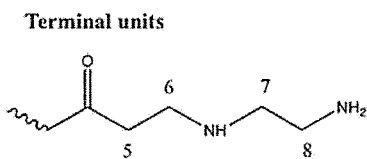
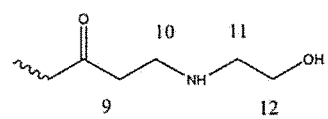
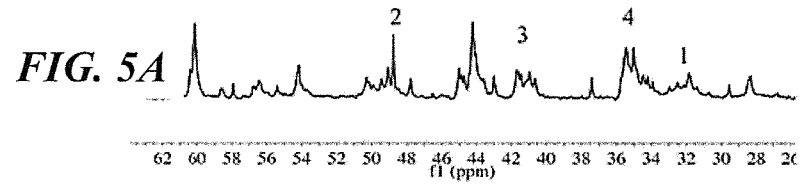
FIG. 5A
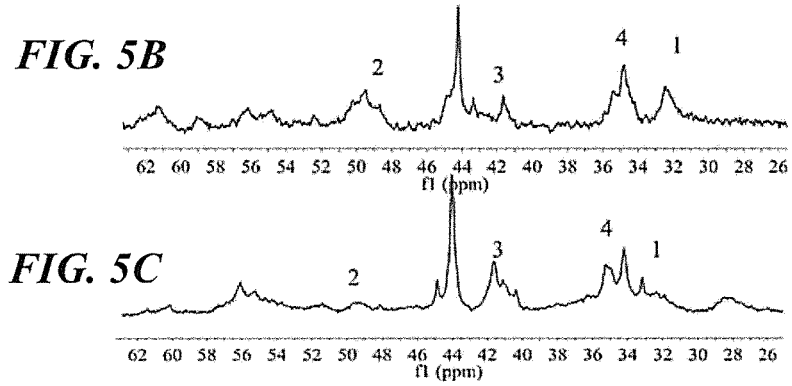
FIG. 5B
FIG. 5C
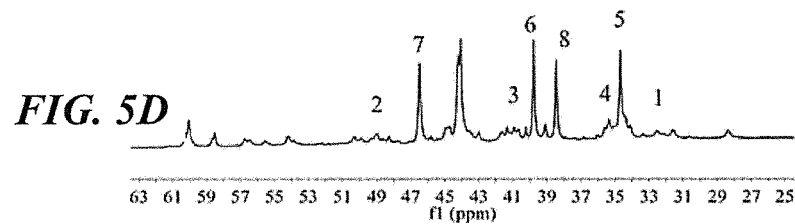
FIG. 5D
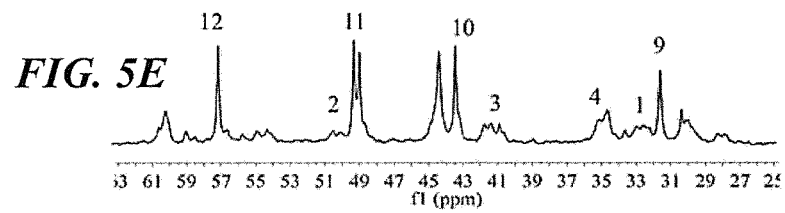
FIG. 5E

NITRIC OXIDE-RELEASING POLYAMINOGLYCOSIDES AS BIODEGRADABLE ANTIBACTERIAL SCAFFOLDS AND METHODS PERTAINING THERETO

INCORPORATION BY REFERENCE OF ANY PRIORITY APPLICATIONS

This patent application is a national stage application filed under 35 U.S.C. § 371 of International Application No. PCT/IB2018/052144, filed Mar. 28, 2018, which claims the benefit of priority to U.S. Provisional Patent Application No. 62/477,564, filed Mar. 28, 2017, each of which is hereby incorporated by reference in its entirety for all purposes.

GOVERNMENT INTEREST

This invention was made with government support under Grant Number DE025207 awarded by The National Institutes of Health. The Government has certain rights in the invention.

BACKGROUND

Field

The presently disclosed subject matter relates generally to nitric oxide-releasing hyperbranched aminoglycosides modified (e.g., covalently) with units that store and/or release nitric oxide in a controlled manner. Additionally disclosed are methods of synthesis and use of the same as antibacterial agents.

Description of the Related Art

Bacterial infections pose a great challenge to human health in community and hospital settings. Biofilms are cooperative communities of bacteria encapsulated by an exopolysaccharide (EPS) matrix protecting the bacteria from host immune response and antibiotics.

SUMMARY

Nitric oxide (NO) plays a variety of physiological roles as a signaling molecule and, as disclosed herein, can also play significant roles in treating or ameliorating pathophysiology, for example as a therapeutic agent. NO as a therapeutic has heretofore been underused, based at least in part on limited NO payloads of therapeutic compositions, NO release rates that are more rapid than desired, and the lack of targeted NO delivery. Provided herein are NO-releasing constructs, methods of producing such constructs, and methods of treating various pathophysiologies using such constructs that leverage the enhanced NO-release characteristics and harness the abundant potential of NO-releasing pharmacological compounds. In particular, provided herein are compounds that are highly efficacious as antimicrobials.

For example, in several embodiments there are provided polyaminoglycosides that release NO and exhibit potent antimicrobial characteristics. In several embodiments, the polyaminoglycosides are functionalized hyperbranched polyaminoglycosides. In several embodiments, such functionalized hyperbranched polyaminoglycosides comprise a first aminoglycoside unit comprising the structure of Formula II:

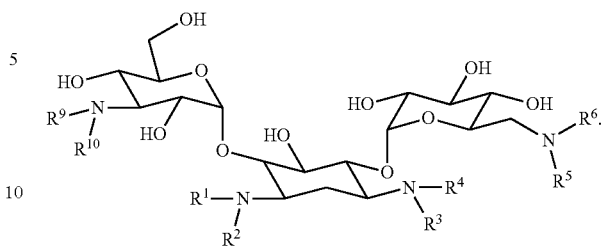

Formula II

In several embodiments, each of $R^1$, $R^2$, $R^3$, $R^4$, $R^5$, $R^6$, $R^9$, and $R^{10}$ is independently selected from —H or represents a covalent bond to one or more linking units. In several embodiments, the linking unit of the one or more linking units is represented by the following structure:

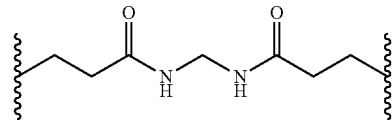 [SMILES: *CCC(=O)NCNC(=O)CC*]

and the linking unit of the one or more linking units forms a covalent bridge between the first aminoglycoside unit and a second aminoglycoside unit. In several embodiments, the aminoglycoside unit of the hyperbranched polyaminoglycoside is derived from kanamycin. In several embodiments, streptomycin, tobramycin, gentamicin, and/or neomycin can also be used as one or both of the aminoglycoside units.

In several embodiments, there are provided hyperbranched polyaminoglycosides that further include one or more terminal units. Depending on the embodiment, the one or more terminal units are selected from:

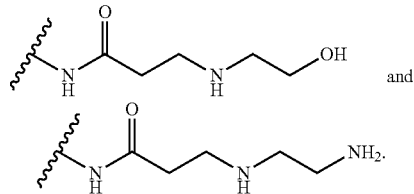

In several embodiments, there are provided hyperbranched polyaminoglycosides that further include one or more dendritic units. Depending on the embodiments, the one or more dendritic units are selected from:

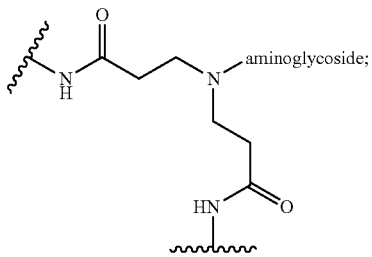

where "—N-aminoglycoside" represents the structure of Formula II.

In several embodiments, there are provided hyperbranched polyaminoglycosides that further include or more linear units selected from:

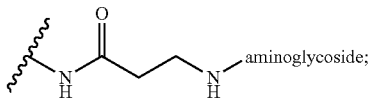

where "—N-aminoglycoside" represents the structure of Formula II.

In several embodiments, there are provided hyperbranched polyaminoglycosides wherein at least one secondary amine of the hyperbranched polyaminoglycoside comprises—a NO donor. In several embodiments, at least one secondary amine of the hyperbranched polyaminoglycoside comprises a N-diazeniumdiolate NO donor. In additional embodiments, the hyperbranched polyaminoglycoside has a weight average molecular weight of less than or equal to about 7 kDa. In several embodiments, the hyperbranched polyaminoglycoside has a number average molecular weight of less than or equal to about 4 kDa. In several embodiments, the hyperbranched polyaminoglycoside has a NO storage capacity of greater than or equal to 0.4 μmol NO/mg hyperbranched polyaminoglycoside. In several embodiments, the hyperbranched polyaminoglycoside provides greater than or equal to 90% (e.g., 90%, 95%, 97%, 98%, 99% or 100%) bacterial reduction of bacterial viability against one or more of *P. aeruginosa, S. aureus P. gingivalis, A. actinomycetemcomitans, A. viscosus,* and/or *S. mutans*. In several embodiments, such a reduction is achieved at a concentration of less than or equal to 2 mg/mL of the hyperbranched polyaminoglycoside.

Some embodiments pertain to a functionalized hyperbranched polyaminoglycoside. In some embodiments, the functionalized hyperbranched polyaminoglycoside comprises a first aminoglycoside unit comprising the structure of Formula II:

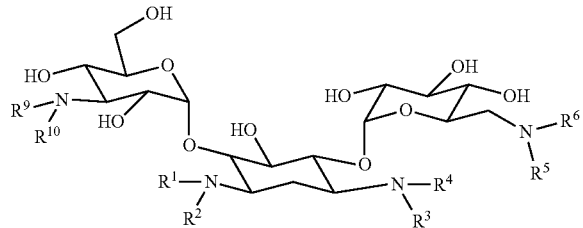

Formula II wherein each of $R^1$, $R^2$, $R^3$, $R^4$, $R^5$, $R^6$, $R^9$, and $R^{10}$ is independently selected from the —H or represents a covalent bond to one or more linking units; wherein a linking unit of the one or more linking units is represented by the following structure:

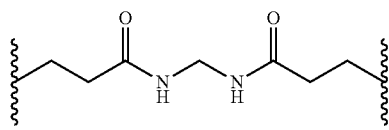 [SMILES: *CCC(=O)NCNC(=O)CC*]

wherein at least one linking unit forms a covalent bridge between the first aminoglycoside unit and a second aminoglycoside unit; and wherein at least one aminoglycoside unit of the hyperbranched polyaminoglycoside is derived from kanamycin.

In some embodiments, the kanamycin-based functionalized hyperbranched polyaminoglycoside additionally comprising one or more terminal units is selected from:

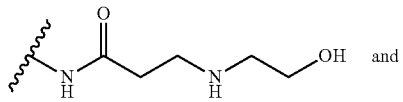

and

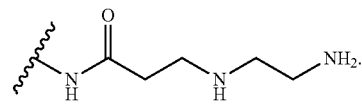

In some embodiments, the kanamycin-based functionalized hyperbranched polyaminoglycoside additionally comprises one or more dendritic units selected from:

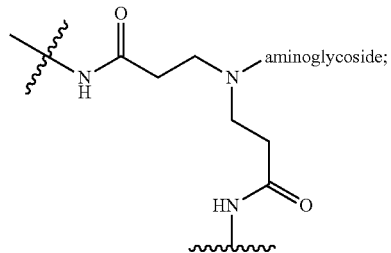

where "—N-aminoglycoside" represents the structure of Formula II.

In some embodiments, the kanamycin-based functionalized hyperbranched polyaminoglycoside additionally comprises one or more linear units selected from:

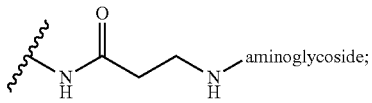

where "—N-aminoglycoside" represents the structure of Formula II.

In some embodiments of the kanamycin-based functionalized hyperbranched polyaminoglycosides, at least one secondary amine of the hyperbranched polyaminoglycoside comprises a N-diazeniumdiolate NO donor.

Some embodiments pertain to a functionalized hyperbranched polyaminoglycoside, comprising a first aminoglycoside unit comprising the structure of Formula III:

Formula III

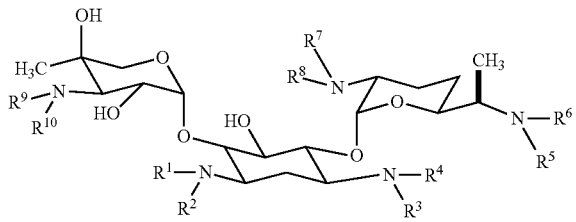

wherein each of $R^1$, $R^2$, $R^3$, $R^4$, $R^5$, $R^6$, $R^7$, $R^8$, $R^9$, and $R^{10}$ is independently selected from the —H or represents a covalent bond to one or more linking units; wherein a linking unit of the one or more linking units is represented by the following structure:

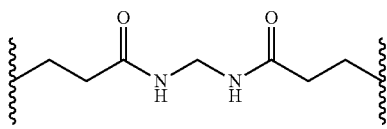 [SMILES: *CCC(=O)NCNC(=O)CC*]

wherein at least one linking unit forms a covalent bridge between the first aminoglycoside unit and a second aminoglycoside unit; and wherein at least one aminoglycoside unit of the hyperbranched polyaminoglycosides is derived from gentamicin.

In some embodiments, the gentamicin-based functionalized hyperbranched polyaminoglycoside additionally comprises one or more dendritic units selected from:

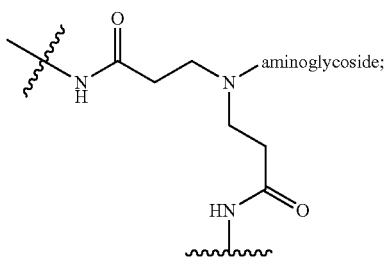

where "—N-aminoglycoside" represents the structure of Formula III.

In some embodiments, the gentamicin-based functionalized hyperbranched polyaminoglycoside additionally comprises one or more linear units selected from:

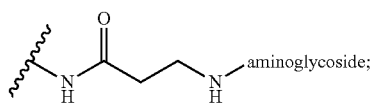

where "—N-aminoglycoside" represents the structure of Formula III.

In some embodiments, at least one secondary amine of the gentamicin-based hyperbranched polyaminoglycosides comprises a N-diazeniumdiolate NO donor.

Some embodiments pertain to a functionalized hyperbranched polyaminoglycoside, comprising a first aminoglycoside unit comprising a structure of Formula IV:

Formula IV

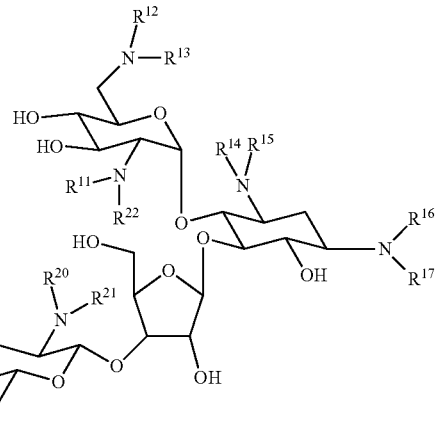

wherein each of $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ is independently selected from the —H or represents a covalent bond to one or more linking units; wherein a linking unit of the one or more linking units is represented by the following structure:

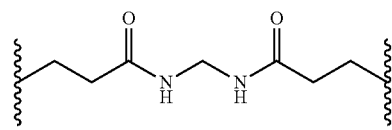 [SMILES: *CCC(=O)NCNC(=O)CC*]

wherein at least one linking unit forms a covalent bridge between the first aminoglycoside unit and a second aminoglycoside unit; and wherein at least one aminoglycoside unit of the hyperbranched polyaminoglycosides is derived from neomycin.

In some embodiments, the neomycin-based functionalized hyperbranched polyaminoglycoside additionally comprises one or more dendritic units selected from:

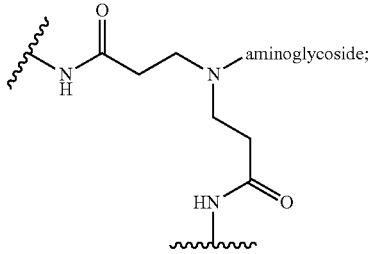

where "—N-aminoglycoside" represents the structure of Formula IV.

In some embodiments, the neomycin-based functionalized hyperbranched polyaminoglycoside additionally comprises one or more linear units selected from:

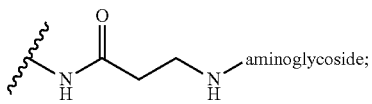

where "—N-aminoglycoside" represents the structure of formula IV.

In some embodiments of the neomycin-based functionalized hyperbranched polyaminoglycoside, at least one secondary amine of the hyperbranched polyaminoglycosides comprises a N-diazeniumdiolate NO donor.

In some embodiments, the kanamycin-based, neomycin-based, or gentamicin-based hyperbranched polyaminoglycoside has at least one secondary amine comprising a N-diazeniumdiolate NO donor.

In some embodiments, the kanamycin-based, neomycin-based, or gentamicin-based hyperbranched polyaminoglycoside has a number average molecular weight of less than or equal to about 4 kDa. In some embodiments, the hyperbranched polyaminoglycoside has a number average molecular weight in the range between about 1.6 to about 4.3 kDa.

In some embodiments, the kanamycin-based, neomycin-based, or gentamicin-based hyperbranched polyaminoglycoside has a weight average molecular weight of less than or equal to about 7 kDa. In some embodiments, the hyperbranched polyaminoglycoside has a weight average molecular weight in the range between about 2 to about 7 kDa.

In some embodiments, the kanamycin-based, neomycin-based, or gentamicin-based hyperbranched polyaminoglycoside has a NO storage capacity of greater than or equal to 0.4 μmol NO/mg hyperbranched polyaminoglycoside. In some embodiments, the hyperbranched polyaminoglycoside has a NO storage capacity in the range between about 0.4 to about 1.3 μmol NO/mg hyperbranched polyaminoglycoside, including ranges between about 0.4 to about 0.6 and about 1.2 to about 1.3 μmol NO/mg hyperbranched polyaminoglycoside.

In some embodiments, the kanamycin-based, neomycin-based, or gentamicin-based hyperbranched polyaminoglycoside provides greater than or equal to 99% bacterial reduction in a bacterial viability assay performed under static conditions over 2 hours against one or more of *P. aeruginosa, S. aureus P. gingivalis, A. actinomycetemcomitans, A. viscosus*, and/or *S. mutans* at a concentration of less than or equal to 2 mg/mL.

In some embodiments, the functionalized hyperbranched polyaminoglycosides comprises a first aminoglycoside comprising Formula I:

Formula I

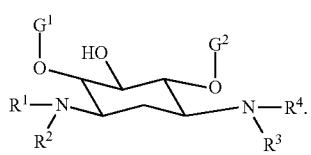

In some embodiments, $G^1$ is selected from the group consisting of:

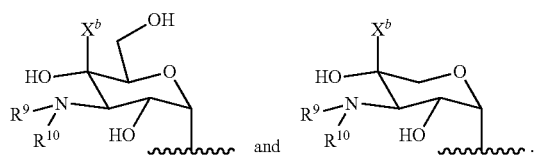

In some embodiments, $G^2$ is selected from the group consisting of:

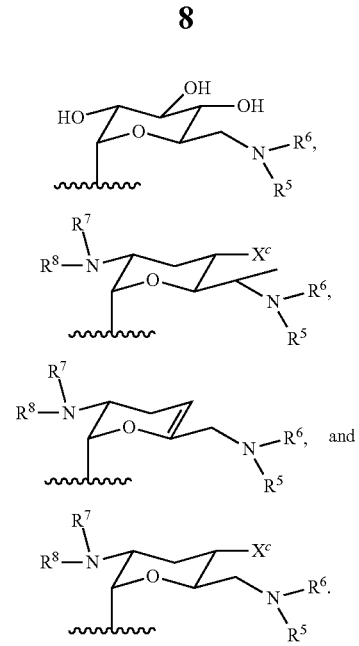

In some embodiments, $R^1$, $R^2$, $R^3$, $R^4$, $R^5$, $R^6$, $R^7$, $R^8$, $R^9$, and $R^{10}$ are independently selected from —H, optionally substituted $C_1$-$C_6$ alkyl, optionally substituted polyamino having 1 to 6 repeat units with intervening $C_1$-$C_6$ alkyl groups, optionally substituted polyether having 1 to 6 repeat units with intervening $C_1$-$C_6$ alkyl groups, or a covalent bond to a linking unit.

In some embodiments, at least one of $R^1$, $R^2$, $R^3$, $R^4$, $R^5$, $R^6$, $R^7$, $R^8$, $R^9$, and $R^{10}$ is covalent bond to one or more linking units selected from the following:

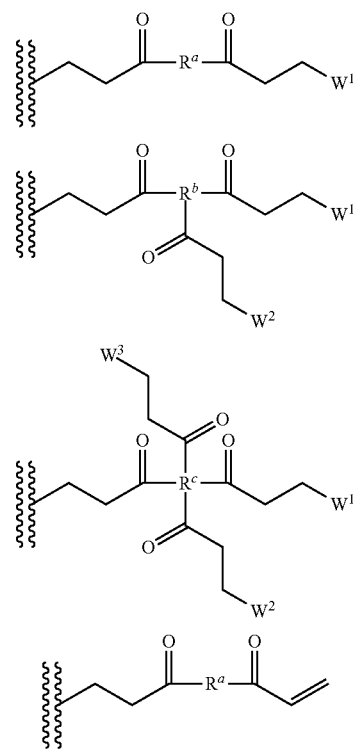

-continued

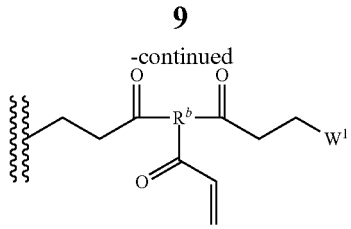

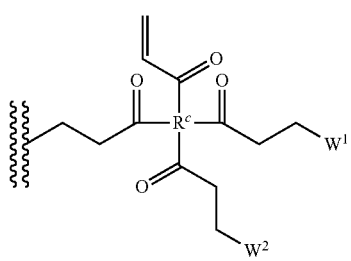

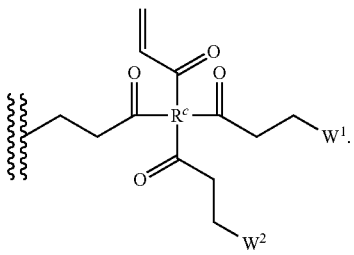

In some embodiments, "⸘" indicates an attachment to the first aminoglycoside. In some embodiments, $W^1$, $W^2$, or $W^3$, where present, are independently selected from one or more additional aminoglycosides, one or more end-capping substituents and at least one linking unit that provides a covalent bridge from the first aminoglycoside to a second aminoglycoside. In some embodiments, $R^a$, $R^b$, and $R^c$ are independently selected from optionally substituted $C_1$-$C_6$ alkyl, optionally substituted polyamino having 1 to 6 repeat units (with $C_1$-$C_6$ alkyl(s)), and/or optionally substituted polyether having 1 to 6 repeat units (with $C_1$-$C_6$ alkyl(s)).

In some embodiments, the one or more end-capping substituents, where present, independently have a formula of —NH—$((CH_2)_a X^1)_b$—$(CH_2)_c$H where of $X^1$ is O or NH and a, b, and c are independently an integer from 0 to 10.

In some embodiments, the hyperbranched polyaminoglycoside comprises the structure of Formula II:

Formula II

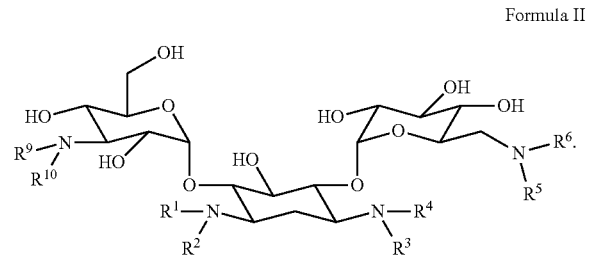

wherein the variables are as described elsewhere herein.

In some embodiments, the hyperbranched polyaminoglycoside comprises the structure of Formula III:

Formula III

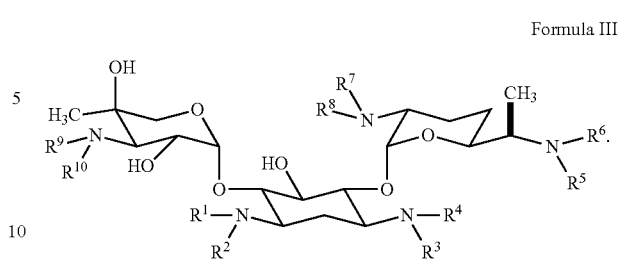

wherein the variables are as described elsewhere herein.

Some embodiments pertain to a hyperbranched polyaminoglycoside comprising a first aminoglycoside with the structure of Formula IV:

Formula IV

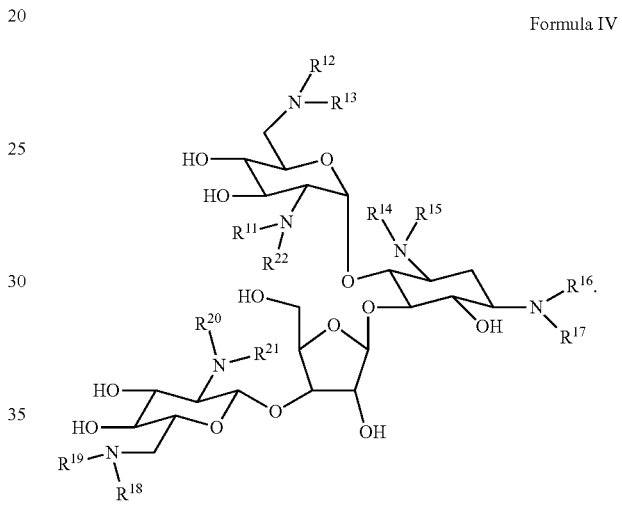

In some embodiments, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently selected from —H, optionally substituted $C_1$-$C_6$ alkyl, optionally substituted polyamino having 1 to 6 repeat units with intervening $C_1$-$C_6$ alkyl groups, optionally substituted polyether having 1 to 6 repeat units with intervening $C_1$-$C_6$ alkyl groups, and a covalent bond to a linking unit. In some embodiments, at least one of $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ is a covalent bond to one or more linking units selected from the following:

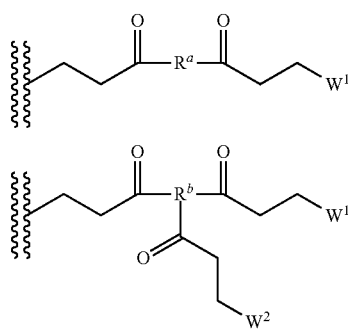

-continued

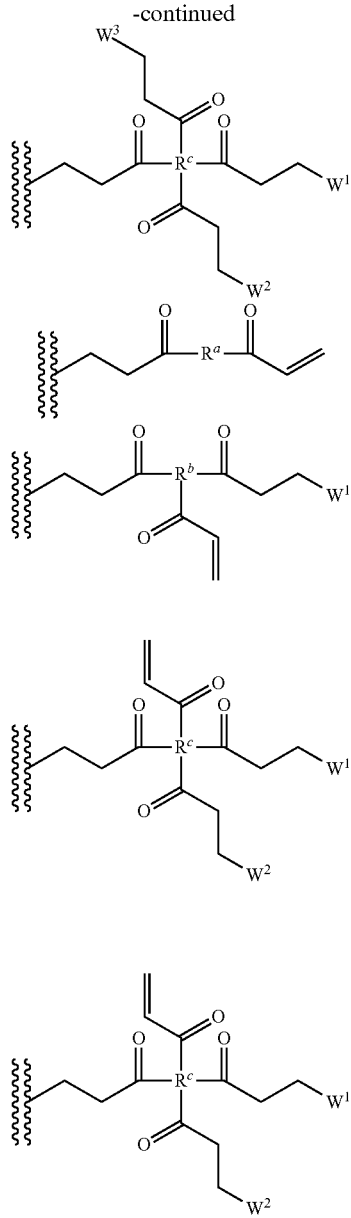

wherein "⧝" indicates an attachment to the first aminoglycoside. In some embodiments, $W^1$, $W^2$, or $W^3$, where present, are independently selected from one or more additional aminoglycosides, one or more end-capping substituents and at least one linking unit that provides a covalent bridge from the first aminoglycoside to a second aminoglycoside. In some embodiments, $R^a$, $R^b$, and $R^c$ are independently selected from optionally substituted $C_1$-$C_6$ alkyl, optionally substituted polyamino having 1 to 6 repeat units (with $C_1$-$C_6$ alkyl(s)), and/or optionally substituted polyether having 1 to 6 repeat units (with $C_1$-$C_6$ alkyl(s)). In some embodiments, the one or more end-capping substituents, where present, independently have a formula of —NH—$((CH_2)_a X^1)_b$—$(CH_2)_c$H where of $X^1$ is O or NH and a, b, and c are independently an integer from 0 to 10.

Some embodiments pertain to a hyperbranched polyaminoglycoside comprising a first aminoglycoside with the structure of Formula V:

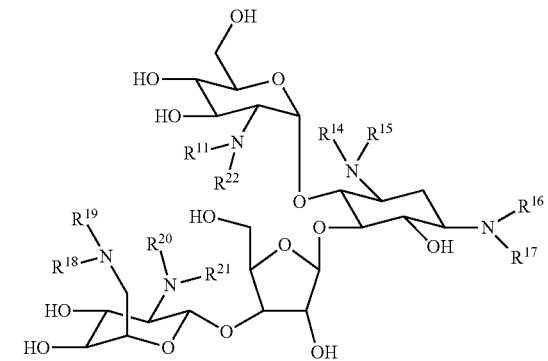

Formula V

In some embodiments, $R^{11}$, $R^{14}$, $R^{15}$, $R^{16}$, $R^{17}$, $R^{18}$, $R^{19}$, $R^{20}$, $R^{21}$, and $R^{22}$ are independently selected from —H, optionally substituted $C_1$-$C_6$ alkyl, optionally substituted polyamino having 1 to 6 repeat units with intervening $C_1$-$C_6$ alkyl groups, optionally substituted polyether having 1 to 6 repeat units with intervening $C_1$-$C_6$ alkyl groups, or a covalent bond to a linking unit. In some embodiments, at least one of $R^{11}$, $R^{14}$, $R^{15}$, $R^{16}$, $R^{17}$, $R^{18}$, $R^{19}$, $R^{20}$, $R^{21}$, and $R^{22}$ is a covalent bond to one or more linking units selected from the following:

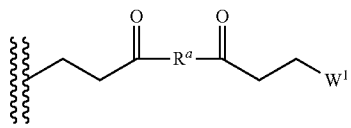

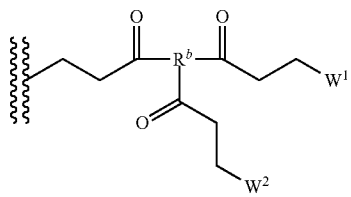

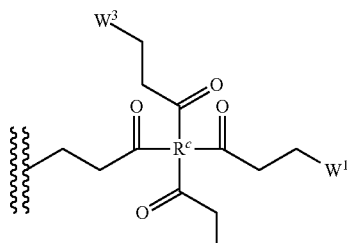

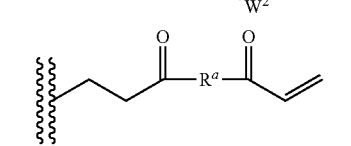

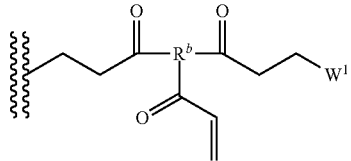

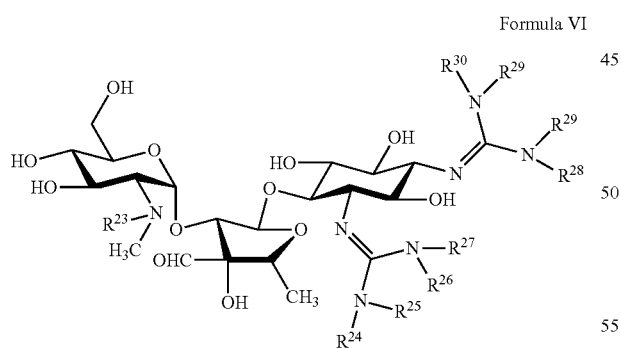

In some embodiments, "⸹⸹" indicates an attachment to the first aminoglycoside. In some embodiments, $W^1$, $W^2$, or $W^3$, where present, are independently selected from one or more additional aminoglycosides, one or more end-capping substituents, and at least one linking unit that provides a covalent bridge from the first aminoglycoside to a second aminoglycoside. In some embodiments, $R^a$, $R^b$, and $R^c$ are independently selected from optionally substituted $C_1$-$C_6$alkyl, optionally substituted polyamino having 1 to 6 repeat units (with $C_1$-$C_6$ alkyl(s)), and/or optionally substituted polyether having 1 to 6 repeat units (with $C_1$-$C_6$ alkyl(s)).

In some embodiments, the one or more end-capping substituents, where present, independently have a formula of —NH—$((CH_2)_a X^1)_b$—$(CH_2)H$ where of $X^1$ is O or NH and a, b, and c are independently an integer from 0 to 10.

Some embodiments pertain to a hyperbranched polyaminoglycoside, comprising a first aminoglycoside of Formula VI:

Formula VI

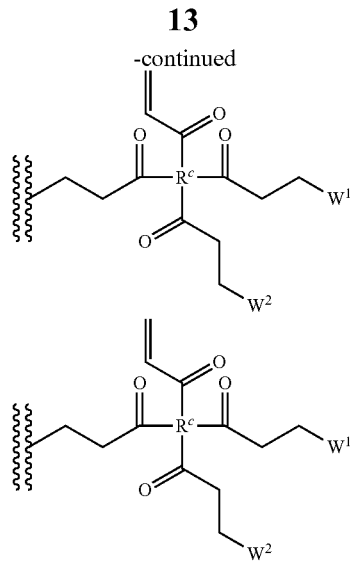

In some embodiments, $R^{23}$, $R^{24}$, $R^{25}$, $R^{26}$, $R^{27}$, $R^{28}$, $R^{29}$, and $R^{30}$ are independently selected from —H, optionally substituted $C_1$-$C_6$ alkyl, optionally substituted polyamino having 1 to 6 repeat units with intervening $C_1$-$C_6$ alkyl groups, optionally substituted polyether having 1 to 6 repeat units with intervening $C_1$-$C_6$ alkyl groups, or a covalent bond to a linking unit.

In some embodiments, at least one of $R^{23}$, $R^{24}$, $R^{25}$, $R^{26}$, $R^{27}$, $R^{28}$, $R^{29}$, and $R^{30}$ is a covalent bond to one or more linking unit selected from the following:

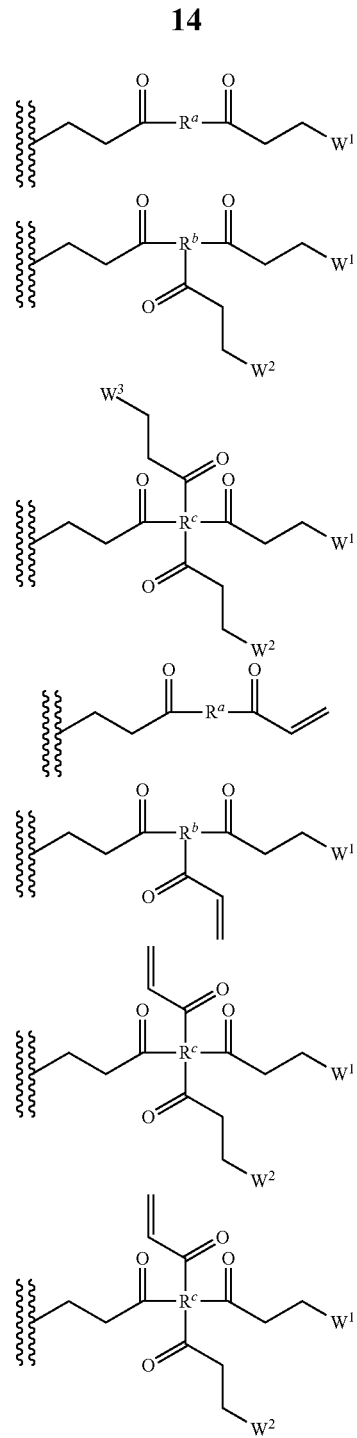

In some embodiments, "⸹⸹" indicates an attachment to the first aminoglycoside. In some embodiments, $W^1$, $W^2$, or $W^3$, where present, are independently selected from one or more additional aminoglycosides, one or more end-capping substituents, and at least one linking unit provides a covalent bridge from the first aminoglycoside to a second aminoglycoside.

In some embodiments, $R^a$, $R^b$, and $R^c$ are independently selected from optionally substituted $C_1$-$C_6$alkyl, optionally substituted polyamino having 1 to 6 repeat units (with $C_1$-$C_6$ alkyl(s)), and/or optionally substituted polyether having 1 to 6 repeat units (with $C_1$-$C_6$ alkyl(s))

In some embodiments, the one or more end-capping substituents, where present, independently have a formula of —NH—((CH$_2$)$_a$X$^1$)$_b$—(CH$_2$)$_c$H where of X$^1$ is O or NH and a, b, and c are independently an integer from 0 to 10.

Some embodiments pertain to a hyperbranched polyaminoglycoside, comprising an aminoglycoside of Formula VII:

Formula VII

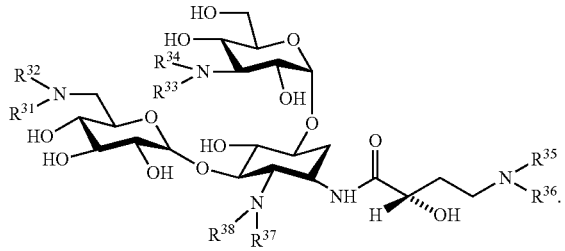

In some embodiments, R$^{31}$, R$^{32}$, R$^{33}$, R$^{34}$, R$^{35}$, R$^{36}$, R$^{37}$, and R$^{38}$ are independently selected from the group consisting of —H, optionally substituted C$_1$-C$_6$ alkyl, optionally substituted polyamino having 1 to 6 repeat units with intervening C$_1$-C$_6$ alkyl groups, optionally substituted polyether having 1 to 6 repeat units with intervening C$_1$-C$_6$ alkyl groups, and a covalent bond to a linking unit.

In some embodiments, at least one of R$^{31}$, R$^{32}$, R$^{33}$, R$^{34}$, R$^{35}$, R$^{36}$, R$^{37}$, and R$^{38}$ a covalent bond to one or more linking unit selected from the following:

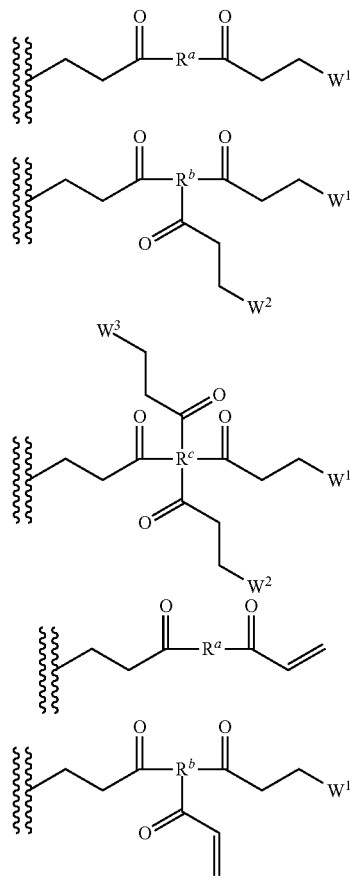

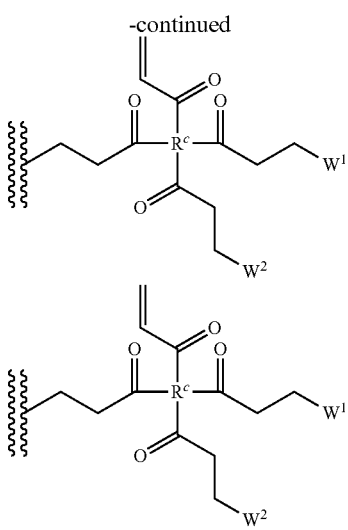

In some embodiments, "⸾" indicates an attachment to the first aminoglycoside. In some embodiments, W$^1$, W$^2$, or W$^3$, where present, are independently selected from one or more additional aminoglycosides, one or more end-capping substituents, and at least one linking unit that provides a covalent bridge from the first aminoglycoside to a second aminoglycoside.

In some embodiments, R$^a$, R$^b$, and R$^c$ are independently selected from optionally substituted C$_1$-C$_6$alkyl, optionally substituted polyamino having 1 to 6 repeat units (with C$_1$-C$_6$ alkyl(s)), and/or optionally substituted polyether having 1 to 6 repeat units (with C$_1$-C$_6$ alkyl(s)).

In some embodiments, the one or more end-capping substituents, where present, independently have a formula of —NH—((CH$_2$)$_a$X$^1$)$_b$—(CH$_2$)$_c$H where of X$^1$ is O or NH and a, b, and c are independently an integer from 0 to 10.

In some embodiments, the hyperbranched polyaminoglycoside comprises multiple different aminoglycosides, for example, units of Formulae I, II, III, IV, V, VI, VII, and combinations thereof. In some embodiments, the hyperbranched polyaminoglycoside comprises kanamycin-based units, amikacin-based units, tobramycin-based units, dibekacin-based units, gentamicin-based units, sisomicin-based units, netilmicin-based units, neomycin-based units (neomycin B and/or C), paramomycin-based units (neomycin E), streptomycin-based units, and combinations thereof.

Any of the embodiments described above, or described elsewhere herein, can include one or more of the following features.

In some embodiments, the hyperbranched polyaminoglycoside further comprises a NO-donating group. In some embodiments, the NO donating group is selected from the group consisting of:

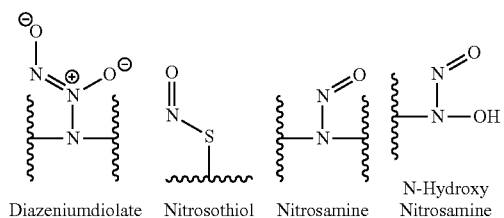

Diazeniumdiolate  Nitrosothiol  Nitrosamine  N-Hydroxy Nitrosamine

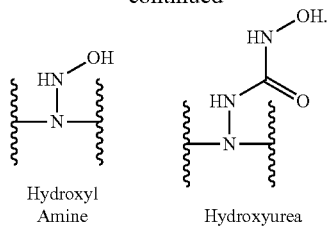

Hydroxyl Amine          Hydroxyurea where "⌇" indicates attachment to other atoms within the hyperbranched aminoglycoside. In some embodiments, the NO donating group is a diazeniumdiolate.

In some embodiments, the linking unit is:

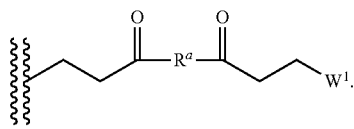

In some embodiments, the $R^a$ is —NH—CH$_2$—NH—. In some embodiments, the $W^1$ is the second aminoglycoside.

In some embodiments, any one of $R^1$ to $R^{38}$ are independently selected from the group consisting of —H, or a covalent bond to a linking unit.

In some embodiments, the end-capping substituents, where present, are —NHCH$_2$CH$_2$NH$_2$ or —NHCH$_2$CH$_2$OH.

Some embodiments pertain to a method for preparing the hyperbranched polyaminoglycosides described above or elsewhere herein. In some embodiments, the method comprises contacting the first aminoglycoside with a multifunctional polymerizing agent and one or more additional aminoglycosides to form a hyperbranched polyaminoglycoside.

In some embodiments, the method comprises adding an end-capping agent to the hyperbranched polyaminoglycoside to covalently cap any unreacted functionalities on the polymerizing agent.

In some embodiments, the method comprises exposing the hyperbranched polyaminoglycoside to NO to provide a NO-donating hyperbranched polyaminoglycoside.

In some embodiments, the NO exposing step is carried out in alkaline conditions.

In some embodiments of the method, the polymerizing agent comprises a bifunctional, trifunctional, or tetrafunctional molecule. In some embodiments of the method, the polymerizing agent comprises a Michael acceptor. In some embodiments of the method, the polymerizing agent comprises a diacrylate, a triacrylate, or a tetraacrylate.

In some embodiments of the method, polymerizing agent comprises one or more of N,N'-methylenebis(acrylamide), ethylene glycol diacrylate, propane diol diacrylate, butandiol diacrylate, trimethylolpropane triacrylate, pentaerythritol triacrylate, pentaerythritol triacrylate, glycerol propoxylate (1PO/OH) triacrylate, or trimethylolpropane propoxylate triacrylate.

In some embodiments of the method, polymerizing agent comprises one or more of the following structures:

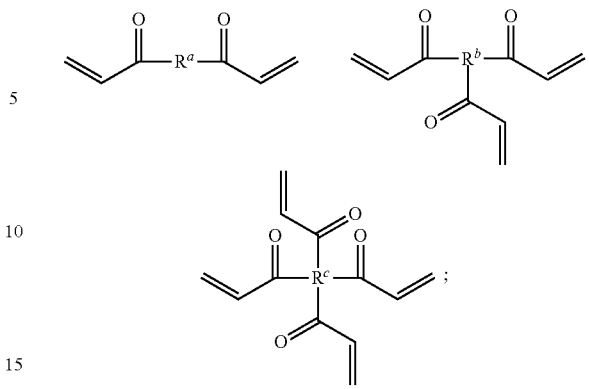

wherein $R^a$, $R^b$, and $R^c$ are independently selected from optionally substituted $C_1$-$C_6$alkyl, optionally substituted polyamino having 1 to 6 repeat units (with $C_1$-$C_6$ alkyl(s)), and/or optionally substituted polyether having 1 to 6 repeat units (with $C_1$-$C_6$ alkyl(s)).

In some embodiments of the method, the polymerizing agent is N,N'-methylenebis(acrylamide).

In some embodiments of the method, the end-capping agent comprises one or more of H$_2$N—((CH$_2$)$_a$NH)$_b$—H, H$_2$N—((CH$_2$)$_a$NH)$_b$—(CH$_2$)$_c$H, H$_2$N—((CH$_2$)$_a$X$^1$)$_b$—(CH$_2$)$_c$H, and HX$^1$—((CH$_2$)$_a$X$^2$)$_b$((CH$_2$)$_c$X$^3$)$_d$—(CH$_2$)$_e$H. In some embodiments of the method, each instance of a, b, c, d, or e is independently selected from an integer from 0 to 10. In some embodiments of the method, each instance of $X^1$, $X^2$, and $X^3$ is independently selected from O, S, or NH. In some embodiments of the method, the end-capping agent comprises H$_2$NCH$_2$CH$_2$NH$_2$ and/or H$_2$NCH$_2$CH$_2$OH.

Some embodiments pertain to a method of decreasing microbial contamination. In some embodiments of the method, the method comprises contacting a surface contaminated with a plurality of microbes with a compound comprising a nitric oxide releasing hyperbranched polyaminoglycoside, the hyperbranched polyaminoglycoside comprising an amine-containing group covalently bound to a nitric oxide donor. In some embodiments of the method, the nitric oxide donor generates nitric oxide and induces damage to the membrane and/or DNA of the microbes, thereby reducing the number of viable microbes.

In some embodiments, the plurality of microbes comprises one or more of viruses, gram positive bacteria, gram negative bacteria, drug resistant bacteria, molds, yeasts, fungi, and combinations thereof.

In several embodiments, the surface comprises an organic surface. In some embodiments of the method, the surface is human skin or animal skin. In some embodiments of the method, the surface is in the mouth, or surrounding tissues (e.g., lips, nasal nares, teeth, gums, etc.). In several embodiments, the surface comprises the oral mucosa. Advantageously, in some embodiments of the method, the application step does not induce skin or tissue irritation.

In some embodiments, the surface comprises an inorganic surface. In some embodiments of the method, the inorganic surface is an external or internal surface of a medical device. In some embodiments, the device is a dental device, including, but not limited to, dental tools, dental implants, dental fixtures, etc.

In some embodiments, the microbial load comprises drug-resistant bacteria. In some embodiments of the method, the microbial load comprises one or more dental pathogens. In some embodiments, the microbial load comprises one or more of *P. aeruginosa, S. aureus P. gingivalis, A. actinomycetemcomitans, A. viscosus*, and/or *S. mutans*.

In several embodiments of the method, the hyperbranched polyaminoglycoside is as described above or elsewhere herein.

Some embodiments pertain to a method of treating and/or preventing dental caries. In several embodiments, the method comprises contacting the surface of a patient's mouth that is contaminated with one or more dental pathogens with a compound comprising a nitric oxide releasing hyperbranched polyaminoglycoside, the hyperbranched polyaminoglycoside comprising an amine-containing group covalently bound to a nitric oxide donor. In some embodiments of the method, the nitric oxide donor generates nitric oxide and induces damage to the membrane and/or DNA of the pathogens, thereby reducing the number of viable pathogens, and consequently reducing formation or progression of dental caries. In some embodiments of the method, the microbial load comprises one or more of *P. aeruginosa, S. aureus P. gingivalis, A. actinomycetemcomitans, A. viscosus*, and/or *S. mutans*. In some embodiments of the method, the hyperbranched polyaminoglycoside is as described above or elsewhere herein.

Some embodiments pertain to the use of a compound in the preparation of a medicament for decreasing microbial contamination. In some embodiments, the compound comprises a nitric oxide releasing hyperbranched polyaminoglycosides. In some embodiments, the hyperbranched polyaminoglycoside comprises an amine-containing group covalently bound to a nitric oxide donor. In some embodiments the nitric oxide donor generates nitric oxide and induces damage to the membrane and/or DNA of the microbes, thereby reducing the number of viable microbes. In some embodiments, the compound is formulated to treat a plurality of microbes comprising one or more of viruses, gram positive bacteria, gram negative bacteria, drug resistant bacteria, molds, yeasts, fungi, and combinations thereof. In some embodiments, the compound is formulated to be delivered to an organic surface. In some embodiments, the compound is formulated to be delivered to human skin or animal skin. In some embodiments, the surface is in the mouth. In some embodiments, the compound is formulated to be delivered to an inorganic surface. In some embodiments, the surface is an external or internal surface of a medical device. In some embodiments, the device is a dental device. In some embodiments, the hyperbranched polyaminoglycoside is as disclosed above or elsewhere herein.

Some embodiments pertain to a compound comprising a nitric oxide releasing hyperbranched polyaminoglycoside, the hyperbranched polyaminoglycoside comprising an amine-containing group covalently bound to a nitric oxide donor; wherein the nitric oxide donor generates nitric oxide and induces damage to the membrane and/or DNA of the microbes, thereby reducing the number of viable microbes.

BRIEF DESCRIPTION OF THE DRAWINGS

FIGS. 4A-4E show FTIR spectra for hyperbranched polyaminoglycosides: A) HPKA; B) HPNE; C) HPGE; D) HPKA-EDA; and E) HPKA-MEA.

FIGS. 5A-5E show quantitative $^{13}$C NMR spectra for hyperbranched polyaminoglycosides: A) HPKA; B) HPNE; C) HPGE; D) HPKA-EDA; and E) HPKA-MEA.

DETAILED DESCRIPTION

General

Figure 1:
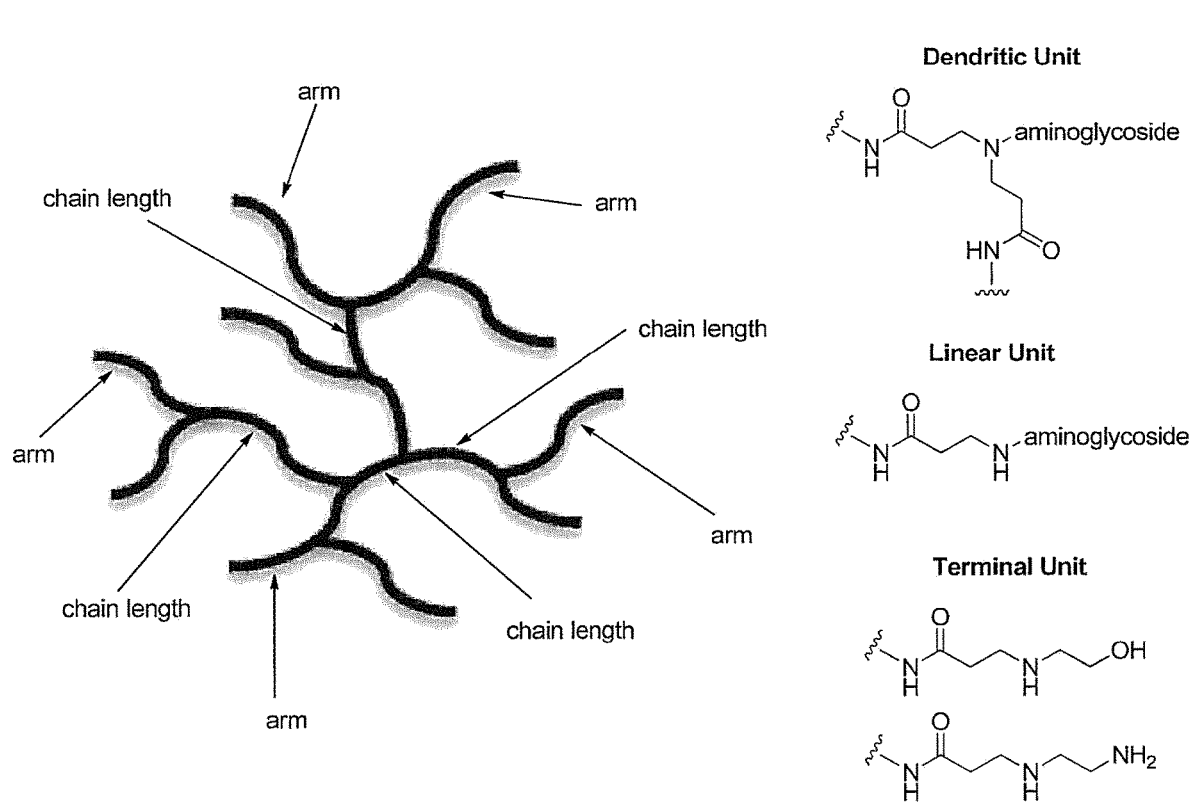
FIG. 1 is a representation of an embodiment of a hyperbranched polyaminoglycoside structure.

Aminoglycosides are polyamines that can be used as antimicrobial agents. Some embodiments described herein pertain to polyaminoglycosides for use as antimicrobial agents. In some embodiments, the polyaminoglycosides disclosed herein are functionalized with nitric oxide (NO) binding moieties and can be used as a platform for NO generation/release. In some embodiments, the polyaminoglycosides are hyperbranched. Certain embodiments disclosed herein pertain to hyperbranched polyaminoglycosides with bactericidal and/or antimicrobial activity. In some embodiments, the hyperbranched polyaminoglycosides comprise NO binding moieties. In some embodiments, the hyperbranched polyaminoglycosides can be reacted with nitric oxide (NO) gas or some other NO donor to yield NO-donating hyperbranched polyaminoglycosides. In some embodiments, the hyperbranched polyaminoglycosides are biodegradable and/or biocompatible. While hyperbranched polyaminoglycosides are used as exemplary structures herein, it should be appreciated that linear polyaminoglycosides (e.g., non-hyperbranched) are also used, according to several embodiments.

Unless otherwise defined, all technical and scientific terms used herein have the same meaning as commonly understood by one of ordinary skill in the art to which this subject matter belongs. The terminology used in the description of the subject matter herein is for the purpose of describing particular embodiments only and is not intended to be limiting of the subject matter.

As used herein, "and/or" refers to and encompasses any and all possible combinations of one or more of the associated listed items, as well as the lack of combinations when interpreted in the alternative ("or").

As used herein, the term "about," when referring to a measurable value such as an amount of a compound or agent of the current subject matter, dose, time, temperature, bactericidal efficacy, and the like, is meant to encompass variations of ±20%, ±10%, ±5%, ±1%, ±0.5%, or even ±0.1% of the specified amount.

The term "effective amount," as used herein, refers to that amount of a recited compound that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art.

For example, an effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In some embodiments, an improvement in a condition can be a reduction in infection. In some embodiments, an improvement can be reduction of bacterial load (e.g., bioburden) on a surface or in a subject. Actual dosage levels of active ingredients in an active composition of the presently disclosed subject matter can be varied so as to administer an amount of the active compound(s) that is effective to achieve the desired response for a particular subject and/or application. The selected dosage level will depend upon a variety of factors including, but not limited to, the activity of the composition, formulation, route of administration, combination with other drugs or treatments, severity of the condition being treated, and the physical condition and prior medical history of the subject being treated. In some embodiments, a minimal dose is administered, and dose is escalated in the absence of dose-limiting toxicity to a minimally effective amount. Determination and adjustment of an effective dose, as well as evaluation of when and how to make such adjustments, are contemplated herein.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, and/or change in clinical parameters, disease or illness, curing the illness, etc.

The terms "nitric oxide donor" or "NO donor" refer to species and/or molecules that donate, release and/or directly or indirectly transfer a nitric oxide species, and/or stimulate the endogenous production of nitric oxide in vivo and/or elevate endogenous levels of nitric oxide in vivo such that the biological activity of the nitric oxide species is expressed at the intended site of action.

The term "nitric oxide releasing" refers to species that donate, release and/or directly or indirectly transfer any one (or two or more) of the three redox forms of nitrogen monoxide (NO+, NO−, NO) and/or methods of donating, releasing and/or directly or indirectly transferring any one (or two or more) of the three redox forms of nitrogen monoxide (NO+, NO−, NO). In some embodiments, the nitric oxide releasing is accomplished such that the biological activity of the nitrogen monoxide species is expressed at the intended site of action.

The term "microbial infection" as used herein refers to bacterial, fungal, viral, yeast infections, as well other microorganisms, and combinations thereof.

The "patient" or "subject" treated as disclosed herein is, in some embodiments, a human patient, although it is to be understood that the principles of the presently disclosed subject matter indicate that the presently disclosed subject matter is effective with respect to all vertebrate species, including mammals, which are intended to be included in the terms "subject" and "patient." Suitable subjects are generally mammalian subjects. The subject matter described herein finds use in research as well as veterinary and medical applications. The term "mammal" as used herein includes, but is not limited to, humans, non-human primates, cattle, sheep, goats, pigs, horses, cats, dog, rabbits, rodents (e.g., rats or mice), monkeys, etc. Human subjects include neonates, infants, juveniles, adults and geriatric subjects.

As used herein, the term "functionalized hyperbranched polyaminoglycoside" refers to a hyperbranched polyaminoglycoside material which contains one or more modified units (e.g., covalently end-capped with non-aminoglycoside moieties). Such "functionalized hyperbranched polyaminoglycosides" may or may not have a nitric oxide donor moiety attached.

The term "amino" and "amine" refer to nitrogen-containing groups such as $NR_3$, $NH_3$, $NHR_2$, and $NH_2R$, wherein R can be as described elsewhere herein. Thus, "amino" as used herein can refer to a primary amine, a secondary amine, or a tertiary amine. In some embodiments, one R of an amino group can be a diazeniumdiolate (i.e., NONO).

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), cycloalkyl (alkyl), heteroaryl(alkyl), heterocyclyl(alkyl), hydroxy, alkoxy, acyl, cyano, halogen, thiocarbonyl, O-carbamyl, N-carbamyl, C-amido, N-amido, S-sulfonamido, N-sulfonamido, C-carboxy, O-carboxy, haloalkyl, haloalkoxy, an amino, a mono-substituted amine group, a di-substituted amine group, a mono-substituted amine(alkyl), a di-substituted amine(alkyl), a diamino-group, a diether-, a polyamino-, and a polyether-.

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1, 2, 3, 4, 5, 6, 7, 8, 9, 10, etc., up to and including 30 carbon atoms, although the present definition also covers the occurrence of the term "alkyl" where no numerical range is designated). The alkyl group may also be a medium size alkyl having 1 to 12 carbon atoms. The alkyl group could also be a lower alkyl having 1 to 6 carbon atoms. An alkyl group may be substituted or unsubstituted. By way of example only, "$C_1$-$C_5$ alkyl" indicates that there are one to five carbon atoms in the alkyl chain, i.e., the alkyl chain is selected from methyl, ethyl, n-propyl, isopropyl, n-butyl, isobutyl, tert-butyl, pentyl (branched and straight-chained), etc. Typical alkyl groups include, but are in no way limited to, methyl, ethyl, propyl, isopropyl, butyl, isobutyl, tertiary butyl, pentyl and hexyl.

As used herein, the term "alkylene" refers to a bivalent fully saturated straight chain aliphatic hydrocarbon group. Examples of alkylene groups include, but are not limited to, methylene, ethylene, propylene, butylene, pentylene, hexylene, heptylene and octylene. An alkylene group may be represented by 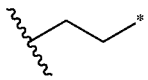, followed by the number of carbon atoms, followed by a "*". For example,

to represent ethylene. The alkylene group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkylene" where no numerical range is designated). The alkylene group may also be a medium size alkyl having 1 to 12 carbon atoms. The alkylene group could also be a lower alkyl having 1 to 4 carbon atoms. An alkylene group may be substituted or unsubstituted. For example, a lower alkylene group can be substituted by replacing one or more hydrogen of the lower alkylene group and/or by substituting both hydrogens on the same carbon with a $C_{3-6}$ monocyclic cycloalkyl group (e.g., 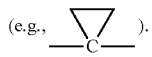).

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic (such as bicyclic) hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Examples of mono-cycloalkyl groups include, but are in no way limited to, cyclopropyl, cyclobutyl, cyclopentyl, cyclohexyl, cycloheptyl and cyclooctyl. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, adamantanyl and norbornanyl; and examples of spiro cycloalkyl groups include spiro[3.3]heptane and spiro[4.5]decane.

As used herein, "cycloalkenyl" refers to a mono- or multi-cyclic (such as bicyclic) hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s), 3 to 8 atoms in the ring(s) or 3 to 6 atoms in the ring(s). When composed of two or more rings, the rings may be connected together in a fused, bridged or spiro fashion. A cycloalkenyl group may be unsubstituted or substituted.

As used herein, "aryl" refers to a carbocyclic (all carbon) monocyclic or multicyclic (such as bicyclic) aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic (such as bicyclic) aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates.

When composed of two or more rings, the rings may be joined together in a fused, bridged or spiro fashion. As used herein, the term "fused" refers to two rings which have two atoms and one bond in common. As used herein, the term "bridged heterocyclyl" or "bridged heteroalicyclyl" refers to compounds wherein the heterocyclyl or heteroalicyclyl contains a linkage of one or more atoms connecting non-adjacent atoms. As used herein, the term "spiro" refers to two rings which have one atom in common and the two rings are not linked by a bridge. Heterocyclyl and heteroalicyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-azaspiro[3.4]octane and 2-azaspiro[3.4]octane.

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl and imidazolylalkyl and their benzo-fused analogs.

A "heteroalicyclyl(alkyl)" and "heterocyclyl(alkyl)" refer to a heterocyclic or a heteroalicyclic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl) and 1,3-thiazinan-4-yl(methyl).

As used herein, the term "hydroxy" refers to a —OH group.

As used herein, "alkoxy" refers to the Formula —OR wherein R is an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include formyl, acetyl, propanoyl, benzoyl and acryl. An acyl may be substituted or unsubstituted.

The term "halogen atom" or "halogen" as used herein, means any one of the radio-stable atoms of column 7 of the Periodic Table of the Elements, such as, fluorine, chlorine, bromine and iodine.

As used herein, the term "diamino-" denotes an a "—$NR_A$ $(R_B)N(R_C)$—" group in which $R_B$ and $R_C$ can be independently a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein, and wherein $R_A$ connects the two amino groups and can be (independently of $R_B$ and $R_C$) an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). $R_A$, $R_B$, and $R_C$ can independently be substituted or unsubstituted.

As used herein, the term "diether-" denotes an a "—$OR_DO$—" group in which $R_D$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein, and wherein $R_D$ connects the two O groups. $R_D$ can be optionally substituted or unsubstituted.

As used herein, the term "polyamino" denotes a repeating —$N(R_B)$alkyl-group. For illustration, the term polyamino can comprise —$N(R_B)$alkyl-$N(R_B)$alkyl-$N(R_B)$alkyl-$N(R_B)$ alkyl-. In some embodiments, the alkyl of the polyamino is as disclosed elsewhere herein. While this example has only 4 repeat units, the term "polyamino" may consist of 1, 2, 3, 4, 5, 6, 7, 8, 9, or 10 repeat units, where $R_B$ and alkyl are as defined elsewhere herein.

As noted here, the polyamino comprises amine groups with intervening alkyl groups (where alkyl is as defined elsewhere herein). A polyamino may terminate with an amine group or as an alkyl where the polyamino is a terminal group, or with as an —$N(R_C)$— where the polyamino bridges two atoms. For instance, any one of methylenediamino (—$NHCH_2NH$—), ethylenediamino (—$NH(CH_2)_2NH$—), etc. are considered a polyamino groups.

As used herein, the term "polyether" denotes a repeating —Oalkyl-group. For illustration, the term polyether can comprise —O-alkyl-O-alkyl —O-alkyl-O-alkyl. A polyether may have up to 10 repeat units, comprising —O— (ethers) with intervening alkyl groups (where alkyl is as defined elsewhere herein). The polyether may terminate with a hydroxy group or as an alkyl where the polyether is a terminal group, or with an —O— where the polyether bridges two atoms.

When a range of integers is given, the range includes any number falling within the range and the numbers defining ends of the range. For example, when the terms "integer from 1 to 20" is used, the integers included in the range are 1, 2, 3, 4, 5, 6, 7, 8, 9, 10, etc., up to and including 20.

Nitric Oxide

Nitric oxide (NO) is a broad-spectrum antibacterial agent capable of eradicating both bacteria and biofilms, primarily through the formation of reactive NO byproducts (e.g., peroxynitrite and dinitrogen trioxide) that cause oxidative and nitrosative damage to microbial DNA and/or membrane structures. Advantageously, the wide range of mechanisms by which NO exerts its antibacterial effects reduces the risk that bacteria will develop resistance. Thus, NO-releasing materials may be good targets to battle bacterial infection. The antibacterial efficacy of NO-releasing materials may be dependent on both NO payloads and associated release kinetics.

Nitric oxide, an endogenously produced diatomic free radical, is associated with numerous biological processes, including platelet aggregation and adhesion, vasodilation, wound repair, the immune response, and carcinogenesis. Deficiency of NO can lead to some degree of malfunction of NO-relevant physiological systems. Exogenous NO delivery may be an effective strategy for the resolution of biomedical therapies ranging from cardiovascular diseases to antibacterial and anticancer therapies. However, the difficulty in regulating gaseous NO for therapeutics warrants the use of assorted synthetic NO donors (e.g., N-diazeniumdiolates, S-nitrosothiols, metal nitrosyls, organic nitrates), in order to control NO delivery. N-diazeniumdiolates (NONOates) may be useful as NO donors because of their good stability and their capacity for proton-triggered NO delivery under physiological conditions. In some instances, high NO total is an important parameter to effectively evaluate storage capability of good scaffolds. Additionally, a high density of secondary amine groups imbues certain donors with a high NO storage capacity. However, fast NO release and high NO storage may result in undesired toxicity to mammalian cells. Therefore, challenges exist in preparing biocompatible NO-releasing materials with high NO storage and low cytotoxicity, and such challenges, among others, are addressed according to several embodiments disclosed herein. Several embodiments of the currently described subject matter have one or more of the following advantages: efficient and unique synthesis routes and resultant chemical composition of polyaminoglycosides. Further advantages may include controllable amounts of secondary-amines and diverse exterior terminal groups (i.e., hydroxyl, methyl, hydroxymethyl, and primary amine) can be provided. The NO storage and NO-release kinetics of the generated nitric-oxide releasing scaffolds can be tuned for a particular application. This tuning is achieved, in several embodiments, by altering the type and/or number of functionalized monomers of the formulae disclosed herein. In several embodiments, additional functionalization of the amines in the generated nitric-oxide releasing scaffolds, for example, by compounds with different compositions further enables the control over NO-release kinetics. In some embodiments, the secondary amine group directly influences the stability of the N-diazeniumdiolate (or other NO carrier group), allowing for control over both NO storage and release kinetics.

Dental caries (e.g., tooth decay) affects 60%-70% school age children and the majority of adults in most industrialized countries. Worldwide, 11% of the total population suffers from severe periodontitis, which contributes to tooth loss and systematic diseases such as coronary, cardiovascular, stroke, and adverse pregnancy outcomes. Of >700 microorganisms in the oral cavity, cariogenic bacteria (e.g., *Streptococcus mutans, Actinomyces viscosus*) and periodontal pathogens (e.g., *Porphyromonas gingivalis, Aggregatibacter actinomycetemcomitans*) play a major role in the initiation and progression of oral diseases.

Developing oral therapeutics that are capable of killing those disease-causing bacteria is important to maintain a healthy oral cavity. Macromolecule NO-delivering vehicles (e.g., silica nanoparticles) kill Gram-negative periodontal pathogens. However, these materials have not been demonstrated to kill Gram-positive cariogenic bacteria at a safe concentration (e.g., a concentration that is bacteriocidal but non-toxic towards mammalian cells). Similar with those nanomaterials, the lack of biodegradability and potential cytotoxicity of the silica nanoparticles also hinders their future for biomedical application. Current research also focuses on utilizing nanomaterials including silver, gold, zinc, and copper, as replacement for traditional antibiotics that suffered from fostering bacterial resistance. These nanomaterials may exhibit promising antibacterial capacities with low toxicity. However, the lack of biodegradability may cause the accumulative toxicity, limiting their future for certain applications. Hyperbranched polymers (e.g. polyamino, polyester, polyether, and polysaccharides), may resolve one or more of these issues or others. Hyperbranched polymer structures, a sub-class of dendritic polymers, as disclosed herein are advantageously easy to synthesis, afford unique three-dimensional dendritic shapes, and can have low cytotoxicity.

Some embodiments disclosed herein pertain to NO-donating hyperbranched polymer structures. Some embodiments disclosed herein pertain to NO-donating hyperbranched polyaminoglycosides. Some embodiments disclosed herein pertain to methods of making and using NO-donating hyperbranched polyaminoglycosides. In some embodiments, as disclosed elsewhere herein, hyperbranched polyaminoglycosides are synthesized by the polymerization of one or more aminoglycosides. In some embodiments, the hyperbranched polyaminoglycosides are functionalized with NO absorbing moieties. In some embodiments, NO can be absorbed to these hyperbranched polyaminoglycosides to provide NO-donating hyperbranched polyaminoglycosides.

In some embodiments, the hyperbranched structures are synthesized from naturally produced aminoglycosides. In some embodiments, the hyperbranched polyaminoglycosides disclosed herein are biodegradable and/or biocompatible scaffold. In some embodiments, the hyperbranched polyaminoglycosides disclosed herein can be used in for biomedical applications. In some embodiments, without being bound to a particular mechanism or theory, it is believed that the polyaminoglycosides exhibit good biodegradability and low toxicity due to the existence of abundant glycosidic linkages and hydroxyl groups within the structure. In some embodiments, without being bound to a particular mechanism or theory, it is believed that these structures display enhanced antibacterial efficacy relative to other NO delivering scaffolds, in part, because of their highly branched structure.

In some embodiments, the hyperbranched polyaminoglycosides disclosed herein are employed in methods of treating patients and/or methods of killing bacteria (e.g., as antimicrobials). Also provided herein are methods for delivering nitric oxide to a subject, comprising administering an effective amount of any of the functionalized hyperbranched polyaminoglycosides disclosed herein to the subject. Methods of treating a disease state are also provided for herein, the methods comprising, in several embodiments administering an effective amount of any of the functionalized hyperbranched polyaminoglycosides disclosed herein to a subject in need of treatment, wherein the disease state is selected from the group consisting of a cancer, a cardiovascular disease, a microbial infection; platelet aggregation and platelet adhesion caused by the exposure of blood to a medical device; pathological conditions resulting from abnormal cell proliferation; transplantation rejections, autoimmune diseases, inflammation, vascular diseases; scar tissue; wound contraction, restenosis, pain, fever, gastrointestinal disorders, respiratory disorders, sexual dysfunctions, and sexually transmitted diseases. In several embodiments, the disease state is a microbial infection. In several embodiments, the disease state is dental caries or another disease of the mouth (gingivitis, periodontitis, etc.).

In several embodiments, there is provided for herein a method of reducing microbial load on a surface comprising applying a compound to a surface contaminated with a plurality of microbes wherein the compound comprises a nitric oxide (NO) releasing water-soluble functionalized hyperbranched polyaminoglycoside, the functionalized hyperbranched polyaminoglycoside comprising an NO donor, wherein the NO donor generates NO and induces oxidative and/or nitrosative damage to microbial DNA and membrane structures, thereby reducing microbial load, and wherein the plurality of microbes comprises two or more of the following: gram-positive bacteria, gram-negative bacteria, fungi, yeast, and viruses. In several embodiments, the surface is an organic surface. In several embodiments, the surface is human skin or mucosal surface. In several embodiments, application of the compound does not induce skin irritation or irritation of the mucosa. In several embodiments, the surface is animal skin. In several embodiments, the surface is in the mouth or surrounding tissue of a human or an animal. In several embodiments, application of the compound does not induce skin irritation or irritation of the mouth or surrounding tissue. In several embodiments, the surface is human airway tissue. In several embodiments, application of the compound (e.g., inhalation) does not induce irritation of airway epithelial cells. In several embodiments, the surface is an inorganic surface. In several embodiments, the inorganic surface is an external or internal surface of a medical device. In several embodiments, the medical device is a dental tool. In several embodiments, the application of the compound generates an anti-microbial coating on the external or internal surface of the medical device. In several embodiments, the medical device comprises an endoscope, dental drill or other dental device, a dental implant, or dental fixture.

In several embodiments, the microbial load to be reduced and/or eliminated comprises drug-resistant bacteria. In several embodiments, the drug-resistant bacteria comprise carbapenem-resistant Enterobacteriaceae. In several embodiments, the drug-resistant bacteria comprise Methicillin-resistant *Staphylococcus aureus*. In several embodiments, the microbe comprises human immunodeficiency virus, herpes simplex virus, papilloma virus, parainfluenza virus, influenza, hepatitis, Coxsackie Virus, herpes zoster, measles, mumps, rubella, rabies, pneumonia, hemorrhagic viral fevers, H1N1, and the like), prions, parasites, fungi, mold, yeast and bacteria (both gram-positive and gram-negative) including, among others, *Candida albicans, Aspergillus niger, Escherichia coli (E. coli), Pseudomonas aeruginosa (P. aeruginosa),* and *Staphylococcus aureus (S. aureus),* Group A streptococci, *S. pneumoniae, Mycobacterium tuberculosis, Campylobacter jejuni, Salmonella, Shigella, P. gingivalis, A. actinomycetemcomitans, A. viscosus,* and/or *S. mutans* and a variety of drug resistant bacteria. The terms microorganism and microbe shall be used interchangeably.

Microbes can include wild-type, genetically-engineered or modified organisms. In several embodiments, the formulations and methods disclosed herein are for topical use or treatment of a surface, such as the oral mucosa.

In several embodiments, there is provided a treating and/or preventing a microbial infection and/or proliferation comprising, contacting a surface (that is either contaminated with a plurality of microbes or that is susceptible to contamination, e.g., the mouth) with a compound comprising a nitric oxide (NO) releasing hyperbranched polyaminoglycoside, the functionalized hyperbranched polyaminoglycosides comprising an NO donor, wherein the NO donor generates NO and induces damage to the membrane and/or DNA of the microbes, thereby reducing the number of viable microbes and treating and/or preventing the infection or invasion, and wherein the plurality of microbes comprises one or more of viruses, gram positive bacteria, gram negative bacteria, drug resistant bacteria, molds, yeasts, fungi, and combinations thereof.

Depending on the embodiment, the methods and uses employ compounds disclosed herein that are formulated for administration via a topical route, oral administration, oral-topical (e.g., an oral rinse, mouth wash, liquid, solid, gel, paste, etc.), via irrigation (such as dental irrigation), via injection, via spray, via solid depots, via ingestion, or via inhalation. In one embodiment, a strip or other substrate is used for application of the formulation. The strip, in some embodiments, is made from a polymer including but not limited to polyethylene. In several embodiments, the route is topical and the methods and uses of the NO-releasing hyperbranched polyaminoglycosides are for the treatment of dental pathogens (e.g., one or more of *Porphyromonas gingivalis, Aggregatibacter actinomycetemcomitans, Streptococcus mutans,* and *Actinomyces viscosus*). In several embodiments, the NO-releasing hyperbranched polyaminoglycosides do not substantially damage human cells, including gingival fibroblasts, oral mucosa epithelial, or other cells in or around the mouth.

In some embodiments, the hyperbranched polyaminoglycosides disclosed herein are composed of dendritic units, linear units, and terminal units along and/or within chain lengths or arms of hyperbranched structures (as shown in FIG. 1). In some embodiments, the linear units and/or chains along the hyperbranched structure provide secondary amines as potential reactive sites for the addition of NO donor moieties.

Figure 2:
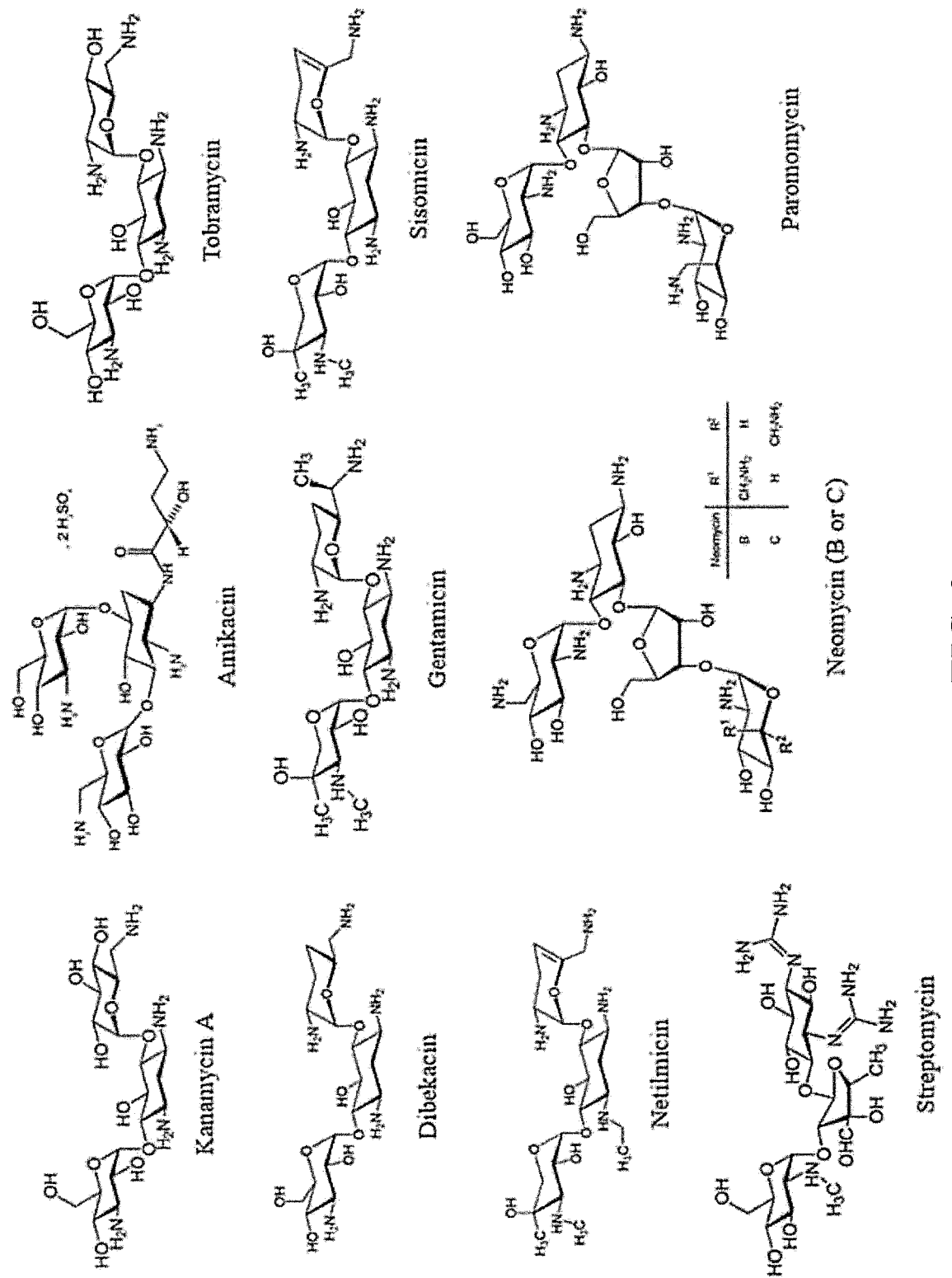
FIG. 2 shows structural representations of several aminoglycosides: kanamycin, amikacin, tobramycin, dibekacin, gentamicin, sisomicin, netilmicin, neomycins (B and C), paramomycin (neomycin E), and streptomycin.
Figure 3A:
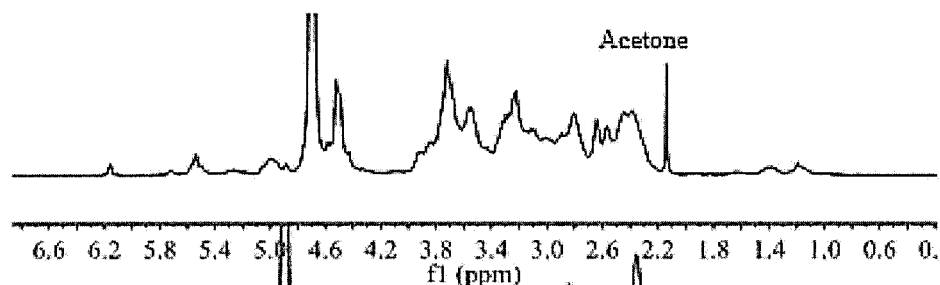
FIGS. 3A-3E show $^1$H NMR spectra for hyperbranched polyaminoglycosides: A) HPKA; B) HPNE; C) HPGE; D) HPKA-EDA; and E) HPKA-MEA.
Figure 3B:
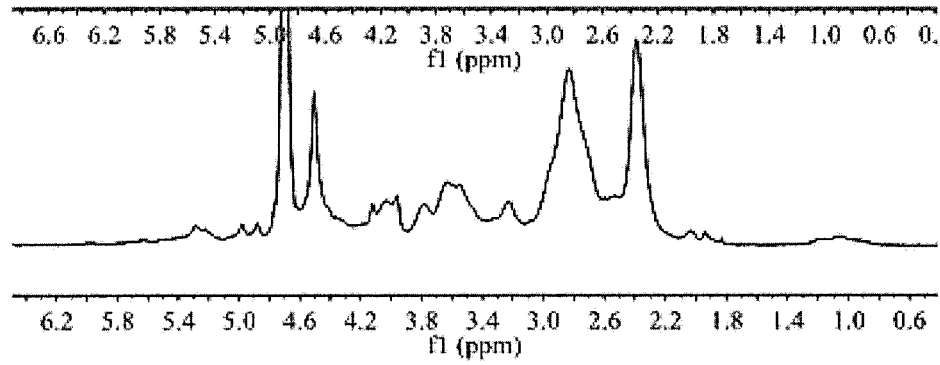
Figure 3C:
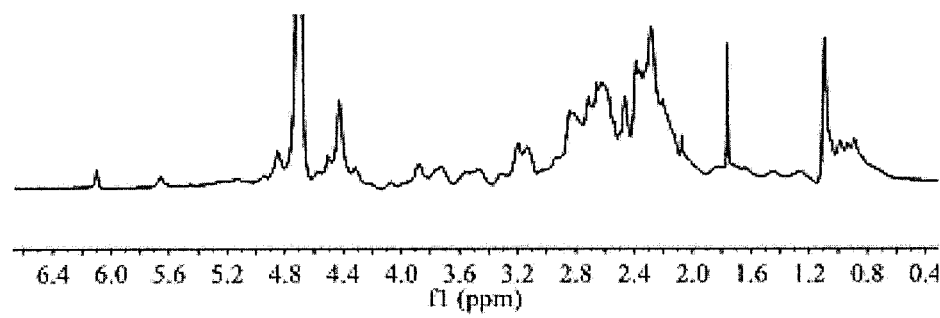
Figure 3D:
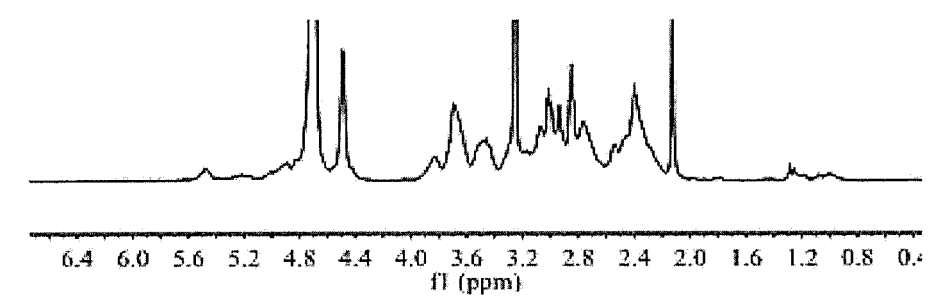
Figure 3E:
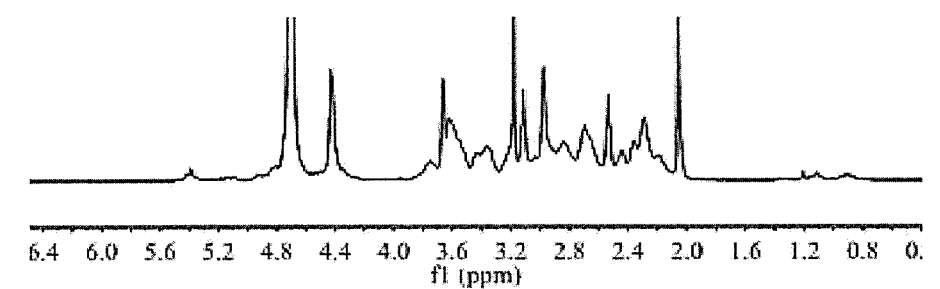
Figure 4A:
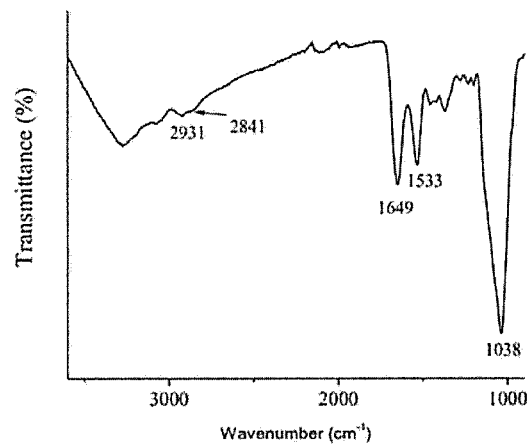
Figure 4B:
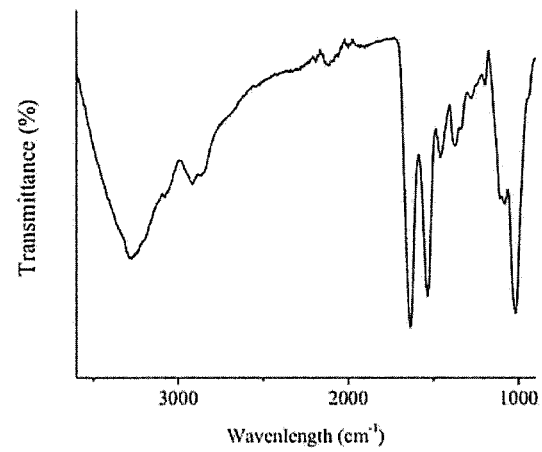
Figure 4D:
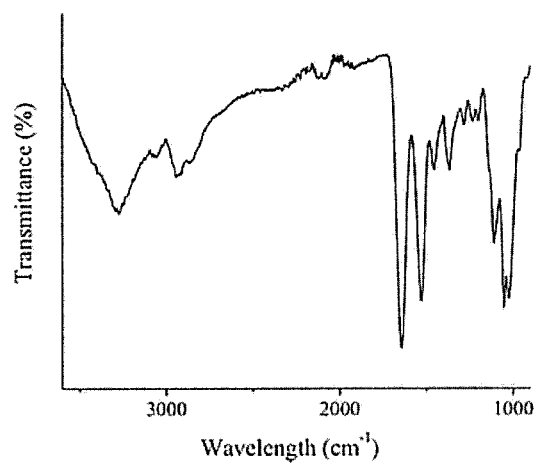
Figure 4D:
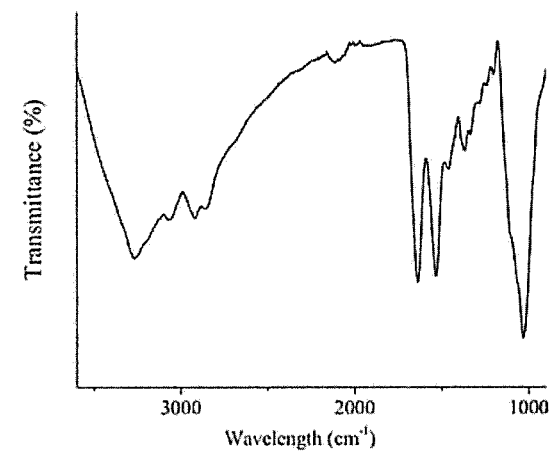
Figure 4E:
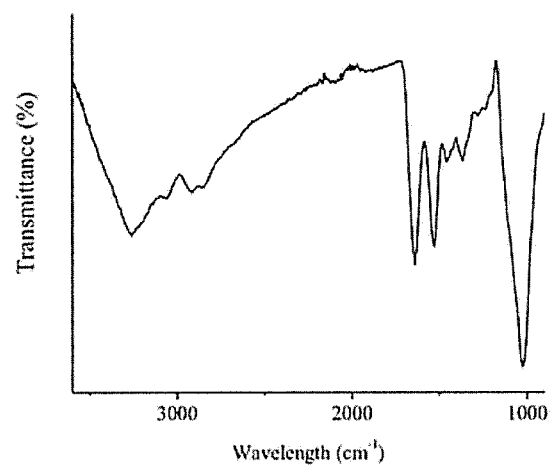

In some embodiments, the NO-donating hyperbranched polyaminoglycoside comprises NO-donating substituents that decorate the hyperbranched structure, for example, along the chain lengths or arms within the hyperbranched structure, as shown in FIG. 1. In some embodiments, hyperbranched polyaminoglycosides are synthesized by the polymerization of one or more natural aminoglycosides. In some embodiments, the natural aminoglycosides used to prepare the hyperbranched aminoglycosides disclosed herein can comprise one or more of kanamycin, gentamicin, and neomycin (shown in FIG. 2). In some embodiments, one or more of kanamycin, gentamicin, neomycin, and/or other natural or non-natural aminoglycosides are used (e.g., kanamycin, amikacin, tobramycin, dibekacin, gentamicin, sisomicin, netilmicin, neomycins (B and C), paramomycin (neomycin E), and streptomycin, dihydrostreptomycin or the like).

In some embodiments, the functionalized hyperbranched polyaminoglycosides disclosed herein comprise one or more aminoglycoside units having the structure of Formula I, Formula II, Formula III, Formula IV, Formula V, Formula VI, or Formula VII, an combinations thereof.

In some embodiments, the functionalized hyperbranched polyaminoglycosides comprises one or more units of the structure of Formula I:

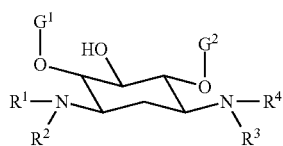

Formula I wherein $R^1$, $R^2$, $R^3$, and $R^4$ are independently selected from the group consisting of —H, optionally substituted $C_1$-$C_6$ alkyl, optionally substituted polyamino having 1 to 6 repeat units (with $C_1$-$C_6$ alkyl(s)), optionally substituted polyether having 1 to 6 repeat units (with $C_1$-$C_6$ alkyl(s)), or is a covalent bond to another atom of the hyperbranched polyaminoglycosides via a linking unit; and wherein $G^1$ and $G^2$ are independently a substituted or unsubstituted hexose or pentose. In some embodiments, for instance, the Formula I structure is the central hexose of one or more of kanamycin A, tobramycin, dibekacin, gentamicin, sisomicin, and/or netilmicin, and $G^1$ and $G^2$ are substituted or unsubstituted adjacent six-membered saccharide rings of those aminoglycosides.

In some embodiments, $G^1$ is selected from the group consisting of:

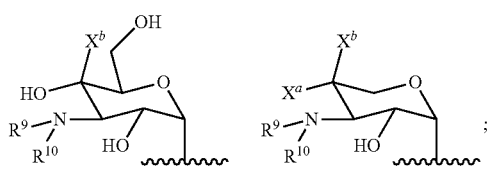

$G^2$ is selected from the group consisting of:

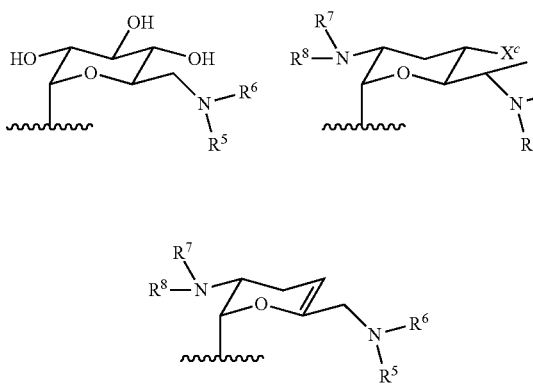

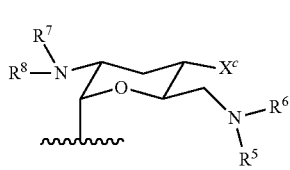

wherein $R^5$, $R^6$, $R^7$, $R^8$, $R^9$, and $R^{10}$ are independently selected from the group consisting of —H, optionally substituted $C_1$-$C_6$ alkyl, optionally substituted polyamino having 1 to 6 repeat units (with $C_1$-$C_6$ alkyl(s)), optionally substituted polyether having 1 to 6 repeat units (with $C_1$-$C_6$ alkyl(s)), or is a covalent bond to another atom of the hyperbranched polyaminoglycosides via a linking unit; and wherein $X^a$, $X^b$, and $X^c$ are independently selected from —H, —OH, and $C_1$-$C_6$ alkyl.

In some embodiments, the functionalized hyperbranched polyaminoglycosides comprises one or more units of the structure of Formula II:

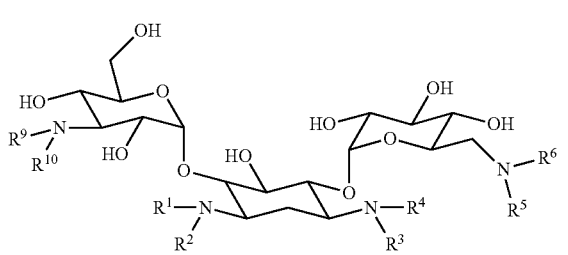

Formula II wherein $R^1$, $R^2$, $R^3$, $R^4$, $R^5$, $R^6$, $R^9$, and $R^{10}$ are as defined elsewhere herein. In some embodiments, Formula II can be prepared using kanamycin as a starting material and/or Formula II embodies a kanamycin-comprising hyperbranched polyaminoglycoside.

In some embodiments, the functionalized hyperbranched polyaminoglycosides disclosed herein comprise at one or more units of the structure of Formula III:

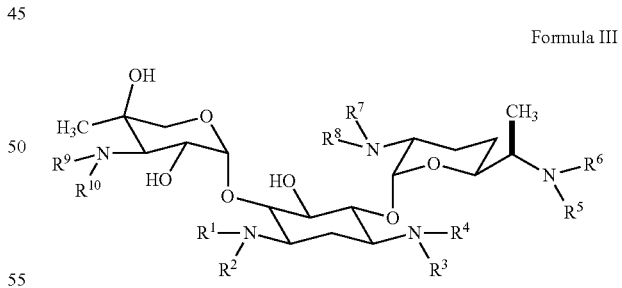

Formula III wherein $R^1$, $R^2$, $R^3$, $R^4$, $R^5$, $R^6$, $R^7$, $R^8$, $R^9$, and $R^{10}$ are as defined elsewhere herein. In some embodiments, Formula III can be prepared using gentamicin as a starting material and/or Formula III embodies a gentamicin-comprising hyperbranched polyaminoglycoside.

In some embodiments, the functionalized hyperbranched polyaminoglycosides disclosed herein comprise at one or more units of the structure of Formula IV:

Formula IV

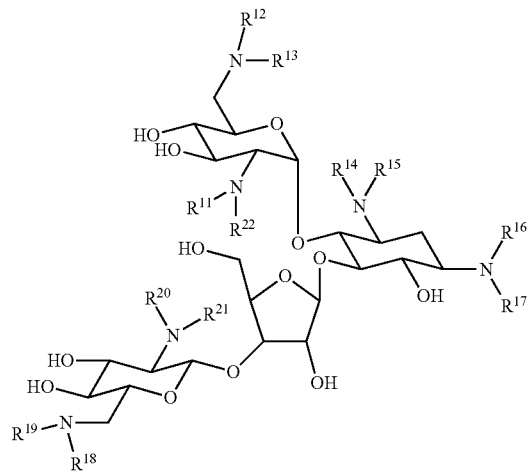

wherein $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently selected from the group consisting of: —H, optionally substituted $C_1$-$C_6$alkyl, optionally substituted polyamino having 1 to 6 repeat units (with $C_1$-$C_6$ alkyl(s)), optionally substituted polyether having 1 to 6 repeat units (with $C_1$-$C_6$ alkyl(s)), or is a covalent bond to another atom of the hyperbranched polyaminoglycosides via a linking unit. In some embodiments, Formula IV can be prepared using neomycin as a starting material and/or Formula IV embodies a neomycin-comprising hyperbranched polyaminoglycoside. In some embodiments, as with the other structures shown herein, Formula IV is intended to cover natural stereochemical arrangements (such as neomycin B or C), though only the C form is shown.

In some embodiments, the functionalized hyperbranched polyaminoglycosides disclosed herein comprise at one or more units of the structure of Formula V:

Formula V

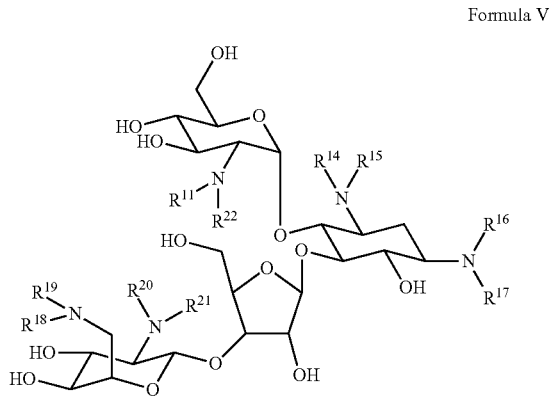

wherein $R^{11}$, $R^{14}$, $R^{15}$, $R^{16}$, $R^{17}$, $R^{18}$, $R^{19}$, $R^{20}$, $R^{21}$, and $R^{22}$ are as defined elsewhere herein. In some embodiments, Formula V can be prepared using paromomycin as a starting material and/or Formula V embodies a paromomycin-comprising hyperbranched polyaminoglycoside.

In some embodiments, the functionalized hyperbranched polyaminoglycosides disclosed herein comprise at one or more units of the structure of Formula VI:

Formula VI

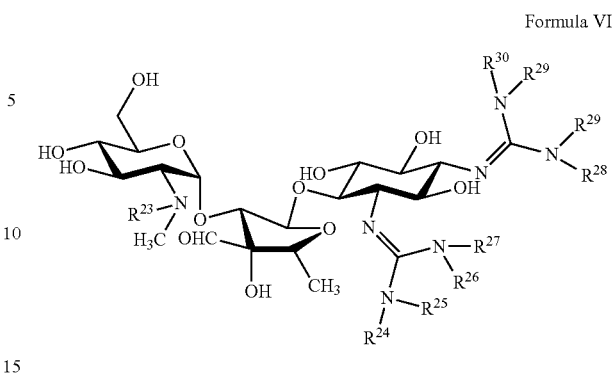

wherein $R^{23}$, $R^{24}$, $R^{25}$, $R^{26}$, $R^{27}$, $R^{28}$, $R^{29}$, and $R^{30}$ are independently selected from the group consisting of: —H, optionally substituted $C_1$-$C_6$alkyl, optionally substituted polyamino having 1 to 6 repeat units (with $C_1$-$C_6$ alkyl(s)), optionally substituted polyether having 1 to 6 repeat units (with $C_1$-$C_6$ alkyl(s)), or is a covalent bond to another atom of the hyperbranched polyaminoglycosides via a linking unit. In some embodiments, Formula VI can be prepared using streptomycin as a starting material and/or Formula VI embodies a streptomycin-comprising hyperbranched polyaminoglycoside.

In some embodiments, $R^1$ to $R^{30}$ of Formulas I-VI are independently selected from the group consisting of: —H, optionally substituted alkyl, optionally substituted polyamino having (with alkyl spacers between each amino group), optionally substituted polyether having (with alkyl spacers between each ether group), and a covalent bond to another atom of the hyperbranched polyaminoglycosides via a linking unit.

In some embodiments, the functionalized hyperbranched polyaminoglycosides disclosed herein comprise at one or more units of the structure of Formula VI:

Formula VII

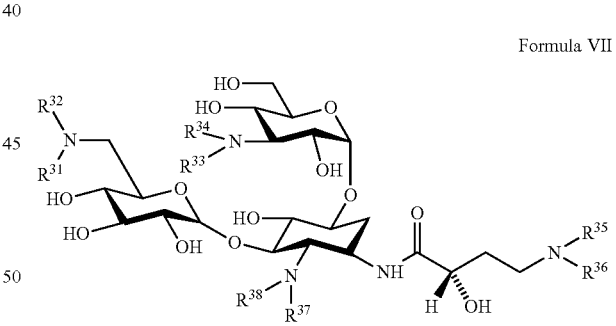

wherein $R^{31}$, $R^{32}$, $R^{33}$, $R^{34}$, $R^{35}$, $R^{36}$, $R^{37}$, and $R^{38}$ are independently selected from the group consisting of: —H, optionally substituted $C_1$-$C_6$alkyl, optionally substituted polyamino having 1 to 6 repeat units (with $C_1$-$C_6$ alkyl(s)), optionally substituted polyether having 1 to 6 repeat units (with $C_1$-$C_6$ alkyl(s)), or is a covalent bond to another atom of the hyperbranched polyaminoglycosides via a linking unit. In some embodiments, Formula VII can be prepared using amikacin as a starting material and/or Formula VII embodies a amikacin-comprising hyperbranched polyaminoglycoside.

In some embodiments, any one of Formulas I-VII can be in a natural or a non-natural (e.g., synthetically altered) stereochemical configuration.

In some embodiments, in addition to any one of the variables disclosed elsewhere herein, any one of $R^{138}$ (as a linker or an terminal-capping group) may also or alternatively be selected from the group consisting of —($C_1$-$_6$alkyl), —(($CH_2$)$_a$NH)$_b$—H, —(($CH_2$)$_a$NH)$_b$—($CH_2$)$_c$H, —(($CH_2$)$_a$X$^1$)$_b$—($CH_2$)H, —(($CH_2$)$_a$X$^2$)$_b$(($CH_2$)$_c$X$^3$)$_d$—($CH_2$)$_e$H, —(($CH_2$)$_a$NH)$_b$—, —(($CH_2$)$_a$NH)$_b$—($CH_2$)$_c$X$^1$, —(($CH_2$)$_a$X$^1$)$_b$—($CH_2$)$_c$X$^2$, and —(($CH_2$)$_a$X)$_b$(($CH_2$)$_c$X$^2$)$_d$—($CH_2$)$_e$—X$^3$, where each instance of a, b, c, d, or e is independently selected from an integer from 0 to 10 (e.g., 0, 1, 2, 3, 4, 5, 6, 7, 8, 9, 10). In several embodiments, each instance of $X^1$, $X^2$, and $X^3$ is independently selected from O, S, or NH.

In some embodiments, any —H of any of the hydroxyl groups present on any one of Formulae I-VII can be exchanged for a substituted or unsubstituted $C_1$-$C_6$ alkyl, or substituted or unsubstituted polyether having 1 to 6 repeat units (with $C_1$-$C_6$ alkyl(s)) where the oxygen of the hydroxyl provides an oxygen of the polyether group. In some embodiments, the hydrogen of any of the hydroxyl groups present on any one of Formulae I-VII can be exchanged for a linking unit as described elsewhere herein.

In some embodiments, aminoglycosides of any one of Formulas I-VII are polymerized and/or crosslinked using one or more polymerizing agents and/or crosslinking agents. In some embodiments, after polymerizing the aminoglycosides are hyperbranched structures. In some embodiments, the polymerizing agents are multifunctional (bifunctional, trifunctional, tetrafunctional, etc.) molecules having moieties that react with one or more substituents of the aminoglycosides. In some embodiments, the multifunctional polymerizing agents comprise molecules with one or more electrophilic moieties that react with, for instance, an amine or other nucleophile on the aminoglycoside (e.g., a hydroxyl). For instance, an acrylate derived from a monomer selected from the salt, ester, and conjugate bases of acrylic acid and its derivatives may be used for polymerizing agents and or crosslinking. In one embodiment, the acrylate is derived from a monomeric methacrylate. In another embodiment, the acrylate is derived from a monomer selected from the group consisting of a methyl acrylate, ethyl acrylate, methyl methacrylate, acrylamide, ethyl methacrylate, 2-chloroethyl vinyl ether, 2-ethylehexyl acrylate, hydroxethyl methacrylate, hydroxethyl acrylate, butyl acrylate, butyl methacrylate, N-(2-hydroxypropyl)methacrylamide, N-(3-aminopropyl)methacrylamide hydrochloride, N-(3-BOC-aminopropyl)methacrylamide, 2-aminoethyl methacrylate hydrochloride, 2-(tert-butylamino)ethyl methacrylate, n-iso-propylacrylamide, 2-methoxyethyl acrylate, n-ethylmethacrylamide, n-vinyl acetamide, 2-N-morpholinoethyl acrylate, methacryloyl-L-lysine, 2-(methylamino) ethyl acrylate, and 2-(methylamino)ethyl methacrylate. In another embodiment, the acrylate is derived from a diacrylate. For example, the diacrylate may be ethylene glycol diacrylate, triethylene glycol diacrylate, tetraethylene glycol diacrylate, polyethylene glycol diacrylate, tricyclodecan dimethanol diacrylate, N-acryloxysuccinimide, N-(2-hydroxypropyl)methacrylamide, Bis [2-(methacryloyloxy) ethyl] phosphate, diacrylamide, and N,N'-methylenebisacrylamide.

In some embodiments, the polymerizing agents comprise one or more Michael acceptors. As used herein, the term "Michael acceptor" refers to chemical moieties that act as electrophiles, such as, but not limited to, α,β unsaturated carbonyl compounds, enolates, etc. In some embodiments, the polymerizing agent comprises one or more acrylate functionalities. In some embodiments, the Michael acceptor is an acrylate. In some embodiments, the polymerizing agent is a diacrylate (e.g., N,N'-methylenebis(acrylamide), ethylene glycol diacrylate, propane diol diacrylate, butandiol diacrylate, etc.), a triacrylate (e.g., trimethylolpropane triacrylate, pentaerythritol triacrylate, pentaerythritol triacrylate, glycerol propoxylate (1PO/OH) triacrylate, trimethylolpropane propoxylate triacrylate), etc.), a tetraacrylate, or another acrylate having a plurality of acrylate groups (e.g., 5, 6, 7, or more).

In some embodiments, the polymerizing agent is represented by one or more of the following structures:

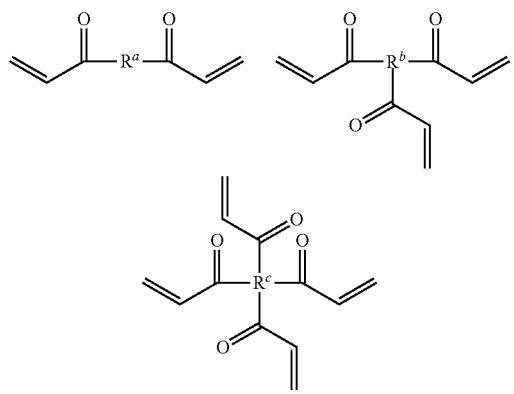

wherein $R^a$, $R^b$, and $R^c$ are independently selected from the group consisting of optionally substituted $C_1$-$C_6$alkyl, optionally substituted polyamino having 1 to 6 repeat units (with $C_1$-$C_6$ alkyl(s)), or optionally substituted polyether having 1 to 6 repeat units (with $C_1$-$C_6$ alkyl(s)). $R^a$, $R^b$, and $R^c$ are independently selected from the group consisting of —NH—(($CH_2$)$_f$NH)$_g$—, —X$^4$—(($CH_2$)$_f$X$^5$)$_g$—, where f and g are independently selected from an integer from 0 to 10 (e.g., 0, 1, 2, 3, 4, 5, 6, 7, 8, 9, 10). In several embodiments, each instance of $X^4$ and $X^5$ is independently selected from O, S, or NH. In some embodiments, $R^a$ is —NH—$CH_2$—NH— (as from N,N'-methylenebis(acrylamide)).

In some embodiments, as described elsewhere herein, after polymerization, the functionalized hyperbranched polyaminoglycosides of any one of Formulae I-VII further comprise a linking unit (e.g., the remaining portion of a polymerizing agent after reaction with one or more aminoglycosides). In some embodiments the linking unit spans two or more aminoglycosides through, for instance, an amino group of the aminoglycoside. In some embodiments the linking unit comprises an structure selected from the group consisting of —(C=O)alkyl(C=O)—, -alkyl-(C=O)-alkyl-(C=O)-alkyl-, —(C=O)polyamino(C=O)—, -alkyl-(C=O)-polyamino-(C=O)-alkyl-, —(C=O)polyether (C=O)—, and -alkyl-(C=O)-polyether-(C=O)-alkyl-.

In some embodiments, the linking unit of the hyperbranched polyaminoglycoside comprises a structure selected from the group consisting of:

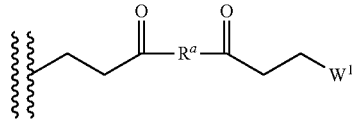

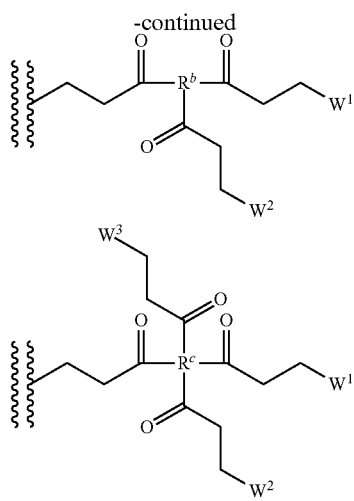

wherein $R^a$, $R^b$, and $R^c$ are selected from the group consisting of optionally substituted $C_1$-$C_6$ alkyl, optionally substituted polyamino having 1 to 6 repeat units (with $C_1$-$C_6$ alkyl(s)), or optionally substituted polyether having 1 to 6 repeat units (with $C_1$-$C_6$ alkyl(s));

wherein "⸹⸹" indicates an attachment to the recited aminoglycoside; and wherein $W^1$, $W^2$, or $W^3$ are independently selected from an aminoglycoside or an end-capping group, as disclosed elsewhere herein.

In some embodiments, the linking unit of the hyperbranched polyaminoglycoside comprises a structure represented by one of the following:

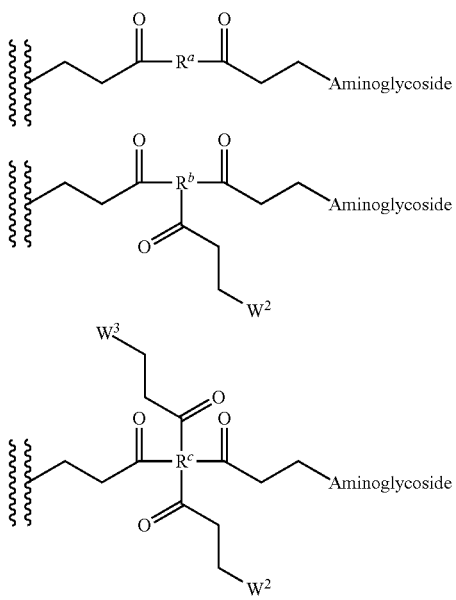

where the "Aminoglycoside" represents a second aminoglycoside (optionally another copy of the first aminoglycoside) to which the structure of Formulae I-VII is covalently linked and where $W^2$ and $W^3$ are as defined elsewhere herein.

In some embodiments, after polymerization with a linking unit, one or more of the polymerizing agents may comprise an unreacted terminal group. In some embodiments, those terminal groups can be end-capped by further reacting the hyperbranched polyaminoglycosides with an endcapping agent. In some embodiments, the end-capping agent comprises one or more of $H_2N-((CH_2)_aNH)_b-H$, $H_2N-((CH_2)_aNH)_b-(CH_2)_cH$, $H_2N-((CH_2)_aX^1)_b-(CH_2)_cH$, $HX^1-((CH_{2a}((CH_2)_aX^{2b}((CH_2)_cX^3)_d-(CH_2)_eH$, $-((CH_2)_aNH)_b-$, $-((CH_2)_aNH)_b-(CH_2)_cX^1$, $-((CH_2)_aX^1)_b-(CH_2)_cX^2$, and $-((CH_2)_aX^1)_b((CH_2)_cX^2)_d-(CH_2)_e-X^3$, where each instance of a, b, c, d, or e is independently selected from an integer from 0 to 10 (e.g., 0, 1, 2, 3, 4, 5, 6, 7, 8, 9, 10). In several embodiments, each instance of $X^1$, $X^2$, and $X^3$ is independently selected from O, S, or NH. In some embodiments, the end-capping agent is one or more of $H_2NCH_2CH_2NH_2$ and $H_2NCH_2CH_2OH$. In some embodiments, the end-capping agent results in a substituent selected from one or more of $-NH-((CH_2)_aNH)_b-H$, $-NH-((CH_2)_aNH)_b-(CH_2)_cH$, $-NH-((CH_2)_aX^1)_b-(CH_2)_cH$, $((CH_2)_aX^2)_b((CH_2)_cX^3)_d-(CH_2)_eH$, $-((CH_2)_aNH)_b-$, $-((CH_2)_aNH)_b-(CH_2)_cX^1$, $-((CH_2)_aX^1)_b-(CH_2)_cX^2$, and $-((CH_2)_aX)_b((CH_2)_cX^2)_d-(CH_2)_e-X^3$. In some embodiments, the end-capping agent results in a substituent selected from one or more of $-NHCH_2CH_2NH_2$ and $-NHCH_2CH_2OH$.

In some embodiments, after an amine from the aminoglycoside reacts with one or more linking units, the following structures may results:

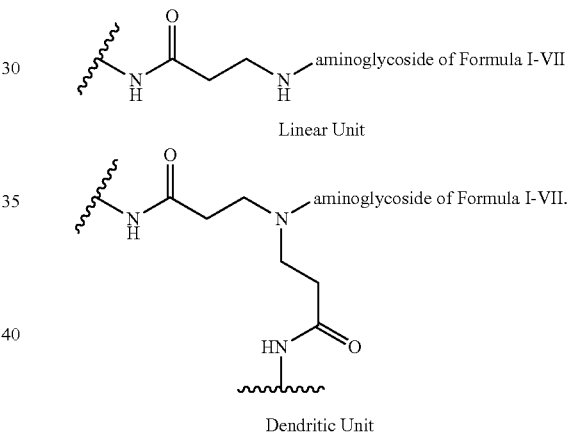

Linear Unit

Dendritic Unit

As illustrated above, the dendritic unit results from the reaction of an aminoglycoside amine with two molecules of linking unit and the linear unit results from an aminoglycoside amine reacting with one molecule of linking unit.

In some embodiments, the hyperbranched aminoglycoside is prepared in a one-pot synthesis. In some embodiments, the polymerizing agent (e.g., N,N'-methylenebis(acrylamide)) is added to an aminoglycoside.

In some embodiments, the hyperbranched aminoglycoside structures disclosed herein have bactericidal activity in and of themselves (e.g., by virtue of polycationic charge, etc.). In some embodiments, the aminoglycosides can be further functionalized with additional substituents to provide additional NO releasing functional groups (for example, in the linear units, where polyamines are used for end-capping, and where polyamines are present in the linking units). In some embodiments, for example, as shown in FIG. 1, the linear units of these hyperbranched polymers provide multiple secondary amines. In some embodiments, the secondary amines are NO acceptors and can be reacted with NO to yield a NO donor (e.g., a NO-donating hyperbranched polyaminoglycoside).

In some embodiments, the NO donor comprises any one of the following nitric oxide releasing moieties:

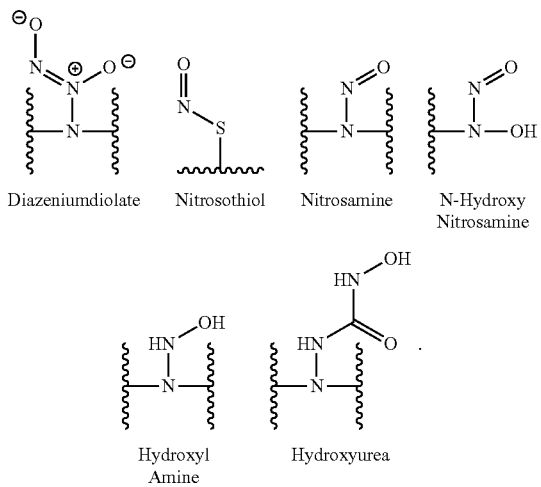

Diazeniumdiolate    Nitrosothiol    Nitrosamine    N-Hydroxy Nitrosamine

Hydroxyl Amine    Hydroxyurea where "⌇" indicates attachment to other atoms within the hyperbranched aminoglycoside structure (e.g., any instance of —H, —CH$_2$—, —CH—, etc.). In some embodiments, the NO donor is a N-diazeniumdiolate NO donor. In some embodiments, the NO donor is attached along a linear unit as shown below:

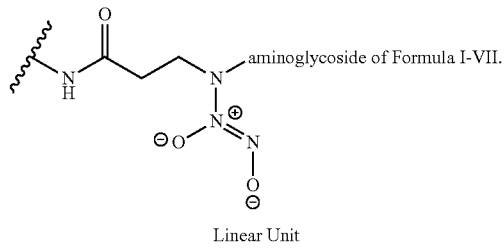

Linear Unit

In some embodiments, as disclosed elsewhere herein, end-capping molecules can be added to the hyperbranched polyaminoglycosides to provide additional and/or alternative NO acceptors. In some embodiments, the following end-capping groups can be used:

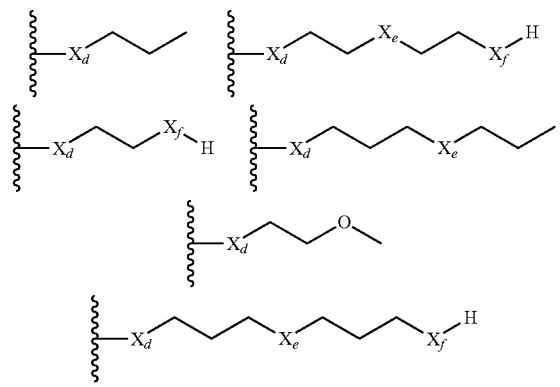

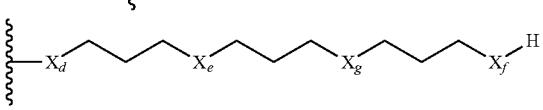

where $X_d$, $X_e$, $X_f$, and X, are selected from O, S, NH or a nitric oxide releasing moiety as disclosed elsewhere herein. As disclosed elsewhere herein, secondary amines of these structures can be used to provide NO donors such as diazeniumdiolate.

In some embodiments, the nitric oxide donor is selected from the group consisting of a diazeniumdiolate, nitrosothiol, a nitrosamine, a hydroxyl nitrosamine, a hydroxyl amine, a hydroxyurea, and a combination thereof.

In some embodiments, the reaction of the hyperbranched aminoglycoside with NO is performed in basic or alkaline conditions. In some embodiments, the functionalization of hyperbranched polyaminoglycoside with NO is performed under alkaline conditions. In some embodiments, alkaline conditions include those having pH values of equal to or at least about: 7.5, 8.0, 9.0, 10.0, 12.0, or ranges including and/or spanning the aforementioned values.

In some embodiments, the methods disclosed herein provide NO-releasing hyperbranched polyaminoglycosides having NO storage capacities (in mol NO/mg hyperbranched polyaminoglycosides) of greater than or equal to about: 0.25, 0.4, 0.5, 0.6, 0.7, 0.8, 0.9, 1.0, 1.1, 1.2, 1.3, 1.4, 1.5, 2.0, 3.0, or ranges including and/or spanning the aforementioned values. For example, in some embodiments, the range is between about 0.4 and about 1.3 μmol NO/mg hyperbranched polyaminoglycosides. In other embodiments, the range is between about 0.4 to about 0.6 or between about 1.2 to about 1.3 μmol NO/mg hyperbranched polyaminoglycosides.

In some embodiments, within 2 h of being added to a PBS buffer solution as described in the Examples, the NO-releasing hyperbranched polyaminoglycosides, release greater than or equal to about: 25%, 50%, 75%, 85%, 90%, 95%, 100%, or ranges including and/or spanning the aforementioned values, their total wt % of bound NO. In several embodiments, NO release in use for reducing or eliminating a biofilm occurs in similar amounts, e.g., about 20-25%, about 30-50%, about 60-75%, at least 80%, at least 85%, at least 90%, at least 95%, and ranges including and/or spanning the aforementioned values, of the total wt % of bound NO.

In some embodiments, the NO release may occur over a period of about 0.01 hours, 0.1 hours, 0.25 hours, 0.5 hours, 1 hour, 2 hours, 3 hours, 4 hours, 5 hours, 10 hours, 15 hours, 20 hours, 24 hours, 36 hours, 48 hours, or 60 hours. In some embodiments, the NO release occurs in less than or equal to about: 0.01 hours, 0.1 hours, 0.25 hours, 0.5 hours, 1 hour, 2 hours, 3 hours, 4 hours, 5 hours, 10 hours, 15 hours, 20 hours, 24 hours, 36 hours, 48 hours, 60 hours, or ranges including and/or spanning the aforementioned values. In some embodiments, nitrosamine is not present during NO release.

As disclosed herein, the NO release for the hyperbranched polyaminoglycosides may be measured over a period of 2 hours. In some embodiments, the hyperbranched polyaminoglycoside has a total NO release after 2 hours of at least about 0.1, 0.2, 0.25, 0.3, 0.4, 0.5, 0.6, 0.7, 0.8, 0.9, 1.0, or ranges including and/or spanning the aforementioned values. For example, in some embodiments, the hyperbranched polyaminoglycoside has a total NO release after 2 hours between about 0.2 and about 1.0 μmol NO/mg hyperbranched polyaminoglycosides. In other embodiments, the range is between about 0.25 to about 0.8 μmol of NO per milligram of the hyperbranched polyaminoglycoside.

In some embodiments, the NO release may be measured by its half-life. In some embodiments, the half-life for NO release is measured in minutes and may be at least about 10, 20, 30, 40, 50, 60, 70, 80, 90, 100, 110, 120, 130, 140, 150, 160, 170, 180, 190, 200, 210, 220, 230, or 240 min or more. In some embodiments, the half-life for NO release includes ranges including and/or spanning the aforementioned values. For example, in some embodiments, the half-life for NO release is in a range from about 10 to about 240, about 70 to about 190 min, or about 80 to about 150 min. As used herein the phrase "nitrosamine is not present" refers to levels nitrosamine which are not detectable as determined by a UV-vis spectrum (or by other accepted methods in the art).

In some embodiments, the hyperbranched polyaminoglycosides have molecular weights (Mn or Mw) of less than or equal to about: 25, 15, 10, 9.5, 9, 8.5, 8, 7.5, 7, 6.5, 6, 5.5, 5, 4.5, 4, 3.5, 3, 2.5, 2, 1.5, 1, or 0.5 kDa, or ranges including and/or spanning the aforementioned values. For example, in some embodiments the molecular weights (Mn or Mw) are in a range between about 1.5 to about 7, about 1.5 to about 4.5, or about 2 to about 7.

In some embodiments, the polydispersity (PDI) of the hyperbranched polyaminoglycosides is less than or equal to about: 2, 1.5, 1.4, 1.3, 1.2, 1.1, or ranges including and/or spanning the aforementioned values. For example, in some embodiments, the polydispersity may be in the range between about 1.3 to about 2. In some embodiments, the nitrogen wt % of the hyperbranched polyaminoglycosides is greater than or equal to about: 5%, 10%, 12.5%, 15%, 20%, or ranges including and/or spanning the aforementioned values.

In some embodiments, the degree of branching in the hyperbranched polyaminoglycosides is at least about 0.2, 0.25, 0.3, 0.35, 0.4, 0.45, 0.5, 0.55, 0.6, 0.65, 0.7, 0.75, or ranges including and/or spanning the aforementioned values. For example, in some embodiments, the hyperbranched polyaminoglycoside has a degree of branching (DB) in a range between about 0.2 to about 0.75, about 0.3 to about 0.6, or about 0.4 to about 0.5.

In some embodiments, the disclosed functionalized NO-releasing hyperbranched polyaminoglycosides have antimicrobial activity. In some embodiments, the disclosed functionalized NO-releasing hyperbranched polyaminoglycosides provide greater than or equal to 90% bacterial reduction in a bacterial viability assay performed under static conditions over 2 hours against one or more of P. aeruginosa, S. aureus P. gingivalis, A. actinomycetemcomitans, A. viscosus, and/or S. mutans at a polymer concentration of equal to or less than about: 8 mg/mL, 6 mg/mL, 4 mg/mL, 2 mg/mL, 1 mg/mL, 0.5 mg/mL, or ranges including and/or spanning the aforementioned values. In some embodiments, the disclosed functionalized NO-releasing hyperbranched polyaminoglycosides provide greater than or equal to 99% bacterial reduction in a bacterial viability assay performed under static conditions over 2 hours against a gram positive bacteria at a polymer concentration of equal to or less than about: 8 mg/mL, 6 mg/mL, 4 mg/mL, 2 mg/mL, 1 mg/mL, 0.5 mg/mL, or ranges including and/or spanning the aforementioned values. In some embodiments, the disclosed functionalized NO-releasing hyperbranched polyaminoglycosides provide greater than or equal to 99% bacterial reduction in a bacterial viability assay performed under static conditions over 2 hours against a gram negative bacteria at a polymer concentration of equal to or less than about: 8 mg/mL, 6 mg/mL, 4 mg/mL, 2 mg/mL, 1 mg/mL, 0.5 mg/mL, or ranges including and/or spanning the aforementioned values. In several embodiments, bacterial reduction is greater than 95%, greater than 98%, or greater than 99%. Some embodiments pertain to a pharmaceutical formulation comprising a hyperbranched polyaminoglycoside as disclosed herein and a pharmaceutically acceptable carrier.

Some embodiments pertain to a method of delivering nitric oxide to a subject, comprising administering an effective amount of a hyperbranched polyaminoglycoside as disclosed herein to a subject.

Some embodiments pertain to methods of killing bacteria and/or microbes by applying NO donating hyperbranched polyaminoglycosides to the bacteria and/or microbes.

In some embodiments, the bacteria are dental bacteria. In some embodiments, the disclosed compounds can be used in methods of preventing cavities.

EXAMPLES

Hyperbranched polyaminoglycosides represent a novel biodegradable platform that can be readily modified with NO donors for NO-release application. Further, the hyperbranched polyaminoglycosides can be functionalized with NO donating moieties to provide dual-action antimicrobials with improved antibacterial activity. As disclosed elsewhere herein are the synergistic effects of co-delivering aminoglycoside and NO from an amphiphilic block copolymer system against an infection-causing pathogen, P. aeruginosa, planktonic and biofilm culture. Disclosed in an example is the synthesis of NO-releasing aminoglycoside-terminated hyperbranched polyaminoglyco sides constructed from various naturally produced exemplary aminoglycosides (e.g., kanamycin, gentamicin, and neomycin). The exterior functional groups of hyperbranched polykanamycin were altered to evaluate the potential effects on their NO-release properties. The antibacterial efficacies of these NO-releasing hyperbranched polyaminoglycosides were examined against a wide range of common dental pathogens (i.e., *Porphyromonas gingivalis, Aggregatibacter actinomycetemcomitans, Streptococcus mutans*, and *Actinomyces viscosus*). Also investigated was the cytotoxicity of these constructs against human gingival fibroblasts.

Example 1: Synthesis of Certain Embodiments 1.1 Materials and Methods

Kanmycin sulfate (KA), neomycin trisulfate salt hydrate (NE), gentamicin sulfate salt (GE), N,N'-methylenebis(acrylamide) (bis-MBA), ethylene diamine (EDA), mono-ethanol amine (MEA), propidium iodide, 3-(4,5-dimethylthiazol-2-yl)-5-(3-carboxymethoxyphenyl)-2-(4-sulfophenyl)-2H-tetrazolium inner salt (MTS), and phosphate-buffered saline (PBS) for cell culture were purchased from Sigma-Aldrich (St. Louis, Mo.). 4,5-Diaminofluorescein diacetate (DAF-2DA) was purchased from Calbiochem (San Diego, Calif.). CDC anaerobe 5% sheep blood agar, brain heart infusion (BHI) broth and agar, and GasPak™ EZ campy container system sachets were purchased from Becton, Dickinson, and Company (Franklin Lakes, N.J.). Wilkins-Chalgren (W-C) broth was purchased from Acumeida Neogen Corporation (Lansing, Mich.). Human gingival fibroblast cell line and FibroLife fibroblast serum-free media were purchased from Lifeline Cell Technology LLC (Frederick, Md.). Pure nitric oxide gas, argon, nitrogen, and nitric oxide calibration (25.87 ppm in nitrogen) was purchased from Airgas (Durham, N.C.).

Common laboratory salts and solvents were purchased from Fisher Scientific (Pittsburgh, Pa.). Water was purified using a Millipore Milli-Q UV Gradient A10 System (Bethlehem, Pa.) to a final resistivity of 18.2 MΩ cm and total organic content of <10 ppb. Proton nuclear magnetic resonance ($^1$H NMR) spectra were recorded on a 400 MHz Bruker instrument. Carbon nuclear magnetic resonance ($^{13}$C NMR) was performed on a 600 MHz Bruker instrument. In inverse gated 1H decoupling method with 10 s retention time were used for quantitative $^{13}$C NMR. Size exclusion chromatography was in-line with light scattering (SEC-LS) to determine the molecular weight and polydispersity. The eluent (PBS, 0.01% azide, pH 7.4) was passed through a miniDawn TREOS multi-angle light scattering detector (Wyatt Technology, Santa Barbara, Calif.) coupled to a Waters 2414 refractive index detector (Waters Chromatography, Milford, Mass.). 1.2 Synthesis of hyperbranched polyaminoglycosides.

Hyperbranched polyaminoglycosides (HPAs) were synthesized through a Michael-addition reaction between N,N'-methylenebisacrylamide (MBA) and various natural aminoglycosides (i.e., kanamycin, neomycin, and gentamicin). As shown in scheme 1, the molar ratio of MBA and aminoglycosides was initially controlled at 3:2 to generate aminoglycoside-terminated HPA (i.e., HPKA, HPNE, and HPGE, respectively). Exterior functional groups of the scaffolds have been previously reported to have great effect on nitric oxide (NO)-release properties and bactericidal activities, because the terminal groups may change the kinetics of NO donor decomposition and bacterial-scaffold association behavior.

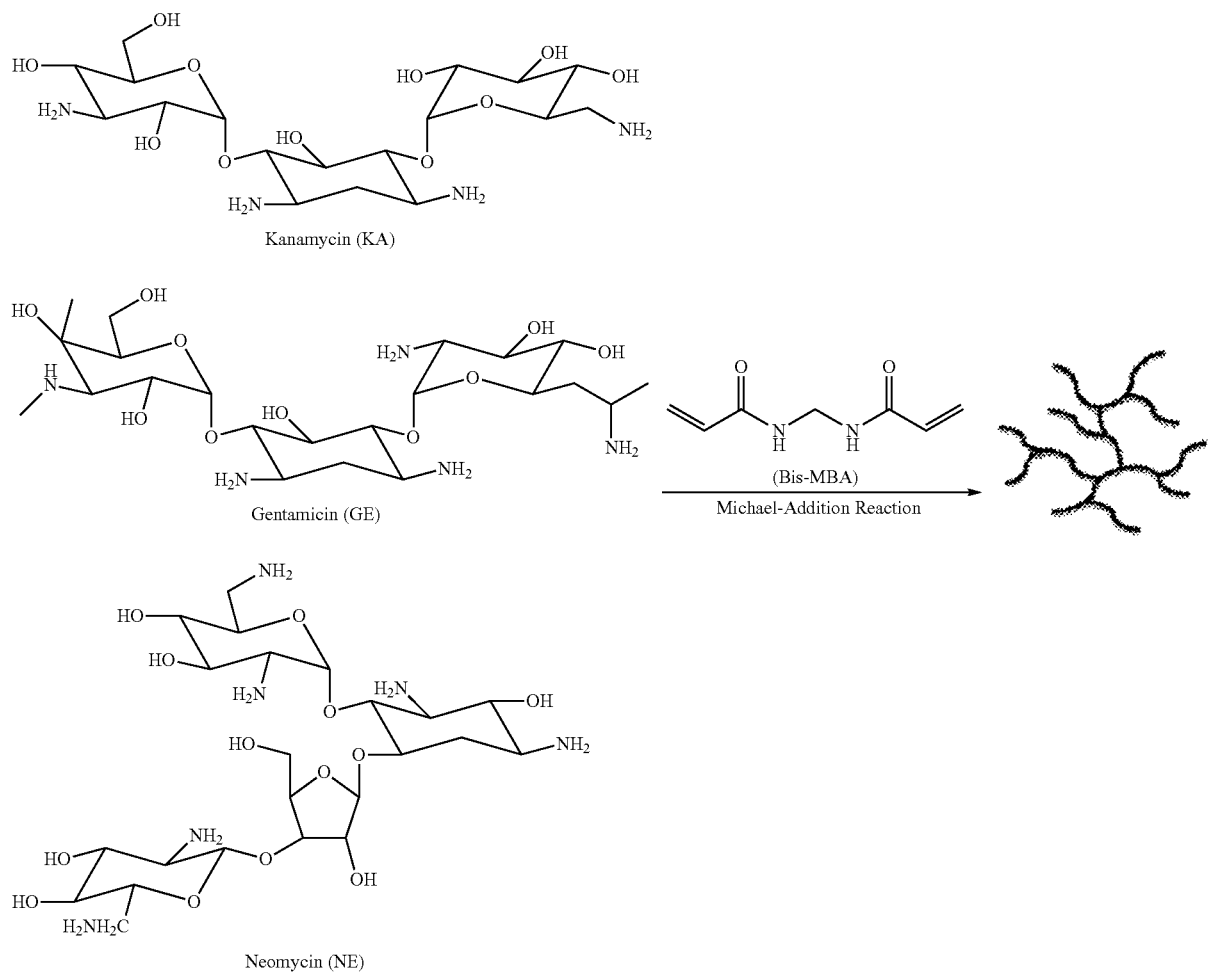

Scheme 1. The synthesis of aminoglycoside-terminated hyperbranched polyaminoglycosides.

The synthesis of hyperbranched polyaminoglycosides was as follows. Briefly, 2.5 mmol aminoglycosides (KA, NE, or GE) sulfate was mixed with 3.75 mmol bis-MBA in 50 mL D.I. water supplemented with sodium bicarbonate that neutralized the sulfate on the aminoglycoside, to generate hyperbranched polyaminoglycosides (i.e., hyperbranched polyaminoglycosidyl kanamycin (HPKA), hyperbranched polyaminoglycosidyl neomycin (HPNE), or hyperbranched polyaminoglycosidyl gentamicin (HPGE)). Each reaction mixture was stirred 3 days under nitrogen stream at 60° C. Each of the resulting solutions was concentrated by rotary evaporation, followed by dialysis against Milli Q water for 3 days. The purified products were recovered by lyophilization as fluffy powders. 1.3 End-Capping of hyperbranched polyaminoglycosides.

To evaluate the potential effect of end-capping the aminoglycosides, hyperbranched polyaminoglycosides not terminated by aminoglycoside were prepared using hyperbranched polykanamycin as an example (scheme 2). The feeding mixedolar ratio of MBA and kabis-MBA in 50 was increased to 5:2, generating vinyl groups-terminated HPKA* intermediate. Ethylenediamine (EDA) or monoethanolamine (MEA) was then used as end capping reagent to react with HPKA*, productary evaporation, followHPKA terminated by dialysis agEDA (HPKA-EDA) or MEA (HPKA-MEA).

MEA was then added as the capping agent into the reaction mixture, followed by reacting for 1 day at 40° C. to obtain HPKA-EDA or HPKA-MEA. The resulting solution was again concentrated by rotary evaporation, followed by dialysis against Milli Q water for 3 days. The purified product was also recovered by lyophilization as fluffy powder. The hyperbanched polyaminoglycosides were characterized by nuclear magnetic resonance (NMR) spectrometry. $^1$H NMR data of HPKA, HPNE, and HPGE consisted of the following peak (400 MHz, D2O, δ): 1.0-1.5 (CHCH$_2$CH); 2.2-3.3 (O=CCH$_2$CH$_2$, O=CCH$_2$CH$_2$, NCH, CHNH, CHNH$_2$, CHCH$_2$NH$_2$, CHCH$_2$NH, CHCH$_2$N), 3.3-3.8 (CH$_2$OH), 4.4 (NHCH$_2$NH), 5.0-6.0 (CH(OCH)$_2$CH). HPKA-MEA and

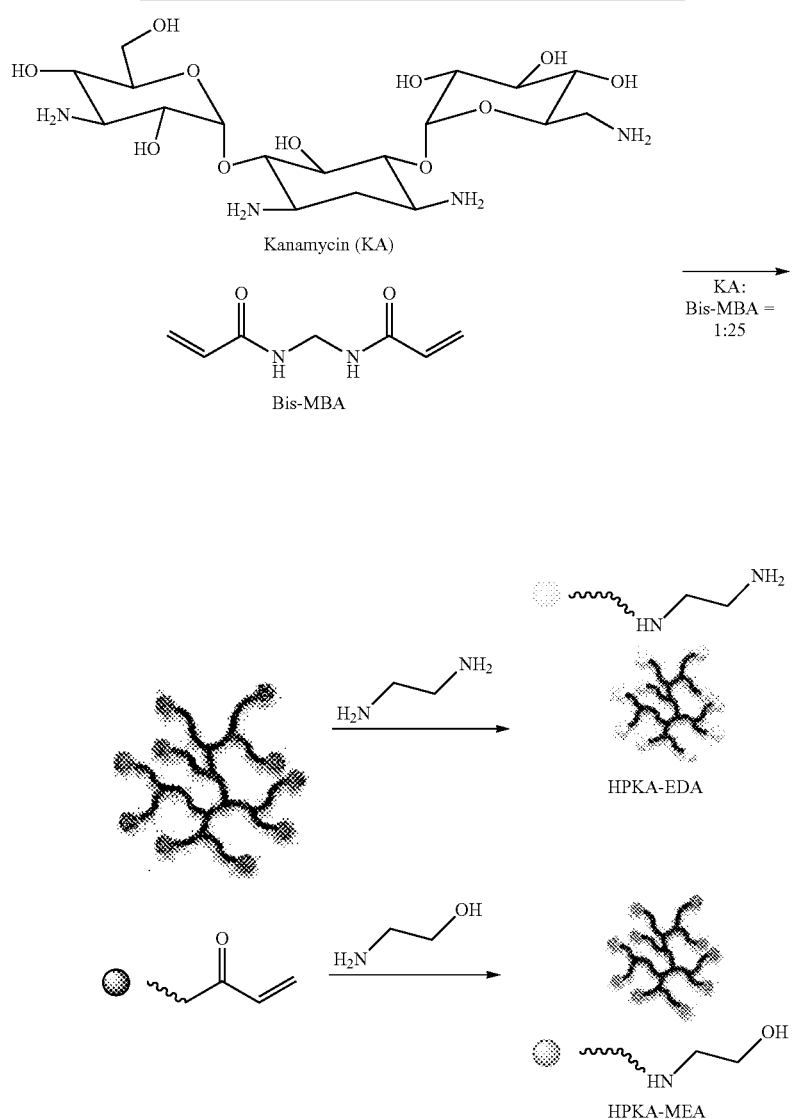

To obtain HPKA with various exterior functional groups, 2.5 mmol KA was first mixed with 6.25 mmol MBA in 50 mL D.I. water supplemented with sodium bicarbonate that neutralize the sulfate existed in aminoglycoside and reacted for 3 days at 50° C. under nitrogen stream. 0.5 mL EDA or HPKA-EDA consisted of the following peaks: 1.0-1.5 (CHCH$_2$CH); 2.2-3.3 (O=CCH$_2$CH$_2$, O=CCH$_2$CH$_2$, NCH, CHNH, CHNH$_2$, CHCH$_2$NH$_2$, CHCH$_2$NH$_2$, CHCH$_2$N, CH$_2$CH$_2$OH), 3.3-3.8 (CH$_2$OH), 4.4 (NHCH$_2$NH), 5.0-6.0 (CH(OCH)$_2$CH).

1.4 Molecular Weight and Polydispersity of Hyperbranched Polyaminoglycosides.

The molecular weight and polydispersity index (PDI) of HPA were determined by size exclusion chromatography-light scattering (SEC-LS) characterization, and the data was summarized in Table 1.

TABLE 1

Characterizations of hyperbranched polyaminoglycosides.

| Polysaccharides | $Mn^a$ (g mol$^{-1}$) | $Mw^a$ (g mol$^{-1}$) | $PDI^a$ | $DB^b$ | Nitrogen$^c$ (wt %) |
|---|---|---|---|---|---|
| HPKA | $4.30 \times 10^3$ | $6.70 \times 10^3$ | 1.56 | 0.49 | 10.71 |
| HPNE | $1.63 \times 10^4$ | $2.07 \times 10^4$ | 1.27 | 0.58 | 12.23 |
| HPGE | $2.35 \times 10^4$ | $3.92 \times 10^4$ | 1.67 | 0.32 | 14.21 |
| HPKA-EDA | $3.73 \times 10^3$ | $5.74 \times 10^3$ | 1.54 | 0.45 | 15.18 |
| HPKA-MEA | $3.63 \times 10^3$ | $7.07 \times 10^3$ | 1.95 | 0.46 | 12.70 |

$^a$Molecular weight was determined by SEC-LS characterization.
$^b$DB (degree of branching) was estimated base on quantitative $^{13}$C NMR.
$^c$Nitrogen (wt %) was determined by CHN element analysis.

The molecular weight for HPA was found to be dependent on the aminoglycoside identities, which was most likely due to their different reactivity. The molecular weight and PDI for HPKA-EDA and HPKA-MEA were found to be similar with HPKA. These HPAs were further characterized by 1H NMR, FTIR, and 13C NMR (Supporting information). Generally, the consumption of peaks at 5.6-6.6 ppm from double bonds of diacrylate and the appearance of newly formed saturated double bounds at 2.2-3.0 ppm confirmed the polymerization between aminoglycosides and bis-MBA (FIGS. 3A-3E). FTIR spectra showed bands located at ~2930 and ~2840 cm$^{-1}$, which were assigned to $CH_2$ stretching vibration. Meanwhile, the bands at ~1650 cm$^{-1}$ and ~1530 cm$^{-1}$ were assigned to carbonyl stretching of bis-MBA and amino bending vibration of aminoglycosides, respectively, further confirming the successful polymerization (FIGS. 4A-4E). Quantitative 13C NMR provided evidence for the formation of hyperbranched structure. As a typical hyperbranched polymer, HPA is composed of dendritic unit, linear unit, and terminal unit. The appearance of various peaks between 25-60 ppm was due to the formation of ethylene group (i.e., —$CH_2$—$CH_2$—) under different chemical environments (i.e., dendritic unit and linear unit). The detailed assignments for these ethylene groups were determined according to previous reports, and the results were given in FIGS. 5A-5E. The degree of branching (DB) was estimated based on the following equation: DB=2D/(2D+L).15, 25 The DBs of HPKA, HPNE, and HPGE ranged from 0.32 to 0.58 (Table 1). The difference in DBs was again attributed to the different reactivity of aminoglycoside. For HPKA-MEA and HPKAEDA, the DBs were comparable with HPKA (i.e., 0.45 for HPKA-EDA and 0.46 for HPKA-MEA).

Example 2: NO Release Characteristics of Certain Embodiments

Synthesis of N-diazeniumdiolate NO Donor-Modified Polysaccharides.

Macromolecular scaffolds (e.g., silica, polyamidoamine dendrimers, chitosan) for NO-release application often require additional modification steps to create reactive sites for the addition of NO donor. Hyperbranched polyaminoglycosides benefit from the existence of linear units which provide secondary amines that can be directly functionalized with N-diazeniumdiolate NO donor (or other NO donors).

To impart NO release capacity, HPAs were reacted with high pressure (10 atm) of NO under basic solution, yielding N-diazeniumdiolate NO donor-functionalized HPA (i.e., HPKA/NO, HPNE/NO, HPGE/NO, HPKA-EDA/NO, and HPKA-MEA/NO). Briefly, hyperbranched polyaminoglycosides (20 mg) were mixed with 20 μL sodium methoxide (5.4 M) in 1 mL D.I. water. The reactor was flushed with argon three times, followed by three additional longer times (10 min each) to remove oxygen. The reactor was then filled with 10 atm NO pre-purified by KOH pellet. The pressure was maintained to allow the formation of N-diazeniumdiolate NO donor on the secondary amines of the polymers. After 3 days, the reactor was flushed with argon again using the same procedure as mentioned above to remove the unreacted NO. The product (i.e., HPKA/NO, HPNE/NO, HPGE/NO, HPKA-EDA/NO, and HPKA-MEA/NO) was precipitated by acetone, followed by washing with methanol, and dried in vacuum box.

Characterization of NO Bound HPA

Figure 6:
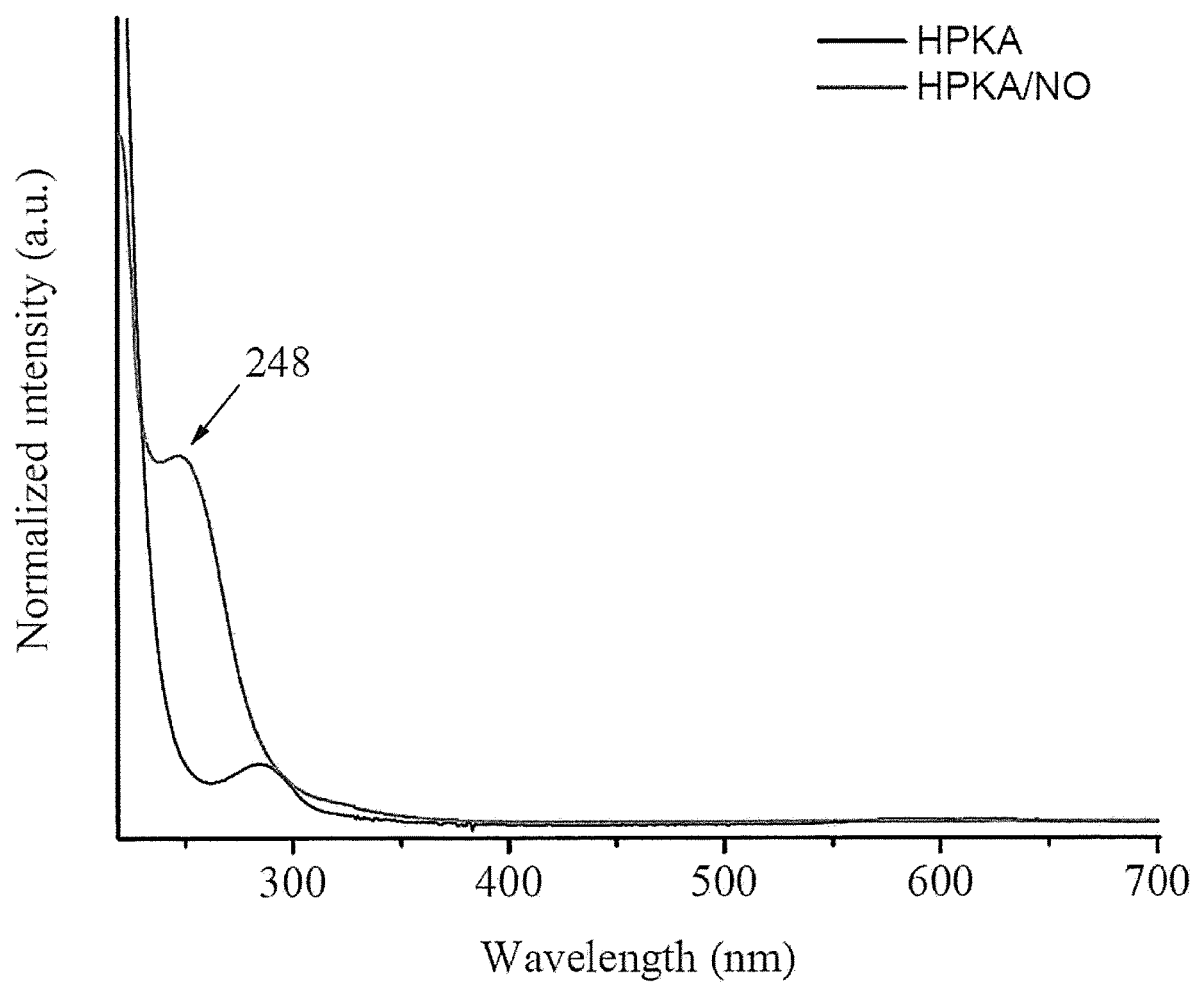
FIG. 6 is a representative UV-vis spectra for: HPKA (black); and HPKA/NO (red showing a shoulder at 248 nm).

The successful formation of N-diazeniumdiolate NO donor was confirmed by UV-vis spectroscopy, as indicated by the appearance of peak at ~250 nm that is absent for the non-NO-releasing scaffold (FIG. 6). 1H NMR and SEC-LS characterization (not shown) confirmed the integrity of scaffold after reacting with NO.

Characterization of Nitric Oxide Release.

A chemiluminescence nitric oxide analyzer was used to evaluate NO-release properties of the scaffolds in PBS (pH 7.4, 37° C.). NO-releasing hyperbranched polyaminoglycosides with accurately weighed mass (~1 mg) were added to deoxygenated 10 mM phosphate buffered saline (PBS, 30 mL, pH 7.4) at 37° C. Nitrogen was bubbled through this solution at a flow rate of 70 mL min$^{-1}$ to carry the liberated NO to a Sievers chemiluminescence nitric oxide analyzer (Boulder, Colo.). Additional nitrogen flow was supplied to the flask to match the collection rate of the instrument at 200 mL min$^{-1}$. The real-time NO release profiles were recorded until the observed NO levels decreased below 10 ppb mg$^{-1}$ scaffold. The total NO storage was normalized to the mass of added scaffold as μmol NO mg$^{-1}$ scaffold.

For aminoglycoside-terminated HPA, differences in total NO storages (~0.41 μmol mg$^{-1}$ to ~0.60 μmol mg$^{-1}$) and NO-release kinetics ($t_{1/2}$~81 min to ~147 min) were observed (see Table 2). This was attributed to the difference in the amine concentration of these constructs, as indicated by the nitrogen content (Table 1). HPGE/NO that contained highest amine concentration exhibited greatest NO totals and most extended NO-release kinetics compared to HPKA/NO and HPNE/NO. Without being bound by theory, the longer half-life was likely due to the formation of intramolecular hydrogen bonding by the neighboring cationic amines that stabilized N-diazeniumdiolate anions. It is also possible that the presence of surrounding amines increases the localized pH, slowing down proton-initiated N-diazeniumdiolate decomposition.

TABLE 2

Nitric oxide release characterization for polysaccharides.$^a$

| Polysaccharides | t[NO] (μmol mg$^{-1}$)$^b$ | t[NO]$_{2h}$ (μmol mg$^{-1}$)$^c$ | $t_{1/2}$ (min)$^d$ |
|---|---|---|---|
| HPKA/NO | 0.41 ± 0.08 | 0.23 ± 0.07 | 81 ± 30 |
| HPNE/NO | 0.54 ± 0.14 | 0.29 ± 0.08 | 103 ± 33 |
| HPGE/NO | 0.60 ± 0.14 | 0.25 ± 0.07 | 147 ± 23 |

TABLE 2-continued

Nitric oxide release characterization for polysaccharides.[a]

| Polysaccharides | t[NO] ($\mu$mol mg$^{-1}$)[b] | t[NO]$_{2h}$ ($\mu$mol mg$^{-1}$)[c] | t$_{1/2}$ (min)[d] |
|---|---|---|---|
| HPKA-EDA/NO | 1.20 ± 0.21 | 0.46 ± 0.07 | 185 ± 25 |
| HPKA-MEA/NO | 1.28 ± 0.28 | 0.77 ± 0.17 | 74 ± 21 |

[a]n ≥ 3 separate syntheses;
[b]Total NO storage per milligram polyesters;
[c]NO released amount for the initial 2 h;
[d]Half-life of NO release.

Figure 7:
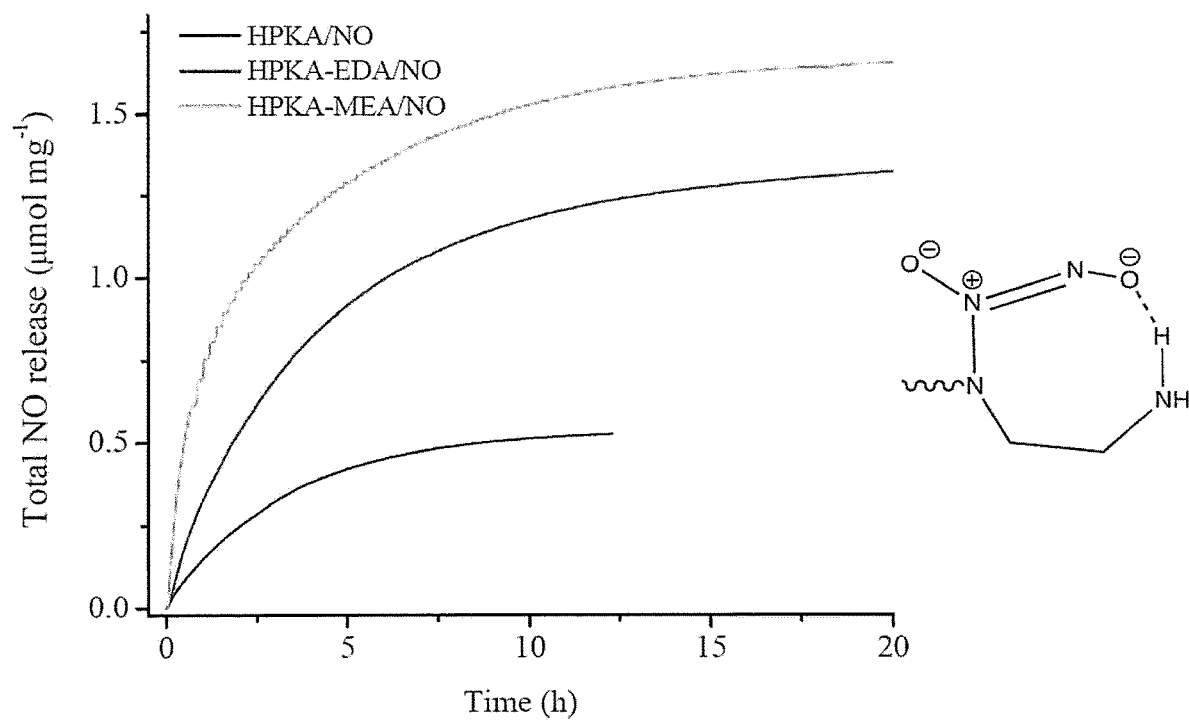
FIG. 7 shows the cumulative nitric oxide release from: HPKA/NO (black); HPKA-EDA/NO (red); HPKA-MEA/NO (green), and scheme for the intramolecular hydrogen bonding formation.

Exchanging the terminal groups of HPKA from KA to EDA or MEA resulted in an unexpected increase in NO-release totals (FIG. 7). HPKA-EDA/NO and HPKA-MEA/NO exhibited greater NO totals (~1.20 $\mu$mol mg$^{-1}$) compared to HPKA/NO (~0.41 $\mu$mol mg$^{-1}$), even though the amine content did not change significantly, as indicated by the nitrogen content (wt %). Without being bound by theory, the higher nitrogen content observed for HPKA-EDA was believed to be due to the introduction of more primary amines that do not contribute to the formation of stable N-diazeniumdiolate NO donors. Thus, without being bound to a particular theory, it is theorized that the difference in NO totals was due to the position of secondary amines that affected their reactivity with NO. For HPKA, the secondary amines provided from linear units would be randomly distributed along the polymer backbone (Scheme 1). The interior secondary amines may have limited reactivity to form the NO donor.

In comparison, the synthesis of HPKA-EDA and HPKA-MEA would result in the secondary amines concentrating at the exterior of the scaffold, leading to an enhanced NO donor formation efficacy (Scheme 2). The identity of exterior functional groups also greatly affected NO-release kinetics. Without being bound to a particular theory, it is believed this enhancement is attributable to the difference in chemical structure. The NO-release kinetics of HPKA-EDA/NO (t$_{1/2}$~185 min) was more extended compared to HPKA-MEA/NO (t$_{1/2}$~74 min). It is believed that the formation of hydrogen bonding and localized pH (e.g., localized pH differences) play a role on the resulting NO-release kinetics. It is believed that the terminal primary amine from EDA stabilized the NO donor and increased the local pH, leading to a slower NO release profile (FIG. 7).

Example 3: Anti-Microbial Characteristics of Certain Embodiments

The following describes testing that was performed using example embodiments of HPAs. The antibacterial activities of control and NO-releasing HPA were evaluated against various dental disease causing bacteria species (i.e., *P. gingivalis, A. actinomycetemcomitans, A. viscosus*, and *S. mutans*). Specifically, *P. gingivalis* and *A. actinomycetemcomitans* belong to Gram-negative class, and they are commonly related to periodontal diseases. *S. mutans* and *A. viscosus* are Gram-positive species, and they have been considered as key etiological agents for dental caries. The wide range of dental bacteria species chosen in the present disclosure ensured the potential universality of the resulting conclusion in the aspect of oral therapeutics.

Planktonic Bactericidal Assays.

Planktonic bacteria species (i.e., *P. gingivalis, A. actinomycetemcomitans, S. mutans*, and *A. viscosus*) were initially stored in 15% glycerol PBS at ~80° C. To perform the bactericidal assay, a frozen stock was grown in BHI broth (W—C anaerobic broth for *P. ginigvalis*) at 37° C. overnight, and allowed for growing to 108 colonies forming unit per milliliter (CFU mL$^{-1}$) determined by optical density (OD 600 nm). *P. ginigvalis* was cultured anaerobically. *A. actinomycetemcomitans* and *A. viscosus* were cultured in a microaerophilic environment. *S. mutans* was cultured aerobically. Bacteria were then diluted to 106 CFU/mL in 1% BHI (W—C anaerobic broth for *P. ginigvalis*)-supplemented PBS and exposed to various NO-releasing and respective control materials for 2 hours at 37° C.

Bactericidal Study Against Planktonic Dental Pathogens.

Bactericidal assay was performed under nutrient-supplemented condition (i.e., 1% broth-supplemented PBS, pH 7.4, 37° C.). Minimum bactericidal concentration (MBC, mg mL$^{-1}$), a 3-log reduction in bacterial viability, was used to quantify the scaffolds antibacterial efficacy. To quantify the antibacterial capacities of materials against planktonic bacterial, the minimum bactericidal concentration (e.g., the minimum concentration of materials required to achieve a 3-log reduction in viability after 2 hours) was determined.

NO dose was derived by multiplying the amount of NO delivered over the 2 h exposure time (i.e., t[NO]$_{2h}$) and the corresponding MBC values. The values of MBC and NO dose were provided in Table 3 and Table 4. The much lower MBC values for NO-releasing HPA compared to control (i.e., non-NO-releasing) HPA demonstrated that NO was the bactericidal agent. Indeed, it is believed that NO can exert antibacterial capacities through the introduction of extracellular nitrosative and intracellura oxidative stress, leading to cell death via multiple mechanisms. Further inspection of MBC values and NO dose revealed that the Gram-negative bacteria (i.e., A. actinomyctemcomitans and *P. gingivalis*) were more sensitive to NO treatment compared to Gram-positive bacteria species (i.e., *S. mutans* and *A. viscosus*). Without being bound to a particular theory, this was attributed to the thicker peptidoglycan cell membrane of Gram-positive bacteria that is more resistant to NO diffusion, consistent with previous observations.

TABLE 3

The minimum bactericidal concentration (MBC, mg mL$^{-1}$) and NO dose ($\mu$mol mL$^{-1}$) of polyaminoglycosides against gram-negative dental pathogens.[a]

| | *P. gingivalis* | | *A. actinomycetemcomitans* | |
|---|---|---|---|---|
| Polysaccharides | MBC (mg mL$^{-1}$) | NO dose ($\mu$mol mL$^{-1}$) | MBC (mg mL$^{-1}$) | NO dose ($\mu$mol mL$^{-1}$) |
| HPKA | 16 | | 16 | |
| HPKA/NO | 2 | 0.46 | 1 | 0.23 |
| HPNE | 16 | | 8 | |
| HPNE/NO | 0.5 | 0.15 | 0.5 | 0.15 |
| HPGE | >16 | | 16 | |
| HPGE/NO | 4 | 1.00 | 2 | 0.50 |
| HPKA-EDA | >16 | | 16 | |
| HPKA-EDA/NO | 4 | 1.84 | 2 | 0.92 |
| HPKA-MEA | >16 | | 16 | |
| HPKA-MEA/NO | 2 | 1.54 | 1 | 0.77 |

[a]n ≥ 3 replicates

TABLE 4

The minimum bactericidal concentration (MBC, mg mL$^{-1}$) and NO dose (μmol mL$^{-1}$) of polysaccharides against gram-positive dental pathogens.[a]

|  | S. mutans | | A. viscosus | |
| --- | --- | --- | --- | --- |
| Poly-saccharides | MBC (mg mL$^{-1}$) | NO dose (μmol mL$^{-1}$) | MBC (mg mL$^{-1}$) | NO dose (μmol mL$^{-1}$) |
| HPKA | >16 | | >16 | |
| HPKA/NO | 4 | 0.92 | 2 | 0.46 |
| HPNE | >16 | | 8 | |
| HPNE/NO | 4 | 1.16 | 1 | 0.29 |
| HPGE | >16 | | >16 | |
| HPGE/NO | >16 | >4.00 | 4 | 1.00 |
| HPKA-EDA | >16 | | 16 | |
| HPKA-EDA/NO | 16 | 7.36 | 2 | 0.92 |
| HPKA-MEA | >16 | | >16 | |
| HPKA-MEA/NO | 8 | 6.16 | 4 | 3.08 |

[a]n ≥ 3 replicates

For HPA with different aminoglycoside identity, HPKA/NO and HPNE/NO that have higher DBs (degrees of branching) exhibited superior bactericidal activities compared to HPGE/NO that has lower DB. It is believed that with the increase in DBs of hyperbranched polymer, the spatial structure would become more compact associated with decreased hydrodynamic size. Thus, the enhanced bactericidal ability of HPKA/NO and HPNE/NO may be a result of a smaller size compared to HPGE/NO that enabled more efficient bacterial-scaffold association and penetration, ultimately improving intracellular NO delivery efficacy. Of note, the MBC values and NO dose observed for HPKA/NO and HPNE/NO were significantly lower (i.e., MBC<4 mg mL$^{-1}$) than that of previously reported NO-releasing scaffolds (i.e., MBC<48 mg mL$^{-1}$), suggesting the superiority of using NO-releasing hyperbranched polyaminoglycosides to battle dental pathogens.

Exchanging the exterior functional groups of HPKA from KA to EDA or MEA resulted in a decrease in their bactericidal efficacies, as evidenced by the increased NO dose required to achieve the same killing against tested dental pathogens. In addition, the NO doses of HPKA-EDA/NO and HPKA-MEA/NO were observed to be comparable for eradicating dental pathogens, despite their distinct NO-release kinetics. These data suggested the existence of aminoglycoside terminal group was a factor that contributed to the enhanced bactericidal capacity of HPKA/NO compared to HPKA-EDA/NO and HPKA-MEA/NO.

Confocal Fluorescence Microscopy for Visualizing Intracellular NO Accumulation and Bacterial Cell Membrane Disruption.

Figure 8A:
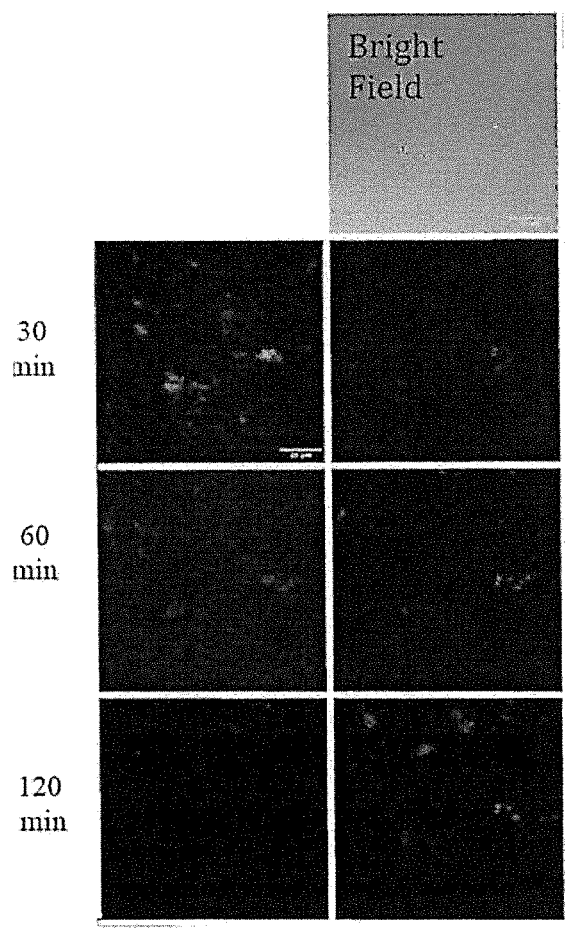
FIGS. 8A and 8B show confocal fluorescence images for visualizing the real-time antimicrobial behavior of A) HPKA/NO (0.1 mg mL$^{-1}$); B) HPKA-MEA/NO (0.1 mg mL-1) against *S. mutans*. Green fluorescence represents for DAF-2DA, and red fluorescence represents for PI. Scale bar=20 µm.
Figure 8B:
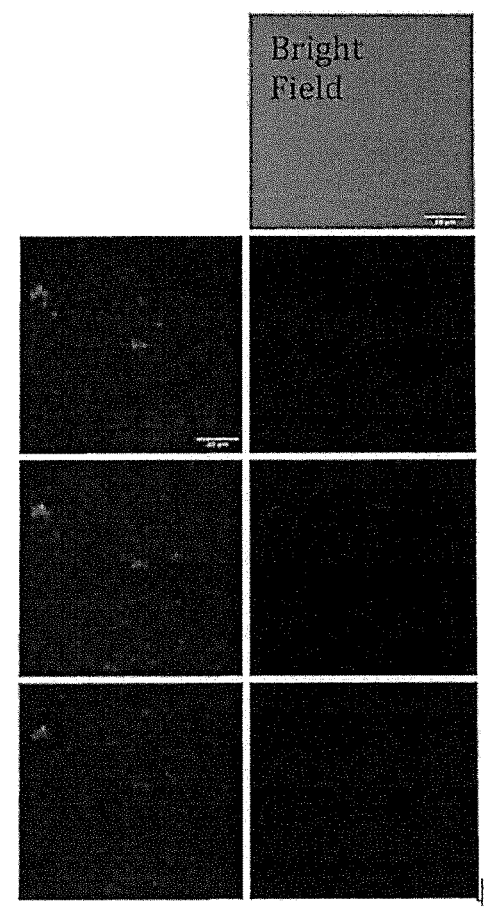

To elucidate the mechanism of this observed difference in bactericidal action, confocal fluorescence microscope was used to visualize intracellular NO and cell membrane damage, using DAF-2DA and PI fluorescence probe, respectively (FIGS. 8A and 8B). After exposing S. mutans to HPKA/NO, an initial intracellular NO accumulation (at 30 min) was observed, followed by the appearance cell membrane damage and depletion of the accumulated NO (starting from 60 min). However, only the appearance of intracellular NO with little cell membrane damage was observed after exposure of S. mutans to HPKA-MEA/NO at the same concentration. The confocal fluorescence data indicated that the improved bactericidal action for HPKA/NO was the result of more efficient cell membrane damage through the synergistic effects between kanamycin terminal group and NO.

The exemplary bacteria (i.e., S. mutans) was cultured to 108 CFU mL$^{-1}$ as described above and diluted to 106 CFU mL$^{-1}$ with medium (i.e., PBS) supplemented with 10 μM DAF-2DA for detection of intracellular NO accumulation and 30 μM PI for detection of cell membrane damage. Bacteria solutions (3 mL) were pre-incubated in a glass bottom confocal dish for 45 min at 37° C. A Zeiss 510 Meta inverted laser scanning confocal microscope (Carl Zeiss, Thornwood, N.Y.) with a 488 nm Ar excitation laser (20.0 mW 2.0% intensity) with a BP 505-530 nm filter was used to obtain DAF-2DA signal (green). A 543 nm HeNe excitation laser (1.0 mW, 20.0% intensity) with a BP 560-615 nm filter was used to obtain PI signal (red). Both bright field and fluorescence images were collected using an N.A. 1.2 C-apochromat water immersion lens with a 40× objective. Bacteria culture was exposed to HPKA/NO or HPKA-MEA/NO at final concentration of 100 μg mL$^{-1}$. Images were collected every 15 min.

In Vitro Cytotoxicity.

The toxicity against mammalian cells is an important factor when evaluating a newly developed antibacterial agent. To evaluate the potentials of these hyperbranched polyaminoglycosides for oral therapeutics, cytotoxicity against human gingival fibroblasts (HGF-1), a common cell line used for the evaluation of dental materials, was tested at various concentrations. The viability of HGF-1 was monitored by MTS assay after 2 h exposure time.

Human gingival fibroblasts (HGF-1) were grown in FibroLife fibroblast serum-free media, and incubated in 5 vol % CO2 under humidified conditions at 37° C. The cells were trypsinized after reaching 80% confluency, followed by seeding onto tissue culture treated polystyrene 96-well plates at a density of ~2×104 cells/mL. The plates were further incubated at 37° C. for 24 h. The supernatant was then aspirated and replaced with 100 μL of fresh growth medium with varying concentrations of hyperbranched polyaminoglycosides scaffolds. After 2 h incubation at 37° C., the supernatant was aspirated and washed with DPBS. A mixture of DMEM/MTS/PMS (105/20/1, v/v/v) solution (100 μL) was then added to each well, and incubated for 3 h at 37° C. The absorbance of the colored solutions was quantified at 490 nm using a Thermoscientific Multiskan EX plate reader (Waltham, Mass.). The mixture of DMEM/MTS/PMS and untreated cells were used as a blank and control, respectively. Results were expressed as percentage of relative cell viability as follows:

% cell viability=[(Abs490−Absblank)·/(Abscontrol−Absblank)]×100%     (eq. 1)

A killing curve was constructed for non-NO-releasing and NO-releasing hyperbranched polyaminoglycosides by plotting % cell viability versus concentration (mg mL$^{-1}$).

Figure 9A:
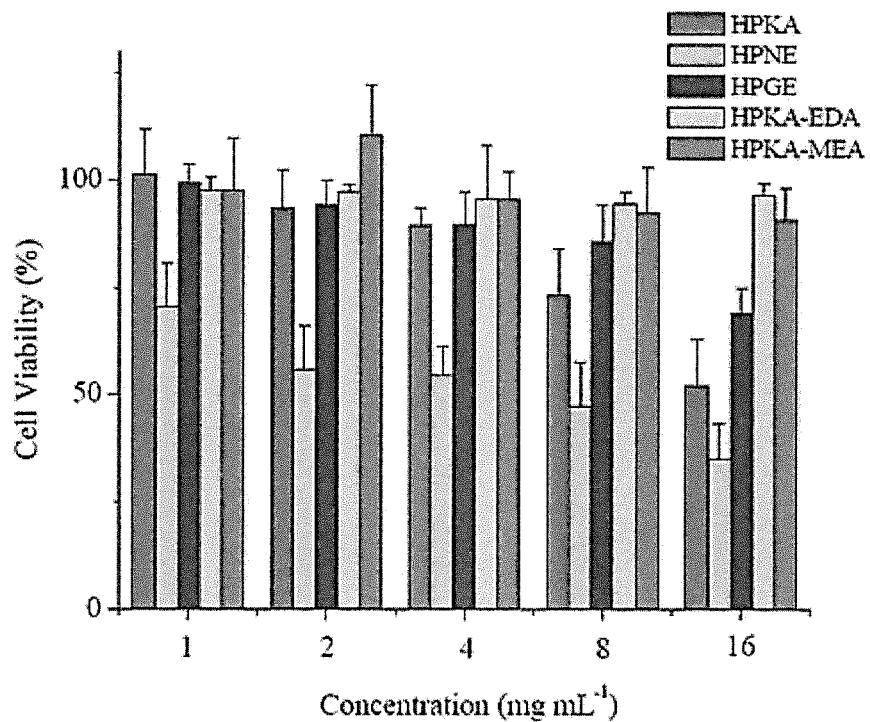
FIGS. 9A and 9B show percent viability of human gingival fibroblasts following 2 h exposure to: A) control and B) NO-releasing hyperbranched polyaminoglycosides.
Figure 9B:
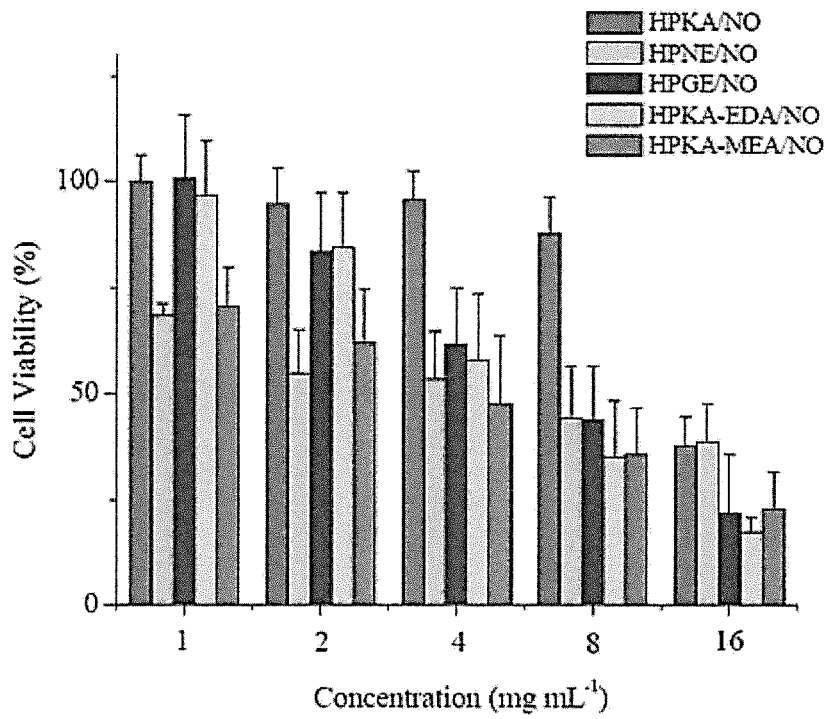

For control hyperbranched polymer terminated with aminoglycoside, HPNE exhibited highest toxicity, while HPGE exhibited lowest toxicity, consistent with their bactericidal ability. Exchanging exterior functional groups of HPKA from KA to EDA or MEA decreased the toxicity of scaffold at high concentrations (i.e., >8 mg mL$^{-1}$), indicating that aminoglycoside terminal groups may induce certain degree of adverse effects against mammalian cells at these concentrations (FIGS. 9A and 9B). The addition of NO-release capacities inhibited the viability of HGF-1 compared to control hyperbranched polyaminoglycosides (FIGS. 4A-4E). Nevertheless, HPKA/NO was found to be non-toxic (i.e., >80% cell viability), and HPNE/NO was found to exhibit minimal toxicity (i.e., >50% cell viability) to HGF-1 at their effective bactericidal concentrations (i.e., 4 mg m$^{-1}$).

CONCLUSION

Herein, a synthetic protocol for preparing NO-releasing hyperbranched polyaminoglycosides capable of NO storage and release kinetics over wide ranges was provided. The total NO storage and associated NO-release kinetics were highly dependent on the identity of aminoglycoside monomer and specific exterior functional groups. The antibacterial action of the NO-releasing hyperbranched polyaminoglycoside was examined against common dental pathogens. The combination of aminoglycoside terminal group and NO-release capacities that led to more efficient cell damage contributed to the improved bactericidal ability of scaffolds. In some embodiments, it was found that the combination of an aminoglycoside terminal group and NO produced greater bacteria membrane damage and bactericidal action.

Indeed, the NO-releasing hyperbranched polykanamycin and polyneomycin exhibited broad-spectrum bactericidal action. The favorable NO payloads, release kinetics, bactericidal action, and cytotoxicity suggest that these biopolymer scaffolds show high promise for a number of therapeutic applications beyond oral health. As an example, in some embodiments HPKA/NO and HPNE/NO exhibited broad-spectrum antibacterial activities against both Gram-positive cariogenic and Gram-negative periodontal pathogens. As these hyperbranched polyaminoglycosides were also found to not elicit significant toxicity to mammalian cells, they may be promising their potentials for oral therapeutics.

That which is claimed:

1. A hyperbranched polyaminoglycoside, comprising a first aminoglycoside unit comprising Formula II:

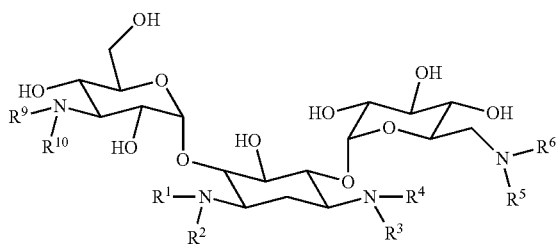

Formula II wherein each of R$^1$, R$^2$, R$^3$, R$^4$, R$^5$, R$^6$, R$^9$, and R$^{10}$ is independently selected from —H or represents a covalent bond to one or more linking units;
wherein a linking unit of the one or more linking units is represented by the following structure:

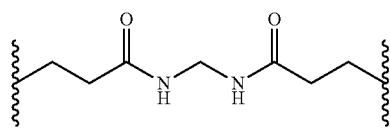 [SMILES: *CCC(=O)NCNC(=O)CC*]

wherein at least one linking unit forms a covalent bridge between the first aminoglycoside unit and a second aminoglycoside unit; and wherein at least one aminoglycoside unit of the hyperbranched polyaminoglycoside is derived from kanamycin;
wherein at least one aminoglycoside unit of the hyperbranched polyaminoglycoside comprises one or more terminal units selected from:

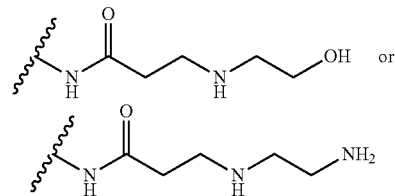

and
wherein at least a secondary amine of the hyperbranched polyaminoglycoside comprises a N-diazeniumdiolate NO donor.

2. The hyperbranched polyaminoglycoside of claim 1, additionally comprising one or more dendritic units having the structure:

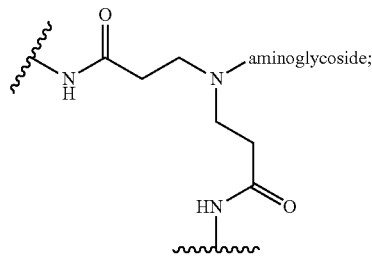

where "—N-aminoglycoside" represents the structure of Formula II.

3. The hyperbranched polyaminoglycoside of claim 1, additionally comprising one or more linear units having the structure:

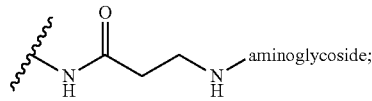

where "—N-aminoglycoside" represents the structure of Formula II.

4. The hyperbranched polyaminoglycoside of claim 1, wherein at least one secondary amine of the hyperbranched polyaminoglycoside comprises a NO donor.

5. The hyperbranched polyaminoglycoside of claim 1, wherein the hyperbranched polyaminoglycoside has a number average molecular weight of less than or equal to about 4 kDa.

6. The hyperbranched polyaminoglycoside of claim 1, wherein the hyperbranched polyaminoglycoside has a weight average molecular weight of less than or equal to about 7 kDa.

7. The hyperbranched polyaminoglycoside of claim 1, wherein the hyperbranched polyaminoglycoside has a NO storage capacity of greater than or equal to about 0.4 μmol NO/mg hyperbranched polyaminoglycoside.

8. The hyperbranched polyaminoglycoside of claim 1, wherein the hyperbranched polyaminoglycoside provides greater than or equal to about 99% bacterial reduction in a bacterial viability assay performed under static conditions over 2 hours against one or more of *P. aeruginosa, S. aureus P. gingivalis, A. actinomycetemcomitans, A. viscosus*, and/or *S. mutans* at a concentration of less than or equal to about 2 mg/mL.

9. A hyperbranched polyaminoglycoside, comprising a first aminoglycoside comprising a structure of Formula I:

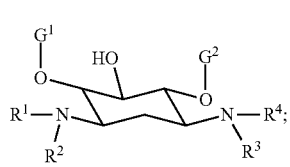

Formula I wherein $G^1$ is selected from the group consisting of:

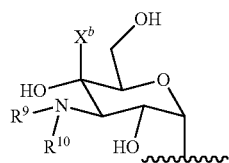 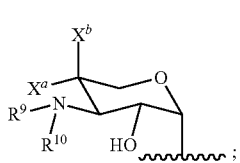

wherein $G^2$ is selected from the group consisting of:

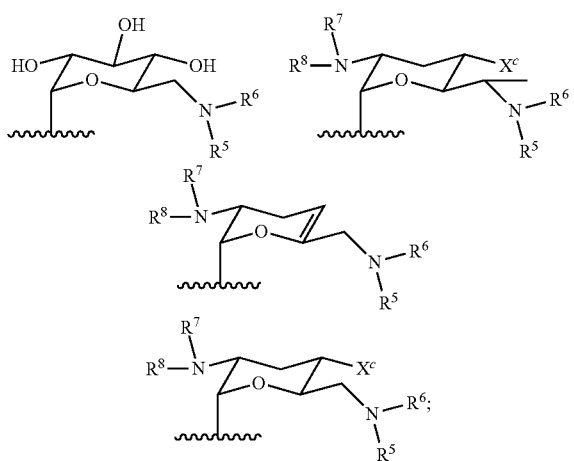

$R^1$, $R^2$, $R^3$, $R^4$, $R^5$, $R^6$, $R^7$, $R^8$, $R^9$, and $R^{10}$ are independently selected from the group consisting of —H, optionally substituted $C_1$-$C_6$ alkyl, optionally substituted polyamino having 1 to 6 repeat units with intervening $C_1$-$C_6$ alkyl groups, optionally substituted polyether having 1 to 6 repeat units with intervening $C_1$-$C_6$ alkyl groups, and a covalent bond to a linking unit;

$X^a$, $X^b$, and $X^c$ are independently selected from —H, —OH, and $C_1$-$C_6$ alkyl;

wherein at least one of $R^1$, $R^2$, $R^3$, $R^4$, $R^5$, $R^6$, $R^7$, $R^8$, $R^9$, and $R^{10}$ is a covalent bond to one or more linking unit selected from the group consisting of:

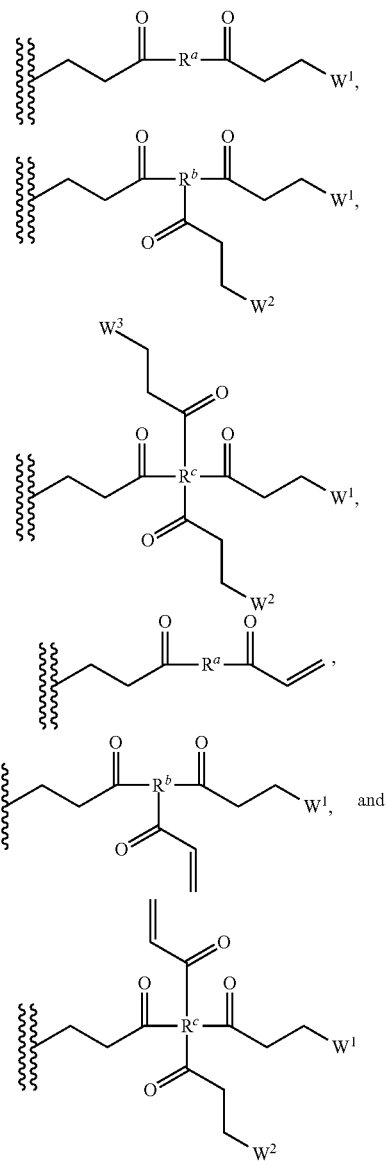

wherein "⦃" indicates an attachment to the first aminoglycoside;

$W^1$, $W^2$, or $W^3$, where present, are independently selected from one or more additional aminoglycosides or one or more end-capping substituents and at least one linking unit provides a covalent bridge from the first aminoglycoside to a second aminoglycoside;

$R^a$, $R^b$, and $R^c$ are independently selected from the group consisting of optionally substituted $C_1$-$C_6$ alkyl, optionally substituted polyamino having 1 to 6 repeat units (with $C_1$-$C_6$ alkyl(s)), or optionally substituted polyether having 1 to 6 repeat units (with $C_1$-$C_6$ alkyl(s)); and wherein the one or more end-capping substituents, where present, independently have a formula of —NH—$((CH_2)_aX^1)_b$—$(CH_2)_c$H where $X^1$ is O or NH and a, b, and c are independently an integer from 0 to 10, and wherein said hyperbranched polyaminoglycoside further comprises a NO-donating group, and wherein at least one aminoglycoside unit of the hyperbranched polyaminoglycoside comprises one or more terminal units selected from:

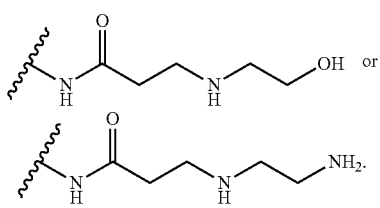 or

10. The hyperbranched polyaminoglycoside of claim 9, wherein the first aminoglycoside comprises a structure of Formula II:

Formula II

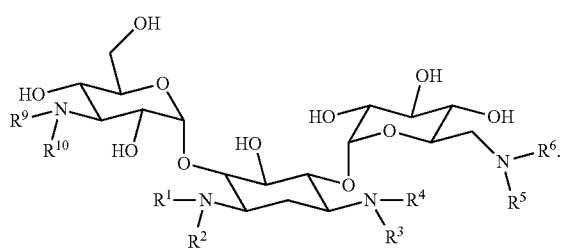

11. The hyperbranched polyaminoglycoside of claim 9, wherein the first aminoglycoside comprises a structure of Formula III:

Formula III

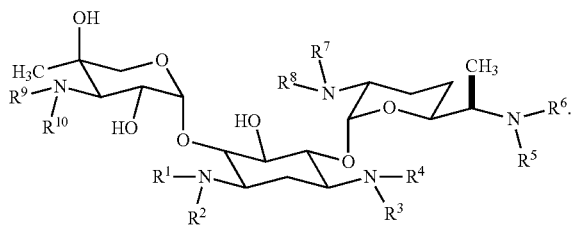

12. The hyperbranched polyaminoglycoside of claim 9, wherein the NO donating group is selected from the group consisting of:

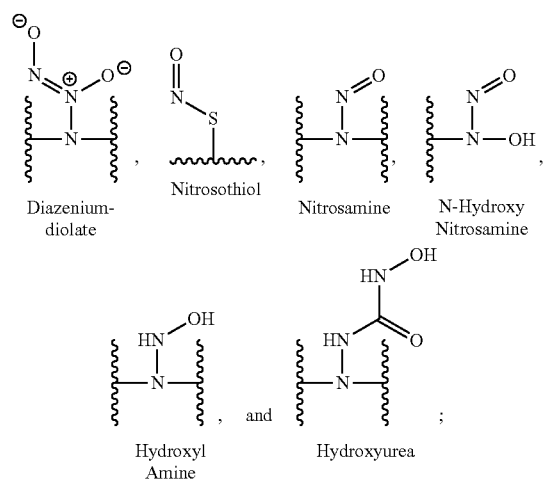

where "ξ" indicates attachment to other atoms within the hyperbranched aminoglycoside.

13. A method of decreasing microbial contamination comprising,
contacting a surface contaminated with a plurality of microbes with the hyperbranched polyaminoglycoside of claim 1;
wherein the nitric oxide donor generates nitric oxide and induces damage to the membrane and/or DNA of the microbes, thereby reducing the number of viable microbes.

14. A pharmaceutical formulation comprising:
the hyperbranched polyaminoglycoside of claim 1; and
a pharmaceutically acceptable carrier.

15. A method of delivering nitric oxide to a subject, comprising:
administering an effective amount of the hyperbranched polyaminoglycoside of claim 1 to reduce infection or bacterial load in the subject.

* * * * *

UNITED STATES PATENT AND TRADEMARK OFFICE
CERTIFICATE OF CORRECTION

PATENT NO. : 11,723,914 B2
APPLICATION NO. : 16/497696
DATED : August 15, 2023
INVENTOR(S) : Schoenfisch et al.

Page 1 of 1

It is certified that error appears in the above-identified patent and that said Letters Patent is hereby corrected as shown below:

In the Claims

Column 53,
Line 67, "unit; and" should read --unit;--.

Column 54,
Line 55, "a NO donor" should read --a further NO donor--.

Column 56,
Line 58, "alkyl(s)); and" should read --alkyl(s));--.

Signed and Sealed this
Ninth Day of April, 2024

Katherine Kelly Vidal
*Director of the United States Patent and Trademark Office*